United States Patent
Tsichlis et al.

(12) 
(10) Patent No.: US 6,617,427 B1
(45) Date of Patent: Sep. 9, 2003

(54) NUCLEIC ACID MOLECULE ENCODING AN ANKYRIN REPEAT TVL-1 PROTEIN AND METHODS OF USE THEREOF

(75) Inventors: Philip N. Tsichlis, Willow Grove, PA (US); Antonios Makris, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/339,746

(22) Filed: Jun. 24, 1999

Related U.S. Application Data

(60) Provisional application No. 60/090,742, filed on Jun. 24, 1998.

(51) Int. Cl.[7] .......................... C07K 14/47; C12N 15/12
(52) U.S. Cl. ...................................... 530/350; 536/23.5
(58) Field of Search ........................... 530/350; 536/23.5

(56) References Cited

U.S. PATENT DOCUMENTS 5,989,863 A * 11/1999 Tang et al. ................. 435/69.1

OTHER PUBLICATIONS

Watanabe et al. Transcription factor E4TF1 contains two subunits with different functions. EMBO journal (England) vol. 9 (3) p841–847, Mar. 1990.*

:Medline Abstract No. 99336788 Bethesda MD, National Library of Medicine Tomaras et al. ETS transcription factors regulate an enhancer activity in the third intron of TNF–alpha. Journal of leukocyte biology (United States), vol. 66 (1) p183, Jul. 1999.*

Watanabe et al. cDNA cloning of transcription factor E4TF1 subunits with Ets and notch motifs. Molecular and cellular biology (United States) vol. 13 (3) p1385–1391, Mar. 1993.*

Flory et al. Raf– 1 kinase targets GA–binding protein in transcriptional regulation of the human immunodeficiency virus type 1 promoter. Journal of Virology vol 70 (4):p2260–2268, Apr. 1996.*

Callard et al. The Cytokine FactsBook. New York: Academic Press. p. 31, 1994.*

Levy–Strumpf, et al., "Death associated proteins (DAPs): from gene identification to the analysis of their apoptotic and tumor suppressive functions", Oncogene, 1998, vol. 17, pp., 3331–3340.

Lin, et al., "The Ankyrin Repeat–containing Adaptor Protein Tvl–1 Is a Novel Substrate and Regulator of Raf–1", J. Biol. Chem., 1999, vol. 274, pp., 14706–14715.

Masternak, et al., "A gene encoding a novel RFX–associated transactivator is mutated in the majority of MHC class II deficiency patients", Nature Genetics, 1998, vol. 20, pp., 273–277.

* cited by examiner

*Primary Examiner*—Gabrielle Bugaisky
(74) *Attorney, Agent, or Firm*—Nanda P. B. A. Kumar; William J. McNichol, Jr.; ReedSmith LLP

(57) ABSTRACT

Nucleic acid molecules, proteins and antibodies are provided which may be used in biological screens to identify therapeutic agents involved in the regulation of cell cycle progression and apoptotic cell death.

8 Claims, 33 Drawing Sheets

FIG. 2C

1 MEPTQVAENLVPNQQPPVPDLEDPEDTRDESPENSDTVVLSLFPCTPDAV

51 NPEADASASSLQGSFLKHSTTLTNRQRGNEVSALPATLDSLSIHQLAAQG

101 ELSQLKDHLRKGACPACTCLSGNNLINKPDERGFTPLIWASAFGEIETVR

151 FLLDWGADPHILAKERESALSLASMGGYTDIVRLLLDRDVDINIYDWNGG

201 TPLLYAVRGNHVKCVEALLARGADLTTEADSGYTPMDLAVALGYRKVQQV

251 MESHILRLFQSTLGPVDPE 269

FIG. 2D

```
Concensus        -G--TPLHLAAR-GHVEVVKLLLD-GADVNA--TK
AKR repeat        SA    I SQ NNLDIAEV  K  NPD  D
                  V K    TMR  Q          SI  A 1st AKR      RGFTPLIWASAFGEIETVRFLLDWGADPHILAK 164
2nd AKR      ERESALSLASMGGYTDIVRLLLDRDVDINIYDW 197
3rd AKR      NGGTPLLYAVRGNHVKCVEALLARGADLTTEAD 224
4th AKR      SGYTPMDLAVALGYRKVQQVMESHILRLFQSIL 263

(Conditional AKR)  DSLSIHQLAAQGELSQLKDHLRKGNNLINKPDE 131
``` anti-FLAG

Hoechst 33258

```
   1 GTCGCGTATT AAGTTGCTGC TCTATGTCCC AGGAGAGGAA GCTAGAGAAC
  51 TGAGCGTCTG GTCACCAACT TGCTCTTTAC GAGATCTACT GAACCAGAAA
 101 AGTTTGTTGA ACAGAGTCTT CCTGAGTTTT GGAAGACCAA GGCTGGCAGC
 151 GTAGGGACAC AGAGGAGGCT GGAGGGAGCT TCCTCATGG AGCCCACTCA
 201 GGTTGCAGAG AACCTTGTCC CAAACCAGCA ACCTCCTGTT CCTGACCTAG
 251 AGGATCCTGA GGACACCAGA GATGAGTCCC CAGAGAACTC AGACACTGTC
 301 GTCCTCAGCC TGTTCCCCTG CACCCCAGAT GCTGTGAATC CTGAAGCAGA
 351 TGCCAGTGCA TCCTCACTGC AGGGAAGTTT CTTGAAGCAC TCCACAACCC
 401 TCACAAACCG GCAACGTGGG AATGAGGTCT CAGCTCTGCC AGCCACCCTG
 451 GACTCCCTTT CTATCCACCA GCTTGCAGCC CAAGGGGAGC TGAGCCAACT
 501 GAAGGATCAT CTGCGGAAGG GTGCGTGTCC TGCCTGCACA TGCCTGTCTG
 551 GAAACAACCT GATCAACAAA CCGGATGAGC GTGGCTTCAC CCCCCTCATC
 601 TGGGCCTCAG CCTTTGGAGA AATTGAGACA GTTCGCTTCC TGCTAGACTG
 651 GGGTGCTGAC CCCCACATCC TGGCCAAGGA GCGGGAGAGC GCACTGTCAC
 701 TTGCCAGTAT GGGTGGCTAC ACGGACATCG TGAGGTTGCT GCTTGACCGT
 751 GACGTGGATA TCAACATCTA TGACTGGAAT GGAGGAACAC CACTGCTCTA
 801 TGCTGTGCGT GGGAACCACG TGAAGTGTGT GGAGGCCTTA CTGGCCCGGG
 851 GTGCTGACCT CACCACAGAG GCTGACTCTG CTACACCCC AATGGATCTC
 901 GCAGTGGCCC TGGGATACCG CAAAGTGCAA CAGGTGATGG AGAGCCACAT
 951 CCTCAGATTG TTCCAGAGCA CCCTGGGGCC TGTGGACCCC GAGTGAAGAC
1001 AGCCTGCTGG GAACCCAGGC ACTCAGGGAC AGTCAGCCCA CAACTGGCTT
1051 GAAAGGCAGC TCCTGGACAG TGGTGGGAAA AGCCCTCCGC AACAGGAACC
1101 AATAAATCTG TGCAGAACTT AAAAAAAAAA AAAAAAACT CGAGAAGCTT
1151 TGGACTTCTT
```

FIG. 25

NUCLEIC ACID MOLECULE ENCODING AN ANKYRIN REPEAT TVL-1 PROTEIN AND METHODS OF USE THEREOF

This application claims the priority of U.S. Provisional Application No. 60/090,742, filed Jun. 24, 1998.

Pursuant to 35 U.S.C. §202(c) it is acknowledged that the U.S. Government has certain rights in the invention described herein, which was made in part with funds from the Public Health Service, Grant Numbers R01-CA38147 and CA06927.

FIELD OF THE INVENTION

The present invention relates to the fields of molecular biology and signal transduction. More specifically, the invention provides nucleic acid molecules, proteins and antibodies useful as targets for screening therapeutic agents that regulate-cell cycle progression and apoptotic cell death.

BACKGROUND OF THE INVENTION

Several publications are referenced in this application by numerals in parenthesis in order to more fully describe the state of the art to which this invention pertains. Full citations for these references are found at the end of the specification. The disclosure of each of these publications is incorporated by reference herein.

Programmed cell death (PCD) is a genetically controlled active process which removes cells that are harmful or no longer necessary for the organism. Morphologically, cells undergoing PCD suffer cytoplasmic membrane blebbing, chromatin condensation and disassembly into membrane-enclosed vesicles, called apoptotic bodies, and DNA fragmentation. This constellation of morphological features has been termed apoptosis. Although the terms PCD and apoptosis were originally coined to define different concepts, today they are used almost interchangeably. For the purpose of this application, the term apoptosis will be used exclusively.

Apoptosis plays an important role in development as well as in tissue homeostasis in adult animals. Tissues of adult animals undergo continuous renewal characterized by cellular proliferation, differentiation and death by apoptosis. Defects that increase the rate of cell death lead to degenerative diseases while defects that decrease it lead to cancer. A classical example of the latter are follicular B cell lymphomas that carry a t14;18 translocation and overexpress the Bcl-2 protooncogene.

As eucaryotic cells grow and divide, they progress through an ordered cycle of events in which chromosome replication (S-phase) and mitosis (M-phase) are separated by two gap phases (G1→S→G2→M→G1). The gap phases are punctuated by checkpoints, at which progression stalls if certain requirements are not met. The G1 checkpoint prevents S-phase if the cell has sustained damage to its DNA, and the G2 checkpoint ensures complete DNA-replication and chromosome integrity prior to mitosis. The timing of these events is coordinated by the sequential activation and inactivation of a series of kinase complexes consisting of a catalytic subunit (the cyclin dependent kinase or cdk) and a regulatory subunit (the cyclin). Each cell cycle phase is characterized by the activity of a specific set of cyclin/cdk complexes. In mammalian cells, cyclins D/cdk4 (or cdk6) and cyclin E/cdk2 are required for progression through G1 and entry into S phase, cyclin A/cdk2 is required during S phase and the mitotic cyclin B/cdk1 is required during G2 and mitosis. Waves of phase-specific CDK activities are generated by at least three means: undulations in the availability of catalytic subunits; regulatory phosphorylation and dephosphorylation of the catalytic subunits; and modulation of the abundance of inhibitory molecules.

The regulation of the cell cycle in cycling cells depends on oscillations of the activity of these and perhaps other molecules, controlled by an internal clock. In addition however, the mammalian cell cycle responds to external mitogenic signals. The response to such signals is restricted to the G1 phase of the cycle before the cells can commit to replicate their chromosomal DNA. The loss of mitogen dependency late in G1 marks the restriction point (G1 checkpoint or START). Signals required for, or modulating G1 progression are transduced via several signalling pathways.

Apoptosis and the cell cycle are intricately interconnected processes. Thus, dividing cells that do not fulfill the requirements to traverse the G1 or G2 checkpoints undergo either cell cycle arrest or apoptosis. As a result, death by apoptosis may occur at highly predictable points in the cell cycle and in response to signals generated by the machinery that monitors the requirements for cell cycle progression. This is exemplified by the outcome of conflicting signals that both stimulate and inhibit progression through the cell cycle. Such signals predictably induce apoptosis. Examples include: 1) the induction of apoptosis by serum starvation in cultured fibroblasts overexpressing c-myc; and 2) the induction of apoptosis by -irradiation or induction of p53 in cells expressing active E2F-1. In addition to these links between apoptosis and the cell cycle, it has also been shown recently that proteins that primarily regulate apoptosis, such as anti-apoptotic or proapoptotic members of the Bcl-2 family, also affect cell cycle progression. Finally, the same signalling molecules may target both regulators of the cell cycle and regulators of apoptosis.

Apoptosis and the cell cycle are fundamental biological processes. Exploring the regulation of these processes has already provided significant insights into the nature and the origin of genetic defects, degenerative diseases and cancer. The present invention provides composition and methods for identifying regulators of apoptotic cell death for the subsequent generation of beneficial, therapeutic agents.

SUMMARY OF THE INVENTION

This invention provides novel biological molecules useful for identification, detection and/or regulation of complex signalling events that regulate cell cycle progression and apoptotic cell death. According to one aspect of the invention, a nucleic acid molecule is provided that encodes a Tvl-1 protein between about 250 and 280 amino acids in length, said protein comprising a plurality of ankyrin repeat domains and promoting TNF-α induced apoptosis. In a preferred embodiment the protein has the amino acid sequence of SEQ ID NO:2. An exemplary nucleic acid of the invention comprises SEQ ID NO:1.

According to another aspect of the present invention, antibodies immunologically specific for the Tvl-1 protein are provided.

Various terms relating to the biological molecules of the present invention are used hereinabove and also throughout the specifications and claims. The terms "specifically hybridizing," "percent similarity" and "percent identity (identical)" are defined in detail in the description set forth below.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the genomic DNA of a prokaryote or eukaryote.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

With respect to antibodies of the invention, the term "immunologically specific" refers to antibodies that bind to one or more epitopes of a protein of interest (e.g., Tvl-1), but which do not substantially recognize and bind other molecules in a sample containing a mixed population of antigenic biological molecules.

With respect to oligonucleotides, the term "specifically hybridizing" refers to the association between two single-stranded nucleotide molecules of sufficiently complementary sequence to permit such hybridization under predetermined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The nucleic acids and proteins of the present invention are the products of a single gene (Tvl-1). The proteins encoded by the Tvl-1 gene function as adaptors that contribute to the assembly and/or stability of multi-molecular complexes. Since these proteins are present both in the cytoplasm and in the nucleus we propose that they contribute to the assembly/stability of multi-molecular complexes in both subcellular locations. The information disclosed in this application shows that the proteins encoded by Tvl-1 contribute to the assembly of cytoplastic and nuclear complexes involved in apoptosis and cell cycle regulation. Therefore, the nucleic acids proteins and antibodies of the present invention can be advantageously used as targets for development of novel therapeutic agents which regulate cell cycle progression and apoptotic cell death. The Tvl-1 molecules of the invention can also be used as research tools and will facilitate the elucidation of the mechanistic action of the novel genetic and protein interactions involved in the control of cellular proliferation and apoptosis.

BRIEF DESCRIPTION OF THE DRAWINGS

FIG. 16 is the Western blots showing that the interaction of caspase-9 with Tpl-2 is enhanced by Tvl-1.

FIG. 17 is the Western blots showing that caspase-3 interacts with Tvl-1 only in Tpl-2 transfected cells, but does not interact with Tpl-2.

FIG. 18B shows Western blots of total cell lysates derived from the same cells in FIG. 17A and probed with the indicated antibodies.

FIG. 25 is the cDNA sequence of Tvl-1 (SEQ ID NO:1).

DETAILED DESCRIPTION OF THE INVENTION

Figure 1:
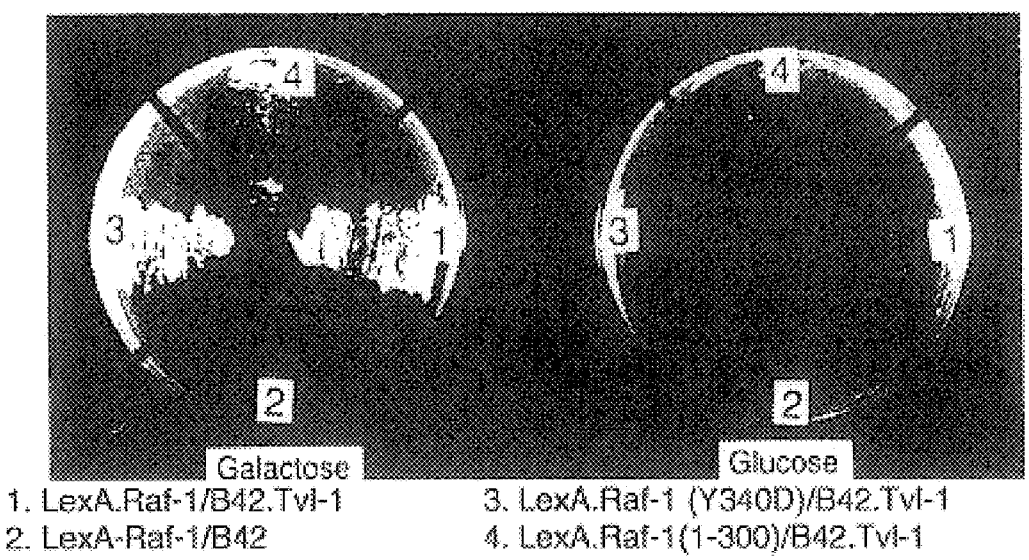
FIG. 1 is an experimental demonstration of Tvl-1 interaction with Raf-1 in the yeast two-hybrid system.

Following stimulation of membrane receptors, the Raf-1 kinase is activated and transduces signals to several signaling pathways (1–3). The molecular mechanism of Raf-1 activation is not well understood but appears to be under the control of a host of Raf-1-interacting macromolecules including both proteins and phospholipids (2, 4).

One of the mechanisms by which interacting macromolecules regulate the activity of Raf-1 is phosphorylation. Mitogenic stimulation leads to an increase in Raf-1 phosphorylation on serine, threonine, and in some cases, tyrosine residues (5, 6). Studies using overexpression systems have demonstrated that Raf-1 can be activated both by tyrosine phosphorylation mediated by members of the Src kinase family (7, 8) and by serine phosphorylation, mediated by protein kinase C (9). In contrast, cAMP-dependent protein kinase A (10) and an unidentified G-protein coupled tyrosine phosphatase downregulate the activity of Raf-1 (11). The significance of these kinases/phosphatases in regulating Raf-1 activation under physiological conditions is still inconclusive. However, it was recently shown that the Raf-1 activating phosphorylation at Y340, which is mediated by the Src family of kinases, is triggered by CD4 crosslinking in T cells (12) and by Fc RI crosslinking in myeloid cells (13). Phosphorylation of Raf-1 may be the final outcome of the interaction of Raf-1 with other macromolecules. However, the range of the effects of these interactions is quite diverse. Thus, it has been suggested that the interaction of Raf-1 with 14-3-3 (14–16), Hsp90/cdc37$^{P50}$ (17–19), or Ras (20–22) may alter the conformation of the kinase and may promote its stability. Moreover, via its interaction with Ras, Raf-1 may translocate to the plasma membrane (23, 24). Finally, the interaction of Raf-1 with Ras or 14-3-3 may promote the oligomerization of Raf-1 (25, 26).

The mechanisms by which three interacting macromolecules regulate the activation of Raf-1 are overlapping and interdependent, as exemplified by the interaction of Raf-1 with Ras. The GTP-charged form of Ras binds directly to the amino-terminal conserved region 1 (CR1) including the Ras-binding domain (RBD) and the cysteine-rich domain (CRD) or Raf-1 (27–29). This interaction causes translocation of Raf-1 from the cytosol to the plasma membrane where Raf-1 activation takes place (23, 24). However, targeting of Raf-1 to the plasma membrane by addition of a Ras prenylation signal is sufficient to activate the kinase by mechanisms that are Ras-independent (23, 24). The nature of these mechanisms and the macromolecules involved are currently not well defined. One such mechanism, however, may involve binding of Raf-1 to the oligomer forming adaptor protein 14-3-3 (30). Binding to this protein may induce oligomerization and activation of Raf-1 via auto- or trans-phosphorylation.

To study the role of Raf-1 in the transduction of downstream signals it is necessary not only to understand its regulation, but also to know its targets. Despite intensive efforts, the only well defined physiological substrate of Raf-1 to date is MEK (31–34). A recent report has shown that Raf-1 also phosphorylates the phosphatase cdc25A, a cell cycle regulator, and that phosphorylation enhances the cdc25A phosphatase activity in vitro (34). In addition, Raf-1 was found to phosphorylate Bad, a pro-apoptotic Bcl-2 family member, and may inhibit Bad-induced apoptosis (35). However, whether cdc25A and Bad can function as physiological downstream effectors of Raf-1 remains unclear.

The present invention provides a novel Raf-1 interacting protein, Tvl-1, and provides evidence for its role in Raf-1 signaling. Screening a yeast two hybrid cDNA library derived from mouse thymus RNA, for such proteins led to the isolation of a novel ankyrin repeat protein, Tvl-1. Tvl-1 interacts with Raf-1 through its carboxyl-terminal ankyrin repeat domain. Similar to 14-3-3, Tvl-1 also forms oligomers. However, in contrast to 14-3-3, Tvl-1 is phosphorylated by Raf-1. Co-expression of Raf-1, Src and Ras with Tvl-1 in Sf9 cells induced a reproducible three to fourfold enhancement of Raf-1 activity. These findings indicate that Tvl-1 contributes to the regulation of the Raf-1 kinase, as well as to the transduction of Raf-1 signals.

Additional data presented herein show that Tvl-1 interacts with Mcl-1, Bcl-$X_L$ and Bad. The interaction with Mcl-1 is enhanced following stimulation with TNF-α. These findings prompted us to perform cell fractionation studies which indicated that Tvl-1 mediates cytochrome c release from mitochondria. Cytochrome c release in turn promotes apoptosis.

Tvl-1 binds caspase 9 constitutively. The Tvl-1 protein binds Tpl-2, an anti-apoptotic kinase and Akt, a proapoptotic kinase and is phosphorylated by both. When Tvl-1 is co-expressed with active Tpl-2, Tvl-1 binds caspase-3 conditionally. These findings taken together indicate that Tvl-1 plays a pivotal role in the assembly of the caspase9/3 activation complex and the activation of caspase 3. Indeed, overexpression of Tvl-1 promotes TNF-induced activation of caspase-3 and apoptosis.

Several findings presented herein also demonstrate that Tvl-1 is a regulator of cell cycle progression. The protein is expressed in both the nucleus and the cytoplasm. Tvl-1 interacts with all of the D-type cyclins and its expression pattern is altered as cells progress through the cell cycle. Finally, the protein is a substrate of cdk kinases.

In light of all the foregoing, it is clear that Tvl-1 provides a novel target for the development new therapeutic agents that may be used to advantage to treat proliferative cell disorders including, but not limited, to cancer.

I. Preparation of Tvl-1-Encoding Nucleic Acid Molecules, Tvl-1 Proteins, and Antibodies Thereto A. Nucleic Acid Molecules Nucleic acid molecules encoding the Tvl-1 proteins of the invention may be prepared by two general methods: (1) synthesis from appropriate nucleotide triphosphates, or (2) isolation from biological sources. Both methods utilize protocols well known in the art. The availability of nucleotide sequence information, such as a cDNA having Sequence I.D. Nos. 1 enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a Tvl-1 encoding double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire Tvl-1 encoding double-stranded molecule. A synthetic DNA molecule so constructed may then be cloned and amplified in an appropriate vector.

Nucleic acid sequences encoding Tvl-1 proteins may be isolated from appropriate biological sources using methods known in the art. In one embodiment, a cDNA clone is isolated from a cDNA expression library of human origin. In an alternative embodiment, utilizing the sequence information provided by the cDNA sequence, human genomic clones encoding Tvl-1 proteins may be isolated.

Alternatively, cDNA or genomic clones having homology with Tvl-1 may be isolated from other species using oligonucleotide probes corresponding to predetermined sequences within the Tvl-1 encoding nucleic acids.

In accordance with the present invention, nucleic acids having the appropriate level of sequence homology with the protein coding region of Sequence I.D. No. 1 may be identified by using hybridization and washing conditions of appropriate stringency. For example, hybridizations may be performed, according to the method of Sambrook et al., (supra) using a hybridization solution comprising: 5×SSC, 5×Denhardt's reagent, 1.0% SDS, 100 g/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42–65° in 1×SSC and 1% SDS, changing the solution every 30 minutes.

One common formula for calculating the stringency conditions required to achieve hybridization between nucleic acid molecules of a specified sequence homology (Sambrook et al., 1989):

$$T_m = 81.5C + 16.6\text{Log}[Na+] + 0.41(\% G+C) - 0.63(\% \text{formamide}) - 600/\#bp \text{ in duplex}$$

As an illustration of the above formula, using [N+]=[0.368] and 50% formamide, with GC content of 42% and an average probe size of 200 bases, the $T_m$ is 57° C. The $T_m$ of a DNA duplex decreases by 1°–1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

Nucleic acids of the present invention may be maintained as DNA in any convenient cloning vector. In a preferred embodiment, clones are maintained in a plasmid cloning/expression vector, such as pBluescript (Stratagene, La Jolla, Calif.), which is propagated in a suitable *E. coli* host cell.

Tvl-1-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the cDNA having SEQ. ID NO:1. Such oligonucleotides are useful as probes for detecting or isolating Tvl-1 genes. Antisense nucleic acid molecules may be targeted to translation initiation sites and/or splice sites to inhibit the production of the Tvl-1 genes of the invention. Such antisense molecules are typically between 15 and 30 nucleotides length (15-mers and 30-mers) or longer and span the translational start site of Tvl-1 encoding mRNA molecules.

It will be appreciated by persons skilled in the art that variants (e.g., allelic variants) of these sequences exist in the human population, and must be taken into account when designing and/or utilizing oligos of the invention. Accordingly, it is within the scope of the present invention to encompass such variants, with respect to the Tvl-1 sequences disclosed herein or the oligos targeted to specific locations on the respective genes or RNA transcripts. With respect to the inclusion of such variants, the term "natural allelic variants" is used herein to refer to various specific nucleotide sequences and variants thereof that would occur in a given population. The usage of different wobble codons and genetic polymorphisms which give rise to conservative or neutral amino acid substitutions in the encoded protein are examples of such variants. Additionally, the term "substantially complementary" refers to oligo sequences that may not be perfectly matched to a target sequence, but the mismatches do not materially affect the ability of the oligo to hybridize with its target sequence under the conditions described.

B. Proteins

Full-length Tvl-1 proteins of the present invention may be prepared in a variety of ways, according to known methods. The proteins may be purified from appropriate sources, e.g., transformed bacterial or animal cultured cells or tissues, by immunoaffinity purification. However, this is not a preferred method due to the low amount of protein likely to be present in a given cell type at any time. The availability of nucleic acid molecules encoding Tvl-1 proteins enables production of the proteins using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or Gibco-BRL, Gaithersburg, Md.

Alternatively, according to a preferred embodiment, larger quantities of Tvl-1 proteins may be produced by expression in a suitable prokaryotic or eukaryotic system. For example, part or all of a DNA molecule, such as a cDNA having SEQ. ID NO:1 may be inserted into a plasmid vector adapted for expression in a bacterial cell, such as *E. coli*. Such vectors comprise the regulatory elements necessary for expression of the DNA in the host cell (e.g. *E. coli*) positioned in such a manner as to permit expression of the DNA in the host cell. Such regulatory elements required for expression include promoter sequences, transcription initiation sequences and, optionally, enhancer sequences.

The human Tvl-1 proteins produced by gene expression in a recombinant procaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6–8 histidine residues at their N-terminus or C-terminus. Alternative tags may comprise the FLAG epitope or the hemagglutinin epitope. Such methods are commonly used by skilled practitioners.

The Tvl-1 proteins of the invention, prepared by the aforementioned methods, may be analyzed according to standard procedures. For example, such proteins may be subjected to amino acid sequence analysis, according to known methods.

The present invention also provides antibodies capable of immunospecifically binding to proteins of the invention. Polyclonal antibodies directed toward Tvl-1 proteins may be prepared according to standard methods. In a preferred embodiment, monoclonal antibodies are prepared, which react immunospecifically with the various epitopes of the Tvl-1 proteins described herein. Monoclonal antibodies may be prepared according to general methods of Köhler and Milstein, following standard protocols. Polyclonal or monoclonal antibodies that immunospecifically interact with Tvl-1 proteins can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules. Other uses of anti-Tvl-1 antibodies are described below.

II. Uses of Tvl-1-Encoding Nucleic Acids

Tvl-1 Proteins and Antibodies Thereto

Cellular signalling molecules have received a great deal of attention as potential prognostic indicators of neoplastic disease and as targets of therapeutic agents to be used for a variety of purposes in cancer chemotherapy. The Tvl-1 proteins of the invention are intimately involved in the regulation of apoptosis. The biochemical and molecular interactions of the Tvl-1 genes and proteins involved in apoptosis and cell cycle progression provide novel targets for the development of reagents that can be used to advantage to control and/or inhibit these processes.

Additionally, Tvl-1 nucleic acids, proteins and antibodies thereto, according to this invention, may be used as research tools to identify other proteins that are intimately involved in apoptosis and cell cycle progression. Biochemical elucidation of molecular mechanisms which control cell death will facilitate the development of novel anti-mitotic agents that may be used to inhibit the aberrant cellular proliferation of tumor cells.

A. Tvl-1-Encoding Nucleic Acids

Tvl-1-encoding nucleic acids may be used for a variety of purposes in accordance with the present invention. Tvl-1-encoding DNA, RNA, or fragments thereof may be used as probes to detect the presence of and/or expression of genes encoding Tvl-1 proteins. Methods in which Tvl-1-encoding nucleic acids may be utilized as probes for such assays include, but are not limited to: (1) in situ hybridization; (2) Southern hybridization (3) northern hybridization; and (4) assorted amplification reactions such as polymerase chain reactions (PCR).

The Tvl-1-encoding nucleic acids of the invention may also be utilized as probes to identify related genes from other animal species. As is well known in the art, hybridization stringencies may be adjusted to allow hybridization of nucleic acid probes with complementary sequences of varying degrees of homology. Thus, Tvl-1-encoding nucleic acids may be used to advantage to identify and characterize other genes of varying degrees of relation to the Tvl-1 genes of the invention thereby enabling further characterization of the apoptotic cell death pathway. Additionally, they may be used to identify genes encoding proteins that interact with Tvl-1 proteins (e.g., by the "interaction trap" technique), which should further accelerate identification of the components involved in cell cycle progression.

Nucleic acid molecules, or fragments thereof, encoding Tvl-1 genes may also be utilized to control the production of Tvl-1 proteins, thereby regulating the amount of protein available to participate in apoptotic reactions. As mentioned above, antisense oligonucleotides corresponding to essential processing sites in Tvl-1-encoding mRNA molecules may be utilized to inhibit Tvl-1 protein production in targeted cells. Alterations in the physiological amount of Tvl-1 proteins may dramatically affect the activity of other protein factors involved in the regulation of cell cycle progression and programmed cell death.

The availability of Tvl-1 encoding nucleic acids enables the production of strains of laboratory mice carrying part or all of the Tvl-1 genes or mutated sequences thereof. Such mice may provide an in vivo model for cancer. Alternatively, the Tvl-1 nucleic acid sequence information provided herein enables the production of knockout mice in which the endogenous gene encoding Tvl-1 have been specifically inactivated. Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo. Production of the transgenic mice described above will facilitate the molecular elucidation of the role Tvl-1 proteins play during embryonic development.

As described above, Tvl-1-encoding nucleic acids are also used to advantage to produce large quantities of substantially pure Tvl-1 proteins, or selected portions thereof.

B. Tvl-1 Proteins and Antibodies

Purified Tvl-1 proteins, or fragments thereof, may be used to produce polyclonal or monoclonal antibodies which also may serve as sensitive detection reagents for the presence and accumulation of Tvl-1 proteins (or complexes containing Tvl-1 proteins) in mammalian cells. Recombinant techniques enable expression of fusion proteins containing part or all of Tvl-1 proteins. The full length proteins or fragments of the proteins may be used to advantage to generate an array of monoclonal antibodies specific for various epitopes of Tvl-1 proteins, thereby providing even greater sensitivity for detection of Tvl-1 proteins in cells.

Polyclonal or monoclonal antibodies immunologically specific for Tvl-1 proteins may be used in a variety of assays designed to detect and quantitate the proteins. Such assays include, but are not limited to: (1) flow cytometric analysis; (2) immunochemical localization of Tvl-1 proteins in tumor cells; and (3) immunoblot analysis (e.g., dot blot, Western blot) of extracts from various cells. Additionally, as described above, anti-Tvl-1 antibodies can be used for purification of Tvl-1 proteins and any associated subunits (e.g., affinity column purification, immunoprecipitation).

From the foregoing discussion, it can be seen that Tvl-1-encoding nucleic acids, Tvl-1 expressing vectors, Tvl-1 proteins and anti-Tvl-1 antibodies of the invention can be used to detect Tvl-1 gene expression and alter Tvl-1 protein accumulation for purposes of assessing the genetic and protein interactions involved in the cell cycle progression and apoptotic cell death.

The examples presented below are provided to illustrate certain embodiments of the invention. They are not intended to limit the invention in any way. The following protocols were utilized in practicing the methods of the present invention.

Yeast Interaction Trap

The open reading frame of human Raf-1 (from D. Morrison) was inserted into the pEG202 vector so as to be expressed as a fusion with the DNA binding domain of LexA, a bacterial transcriptional repressor (36). A murine CD4$^+$ T cell cDNA library (from Stratagene) was subcloned into the expression vector pJG4-5, which utilizes the galactose-inducible GAL-1 promoter to express library clones as fusions to a nuclear localization sequence, a portable transcriptional activation domain (the "acid blob", B42), and a hemagglutinin epitope tag (37). Bait and library plasmids were transformed into the yeast strain EGY48/pSH18-34, in which the upstream regulatory elements of the chromosomal LEU2 gene have been replaced by three copies of the LexA operator and which carries the reporter plasmid SH18-34 containing the LacZ gene also under the control of LexA operators. Clones interacting with Raf were isolated based on their activation of the LEU2 and LacZ reporters, which enabled cells to grow and form blue colonies in leucine-free, X-gal containing medium.

The specificity of the interaction between Tvl-1 and Raf-1 was further characterized in a yeast interaction mating assay as described (38, 39). Briefly, EGY48 (MAT) haploid cells harboring the plasmid expressing the acid blob-Tvl-1 were mated with a panel of haploid RFY206 (MAT a) cells harboring constructs encoding LexA-fusion proteins. Besides LexA-Raf-1, the LexA-fusions included the constitutively active Raf-1 mutant, Raf-1 Y340D, the amino terminal 330 amino acids of Raf-1, and 27 other proteins that function in pathways regulating cell proliferation. As in the interaction trap screening procedure, an interaction was scored as positive when the resulting diploid cells were able to grow on medium lacking leucine and activate LexAop-LacZ reporters.

RNA Isolation, Northern Blotting and cDNA Libraries

Poly A(+) RNA was isolated using the method of Chomczynski and Sacci (40). Northern blots were generated and hybridized with the partial Tvl-1 cDNA probe cloned from the interaction trap library. The same probe was used to screen a murine CD4 positive T cell cDNA library (Stratagene) and a cDNA library from the rat spleen, constructed by us. The rat spleen cDNA library was constructed from poly A+ RNA using the Stratagene cDNA cloning kit according to the protocol provided by the manufacturer.

Mammalian Cell Lines and Transfections

COS-1 and CV1 were obtained from the ATCC and maintained in Dulbecco's modified Eagle's medium (DMEM) supplemented with 10% fetal bovine serum (FBS) and penicillin (50 units/ml), streptomycin (50 $\mu$g/ml), and kanamycin (100 $\mu$g/ml) (PSK). NIH 3T3 cells were also maintained in DMEM supplemented with 10% calf serum (CS), and PSK. NB2, a prolactin dependent rat T cell lymphoma line was provided by P. Gout (University of British Columbia). NB2 cells were grown in RPMI 1640 media supplemented with FBS (10%) and PSK. COS-1 cells were transiently transfected by the DEAE-dextran/chloroquine method as described previously (41). NIH 3T3 cells were transfected using Lipofectamine (GIBCO/BRL) according to the manufacturer's protocol.

Expression Constructs pCMV5-Tvl-1 was generated by inserting the full-length cDNA of Tvl-1 as an EcoRI/XhoI fragment into the EcoRI/Sal I sites of pCMV5 (42). A FLAG epitope tagged Tvl-1 construct, FLAG-Tvl-1, and a hemagglutinin (HA) epitope tagged construct, HA-Tvl-1 were generated by inserting the Tvl-1 coding sequence in frame with the FLAG or the HA epitope tag into the CMV-5 expression vector. A series of truncated Tvl-1 expression vectors were constructed by putting the FLAG-tagged truncated cDNA fragments of Tvl-1 (amplified by PCR) into a pCDNA3 expression vector (Invitrogen). A Raf-1 expression construct was generated by inserting the wild type or constitutively active Y340D mutant Raf-1 cDNA (7).

Baculoviruses expressing Tvl-1, the constitutively active Raf-1 mutant Y340D, and the kinase-negative Raf-1 mutant K375M were generated by ligating the appropriate inserts into the transfer vector pVL1393 (PharMingen), and transfecting the resulting constructs into Sf9 cells using the Baculogold Transfection Kit (PharMingen). Baculoviruses expressing Raf-1, v-src and v-HA-ras were provided by Dr. J. Chernoff (Fox Chase Cancer Center).

Antibodies

Rabbits were inoculated with (His)6-tagged Tvl-1 protein purified from E. coli strain M15 (Qiagen) transformed with the construct pQE30-Tvl-1. pQE30-Tvl-1 was constructed by inserting the coding sequence of the full length Tvl-1 cDNA into the bacterial expression vector pQE30 (Qiagen). E. coli transformed this construct were grown at 37° C. in the presence of ampicillin (50 g/ml) and kanamycin (25 g/ml) to $OD_{600}$=0.7. Protein production was induced by growing cells in 0.5 mM IPTG at 25° C. for 5 h. Bacteria were collected, resuspended in 10 mM Tris (pH 7.6), 0.5 M NaCl, 0.1% NP-40, 10% glycerol, 4 mM dithiothreitol (DTT), 1 mM phenyl-methyl-sulfonyl-fluoride (PMSF) and lysed by sonication on ice. His-tagged proteins were collected by incubating the clarified lysate with $Ni^{2+}$-NTA resin (Qiagen), washed with lysis buffer containing 25 mM imidazole and eluted by 100 mM Imidazole. His-tagged Tvl-1 isolated by this procedure was shown to be at least 85% pure as determined by Coomassie Brilliant blue staining of eluted proteins separated by SDS-polyacrylamide gel electrophoresis (PAGE). Tvl-1 proteins were excised from the gel and were inoculated into rabbits. A second rabbit polyclonal antibody was raised against an Tvl-1-derived multiple antigen peptide (a.a. 100–113) (synthesized by Research Genetics Inc., Huntsville, Ala.) according to standard protocols.

Rabbit polyclonal antibody against the carboxyl-terminus of Raf-1(C12) was purchased from Santa Cruz Biotechnologies. A Raf-1 monoclonal antibody was purchased from Transduction Labs. The M2 anti-FLAG monoclonal antibody was purchased from Kodak IBI. Anti-HA mouse monoclonal antibody 12CA5 was purchased from Babco.

Immunoprecipitations and Western Blotting

Cultured cells were lysed in NP-40-lysis buffer (20 mM Hepes, pH 7.6, 137 mM NaCl, 0.5% NP-40, 2 mM EGTA, 10% glycerol, 5 g/ml leupeptin, 5 g/ml aprotinin, 1 mM PMSF, 5 mM NaF, 1 mM sodium vanadate). Cell lysates were clarified by centrifugation at 4° C. for 10 min at 12,000×g and were precleared by a 30 minute incubation with protein A agarose beads (Gibco-BRL). Immunoprecipitations were carried out by incubating these lysates with the appropriate antibodies for 3 hours. The resulting antigen-antibody complexes were collected with protein A or protein G agarose beads. The immunoprecipitates were then washed three to four times with cold NP-40 lysis buffer before analysis by SDS-PAGE.

Western blots of the immunoprecipitates or of total cell lysates were carried out using Immobilon-P membranes (Millipore) and the enhanced chemiluminescence detection system (Amersham).

Immunofluorescence

NIH 3T3 cells seeded on glass coverslips were transfected with pCMV5-FLAG-Tvl-1 using lipofectamine (Gibco BRL). Thirty-six hours after transfection, the cells were then washed twice with phosphate buffered saline (PBS), fixed with 3.7% paraformaldehyde (pH 7.4), and permeabilized with 0.1% Triton X-100 in PBS. To block non-specific antibody binding, the cells were incubated in 10% goat serum in PBS for 60 minutes at room temperature, prior to being incubated for 60 minutes with the M2 mouse monoclonal anti-FLAG antibody or the rabbit anti-Tvl-1 antiserum (1:400 dilution in 5% goat serum). After washing with PBS, cells were incubated for 30 min with FITC-conjugated goat anti-mouse or anti-rabbit antibodies (diluted 1:400) plus 1 μg/ml bisbenzimid (Hoechst 33258). Coverslips were finally washed twice in PBS and mounted on glass slides with anti-fade medium (90% glycerol with 1 mg/ml paraphenylene diamine). Fluorescence was recorded in the Fox Chase Confocal Microscopy Imaging Facility.

In Vitro Protein Kinase Assays

Raf-1 kinase assays were performed using standard procedures (32, 43). Briefly, $2\times10^6$ Sf9 cells in 60 mm petri dishes were infected with the desired combination of baculoviruses. After 48 hours, cells were washed twice in cold PBS and lysed in the NP-40 lysis buffer or in RIPA buffer (20 mM Tris, pH 8.0, 137 mM NaCl, 10% glycerol, 1% NP-40, 0.1% SDS, 0.5% sodium deoxycholate, 2 mM EDTA, 1 mM PMSF, 2 μg/ml aprotin/leupeptin, 5 mM NaF, and 5 mM sodium vanadate). Insoluble material was removed by centrifugation at 16,000 g for 10 min at 4° C., and clarified lysates were incubated with rabbit anti-Raf antibody (C12, Santa Cruz Biotechnology or X, Transduction Labs) for 3 hours at 4° C., followed by collection of the antigen-antibody complexes with protein A agarose beads for 1 h at 4° C. Immunoprecipitates were washed twice with NP-40 lysis buffer, then twice with kinase buffer containing 30 mM Hepes (N-2-hydroxyethylpiperazine-N'-2-ethanesulfonic acid; pH 7.5), 5 mM $MgCl_2$, 5 mM $MnCl_2$, and 1 mM DTT. Kinase reactions were carried out by incubation of the immune complexes for 20 min at 25° C. in 40 μl Raf-1 kinase buffer containing 10 μM unlabeled ATP, 10 μCi ($-^{32}$P)-ATP (Amersham) and 0.2 g of purified recombinant His-tagged Tvl-1 proteins or His-tagged kinase inactive MEK, His-MEK($K^-$). His-MEK($K^+$) in pRSET vector (Invitrogen) was transformed into E. coli BL21(DE). Recombinant His-MEK($K^-$) proteins were prepared by the method described in Gardner et al. (44). No recombinant substrate was added in co-immunoprecipitations of Raf-1 with Tvl-1 from Sf9 cells co-infected with Tvl-1 and Raf-1 baculoviruses. Kinase reactions were stopped by adding SDS sample buffer (120 mM Tris-HCl pH 6.8, 100 mM dithiothreitol, 3% SDS, 10% glycerol, 0.02% bromophenol blue). The products of the kinase reactions were then resolved by SDS-PAGE, blotted onto Immobilon-P membranes (Milipore), and visualized by autoradiography.

EXAMPLE I

Molecular and Biochemical Characterization of TVL-1

Interaction Trap and Interaction Mating Assays Identify a Ubiquitously Expressed Ankyrin Repeat Protein, Tvl-1, that specifically Binds Raf-1

To identify novel proteins that may interact with Raf-1 we screened a $CD4^+$ murine T cell cDNA library using the interaction trap two hybrid system in the yeast Saccharomyces cerevisiae, as described by Gyuris et al. (37). Out of fifty isolated clones, fifteen were sequenced and they were found to be derived from a single gene Tvl-1 (data not shown).

Shown in FIG. 1 is an experimental demonstration of Tvl-1 interaction with Raf-1 in the yeast two-hybrid system. (A) B42 Tvl-1 interacts with LexA fusions of Raf-1 (#1), Raf-1 Y340D (#3) and, less efficiently, with Raf-1(1–330) (#4). However, it fails to interact with the acid blob B42 (#2). The observed interactions occurred only in the presence of galactose.

Thus, the specificity of interaction of the B42-Tvl-1 fusion with Raf-1 was confirmed by the experiment in FIG. 1 which shows that growth is galactose and therefore B42-Tvl-1-dependent and that Raf-1 interacts with B42-Tvl-1 but not with the B42 domain alone. The same figure shows that Tvl-1 also interacts with the amino-terminal domain of Raf-1 (a.a. 1–330). However, the efficiency of this interaction is very low, suggesting that Raf-1 interacts with Tvl-1 primarily via its carboxy-terminal catalytic portion.

To determine whether Tvl-1 interacts with other signaling proteins we carried out interaction mating experiments (38, 39) between EGY48 MAT haploid cells harboring the construct encoding the fusion protein B42 Tvl-1 and a panel of twenty-six RFY206 MAT ahaploid cells harboring constructs encoding LexA-fusion proteins. The results showed that Tvl-1 does not interact with cdc2 (cdk1), cdk2, c-Ha-ras, c-Ha-rasC186A, Rb, ftz, SSN6, CD11, daughterless, goosecoid, CDK3, CDI7, CDI11, DMcdc2, LAR, cyclin C, cyclin E, CLN3, hairy, MYC, MAX, Mxi-1, p53, thyroid hormone receptor, bicoid, and a synthetic polyglutamine peptide (data not shown). These results indicated that the interaction of Tvl-1 with Raf-1 is specific.

FIG. 2 is presented to show that Tvl-1 is widely expressed and encodes a novel ankyrin repeat protein. GenBank accession number, L43164. (A) Upper panel: Northern blot analysis of 5 μg of poly A(+) RNA isolated from the indicated normal adult mouse tissues. Lower panel: Profile of Ethidium bromide gel of the Northern blot. (B) Western blot of total cell lysates from normal mouse tissues probed with a polyclonal rabbit antiserum raised against bacterially expressed His-tagged-Tvl-1 protein. (C) Amino acid sequence of the murine Tvl-1 protein deduced from the nucleotide sequence of clone 19 isolated from a murine CD4$^+$ T cell cDNA library (Stratagene), SEQ ID NO:2. The underlined sequence defines the ankyrin repeat region. The boxed sequence starting at amino acid 112 is absent from 50% of the cDNA clones. The difference between the two cDNAs is the result of differential splicing. (D) Alignment of the four ankyrin repeats (1$^{st}$ ankyrin repeat (AKR), RGFTPLIWASAFGEIETVRFLLDWGADPHILAK, SEQ ID NO:3; 2$^{nd}$ AKR, ERESALSLASMGGYTDIVRLLLDRDVDINIYDW, SEQ ID NO:4; 3$^{rd}$ AKR, NGGTPLLYAVRGNHVKCVEALLARGADLTTEAD, SEQ ID NO:5; and 4$^{th}$ AKR, SGYTPMDLAVALGYRKVQQVMESHILRLFQSTL, SEQ ID NO:6) detected in the C-terminal portion of Tvl-1 with the consensus ankyrin repeat(-G-TPLHLAAR-GHVEVVKLLLD-GADVNA-TK, SEQ ID NO:7; SA I SQ NNLDIAEV K NPD D, SEQ ID NO:8; V K T M R Q SI A, SEQ ID NO:9). The consensus is that deduced via the alignment of the ankyrin repeats of brain ankyrin B (51, 52). The Tvl-1 protein encoded by the differentially spliced mRNA contains a 5th ankyrin repeat (i.e., conditional AKR, DSLSIHQLAAQGELSQLKDHLRKGNNLINKPDE, SEQ ID NO:10) motif that is located upstream of the first one and is generated as a result of the 10 amino acid deletion boxed in C.

Figure 2A:
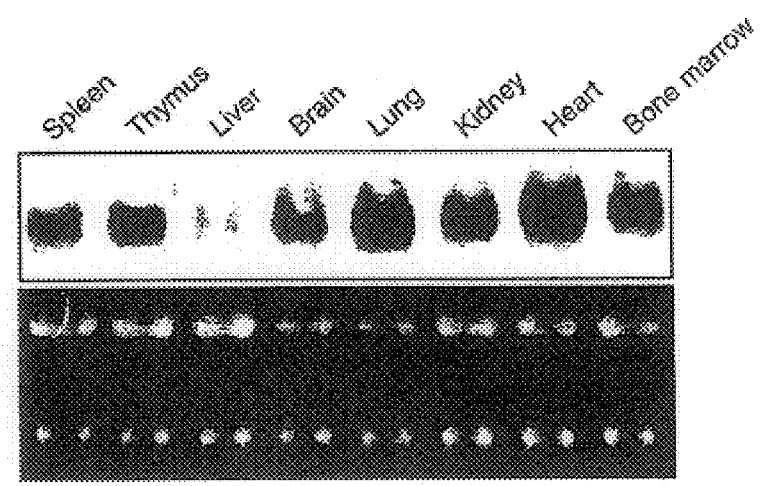
FIG. 2 shows that Tvl-1 is widely expressed and encodes a novel ankyrin repeat protein. (A) Upper panel: Northern blot analysis of 5 µg of poly A(+) RNA isolated from the indicated normal adult mouse tissues. Lowerpanel: Profile of Ethidium bromide gel of the Northern blot. (B) Western blot of total cell lysates from normal mouse tissues probed with a polyclonal rabbit antiserum raised against bacterially expressed His-tagged-Tvl-1 protein. (C) Amino acid sequence of the murine Tvl-1 protein deduced from the nucleotide sequence of clone 19 isolated from a murine CD4$^+$ T cell cDNA library (Stratagene), SEQ ID NO:2. The underlined sequence defines the ankyrin repeat region. The boxed sequence starting at amino acid 112 is absent from 50% of the cDNA clones. The difference between the two cDNAs is the result of differential splicing. (D) Alignment of the four ankyrin repeats detected in the C-terminal portion of Tvl-1. The consensus ANK repeat sequence is that deduced via the alignment of the ankyrin repeats of brain ankyrin B (51, 52). The Tvl-1 protein encoded by the differentially spliced mRNA contains a 5th ankyrin repeat (conditional AKR) motif that is located upstream of the first one and is generated as a result of the 10 amino acid deletion boxed in C.
Figure 2B:
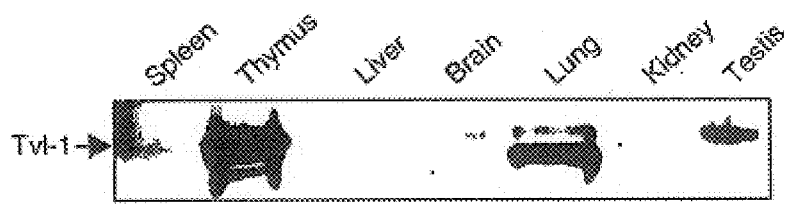

Hybridization of an Tvl-1-specific cDNA probe to a Northern blot of poly A(+) RNA from normal adult mouse tissues revealed that Tvl-1 mRNA is widely expressed (FIG. 2A). Western blots of lysates from normal adult mouse tissues probed with an Tvl-1-specific antibody raised against bacterially expressed Tvl-1 protein (FIG. 2B, Materials and Methods) revealed that Tvl-1 is expressed primarily in thymus, lung and testes. The levels of Tvl-1mRNA and protein in different tissues correlate only partially, suggesting that protein expression of Tvl-1 may be regulated in part at the posttranscriptional level.

Sequencing of full length cDNA clones obtained by screening a murine CD4$^+$ T cell cDNA library revealed that Tvl-1 encodes a novel 269 amino acid protein containing four ankyrin repeats at the carboxyterminus (FIG. 2C and 2D). Some of the cDNA clones contain a small internal deletion. These clones represent a differentially spliced mRNA species that, when translated, is expected to give rise to a short Tvl-1 protein (deletion marked by box in FIG. 2C). Deletion of the indicated 10 amino acids generates a 5th ankyrin repeat motif that is located upstream of the first one (FIG. 2C). Since both the long and short forms of Tvl-1 interact with Raf-1, the significance of the two forms is currently unknown. Sequencing a full length cDNA clone isolated from a rat spleen CDNA library showed that the mouse and rat genes exhibit 95% identity at the amino acid level. Screening existing databases for Tvl-1-related sequences identified two overlapping human cosmid clones (R2770 and F14150) which map to human chromosome 19p12 and contain the entire sequence of the human Tvl-1 homolog (Accession Number: AC002126 and AC003110). The same clone contains a myocyte enhancer binding factor MEF2B (47, 48) at a distance of about 0.7 kb upstream of Tvl-1 in a head to head orientation with Tvl-1.

The Tvl-1 clones isolated from the two hybrid cDNA library encode protein fusions between the C-terminal two thirds of Tvl-1 (a.a. 81–269) and the activation domain B42. Following cloning of the full length Tvl-1 gene, we showed that while the full length protein also interacts with Raf-1, its N-terminal portion (a.a. 1–96) of Tvl-1 does not (data not shown). Therefore, the interaction between the two proteins is mediated by the carboxyterminal domain of Tvl-1.

Tvl-1 Co-immunoprecipitates with Raf-1—FIG. 3 is presented to show that Tvl-1 interacts with Raf-1. (A) COS-1 cells were transfected with FLAG-tagged Tvl-1, wild-type Raf-1 and constitutively active Raf-1 (Y340D) in the vector pCMV5. Cells were lysed 48 h later, and FLAG-Tvl-1 was immunoprecipitated with the anti-FLAG M2 monoclonal antibody (lanes 1 to 3). Raf-1 and Flag-Tvl-1 were detected in the immunoprecipitates by Western blotting using rabbit anti-raf antiserum (C12; upper part) and rabbit anti-Tvl-1 antiserum raised against the whole recombinant Tvl-1 protein. COS-1 cell lysates were also immunoprecipitated with the anti-raf C12 antibody and, following Western blotting, they were probed with the same anti-raf and anti-Tvl-1 antibodies (lanes 4 to 6). (B) Mapping the Tvl-1 domain that interacts with Raf-1. Upper panel: Schematic representations of FLAG-tagged Tvl-1 deletion mutants. Lower panel: Co-immunoprecipitation of Raf-1 and Tvl-1 deletion mutants in COS-1 cells transfected with the indicated expression constructs.

Figure 3A:
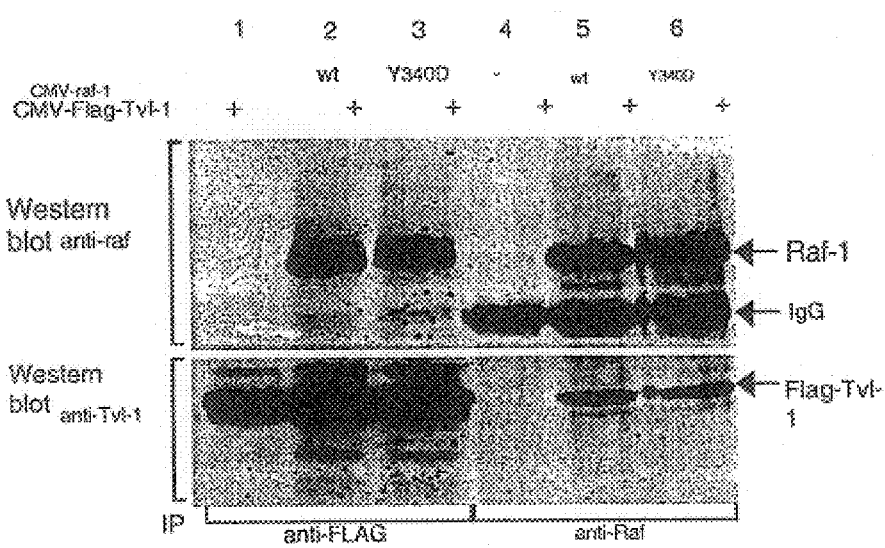
FIG. 3 depicts that Tvl-1 interacts with Raf-1. (A) COS-1 cells were transfected with FLAG-tagged Tvl-1, wild-type Raf-1 (wt) and constitutively active Raf-1 (Y340D) in the vector pCMV5. Cells were lysed 48 h later, and FLAG-Tvl-1 was immunoprecipitated with the anti-FLAG M2 monoclonal antibody (lanes 1 to 3). Raf-1 and Flag-Tvl-1 were detected in the immunoprecipitates by Western blotting using rabbit anti-raf antiserum (C12) (upper part) and rabbit anti-Tvl-1 antiserum raised against the whole recombinant Tvl-1 protein. COS-1 cell lysates were also immunoprecipitated with the anti-raf C12 antibody and, following Western blotting, they were probed with the same anti-raf and anti-Tvl-1 antibodies (lanes 4 to 6). (B) Mapping the Tvl-1 domain that interacts with Raf-1. Upper panel: Schematic representations of FLAG-tagged Tvl-1 deletion mutants. Lower panel: Co-immunoprecipitation of Raf-1 and Tvl-1 deletion mutants in COS-1 cells transfected with the indicated expression constructs.
Figure 3B:
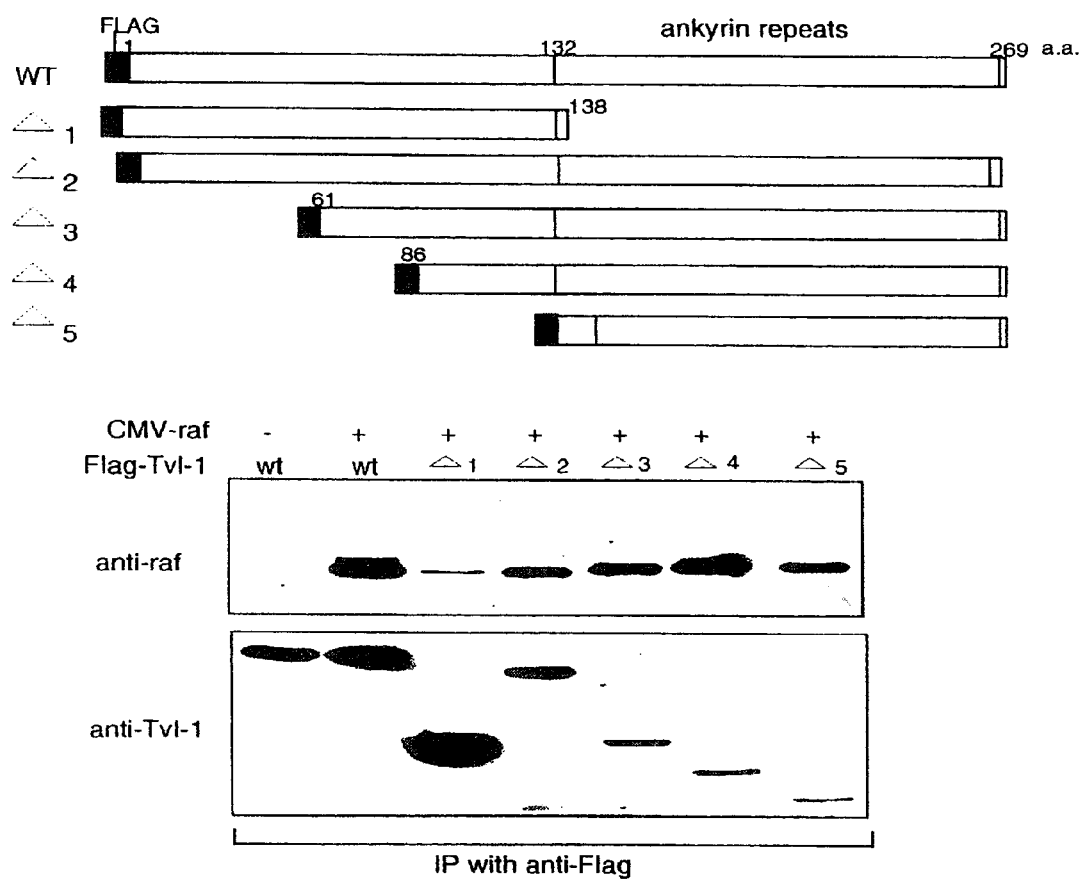

To determine whether Tvl-1 interacts with Raf-1 in mammalian cells, expression constructs of Tvl-1 tagged at their amino-terminus with a FLAG epitope tag (FLAG Tvl-1) and wild type Raf-1 or activated Raf-1 (Y340D) were cotransfected into COS-1 cells in the combinations shown in FIG. 3A. Forty-eight hours later, Raf-1 or Tvl-1 were immunoprecipitated from NP-40 lysates of the transfected COS-1 cells, with anti-FLAG or anti-Raf antibodies. Coprecipitating proteins were detected by probing Western blots of the immunoprecipitates with anti-Raf-1 or anti-Tvl-1 antibodies respectively (FIG. 3A). The results confirmed that Tvl-1 interacts with both the wild type and activated forms of Raf-1 in mammalian cells (FIG. 3A). Similar experiments with the amino-terminally truncated Raf-1 or v-raf, revealed that these proteins and wild type Raf-1 interact equally well with Tvl-1 (data not shown). Therefore, Tvl-1 interacts primarily with the kinase domain and carboxy-terminal tail of Raf-1. Moreover, since a kinase-dead Raf-1K375M also binds Tvl-1 (data not shown), the interaction between the two proteins is independent of the Raf-1 kinase activity.

To map the Tvl-1 domain that interacts with Raf-1, a series of deletion mutants of Tvl-1 with an aminoterminal FLAG tag were constructed and cloned in the expression vector. Cotransfection of these constructs with Raf-1 in COS-1 cells (FIG. 3B) confirmed the results of the two hybrid experiments by showing that it is indeed the carboxyterminal ankyrin repeat region of Tvl-1 that interacts with Raf-1.

The preceding experiments were carried out using lysates of transiently transfected COS-1 cells that express high levels of both Tvl-1 and Raf-1. To determine whether the two proteins interact also when expressed at physiological levels we immunoprecipitated Raf-1 from NP-40 lysates of CV-1 and NB2 cells, two cell lines that express both proteins. Immunoprecipitations were carried out using an anti-Raf antiserum raised against the Raf-1 peptide C12 (Santa Cruz) or a monoclonal anti-Raf-1 antibody (Transduction Labs). Control immunoprecipitations of the NB2 cell lysates were also carried out using a control antibody against the IL-9 receptor. The immunoprecipitates were subjected to SDS-PAGE, and following Western blotting, they were probed with a rabbit antiserum raised against the full-length Tvl-1 protein. In the NB2 cell experiment Western blots were probed with the anti-Tvl-1 antibody raised against the Tvl-1 peptide (a.a. 100–113) in the presence or absence of excess peptide.

Figure 4:
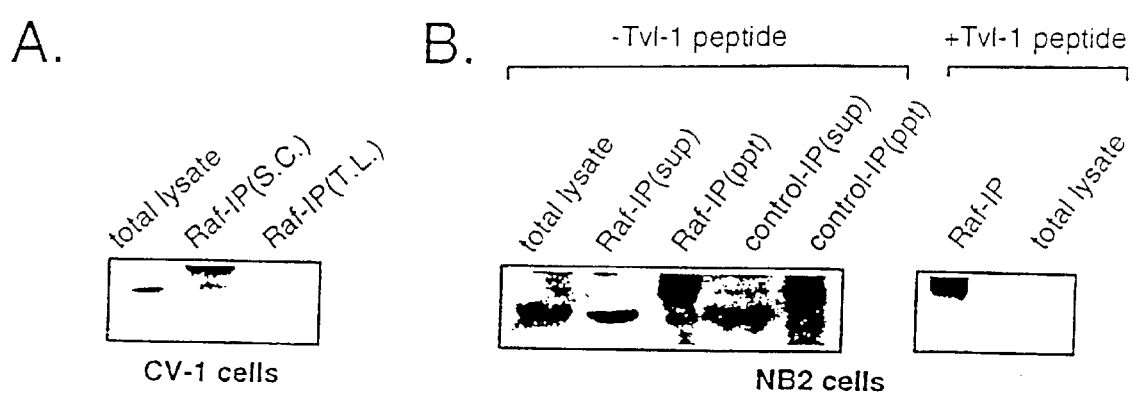
FIG. 4 depicts interaction of endogenous Raf-1 and Tvl-1. Cell lysates of CV-1 (Panel A) or NB2 (panel B) cells were immunoprecipitated using the anti-Raf peptide antiserum (C12) from Santa Cruz (SC) or the anti-Raf-1 monoclonal antibody from Transduction Labs (TL) (Raf-IP) or with a control antibody raised against the IL-9 receptor as indicated (control-IP). Western blot of the resulting immunoprecipitates probed with anti-whole Tvl-1 antiserum (Panel A) or anti-Tvl-1 peptide antiserum (Panel B) revealed a coprecipitating protein band that comigrates with Tvl-1. This band was absent in the IL-9 receptor immunoprecipitate (Panel B, lane 5). The Western blot in panel B was probed with the anti-Tvl-1 peptide antiserum, both in the absence as well as in the presence of excess peptide. The co-immunoprecipitating Tvl-1 band was detected only in the absence of peptide competition.

Shown in FIG. 4 is an immunoblot analysis to show interaction of endogenous Raf-1 and Tvl-1. Cell lysates of CV-1 (Panel A) or NB2 cells (panel B) were immunoprecipitated using the anti-Raf peptide antiserum (C12) from Santa Cruz (SC) or the anti-Raf-1 monoclonal antibody from Transduction Labs (TL) (Raf-IP) or with a control antibody raised against the IL-9 receptor as indicated (control-IP). Western blot of the resulting immunoprecipitates probed with anti-whole Tvl-1 antiserum (Panel A) or anti-Tvl-1 peptide antiserum (Panel B) revealed a coprecipitating protein band that comigrates with Tvl-1. This band was absent in the IL-9 receptor immunoprecipitate (Panel B, lane 5). The Western blot in panel B was probed with the anti-Tvl-1 peptide antiserum, both in the absence as well as in the presence of excess peptide. The co-immunoprecipitating Tvl-1 band was detected only in the absence of peptide competition.

The results (FIGS. 4A and 4B) showed that endogenous Tvl-1 co-immunoprecipitates with endogenously expressed Raf-1 in both CV-1 and NB2 cells.

Tvl-1 Expressed in Transiently Transfected COS-1 Cells Forms Homodimers—Ankyrin repeats form homotypic complexes, as shown in Notch protein (49). To determine whether Tvl-1, an ankyrin repeat protein, homodimerizes, HA-tagged and FLAG-tagged Tvl-1 constructs were cotransfected into COS-1 cells. Forty-eight hours later, Tvl-1 was immunoprecipitated from NP-40 lysates of the transfected cultures by the anti-FLAG antibody M2. Following SDS/PAGE and Western blotting, the resulting immunoprecipitates were probed with the anti-HA antibodies.

Figure 5:
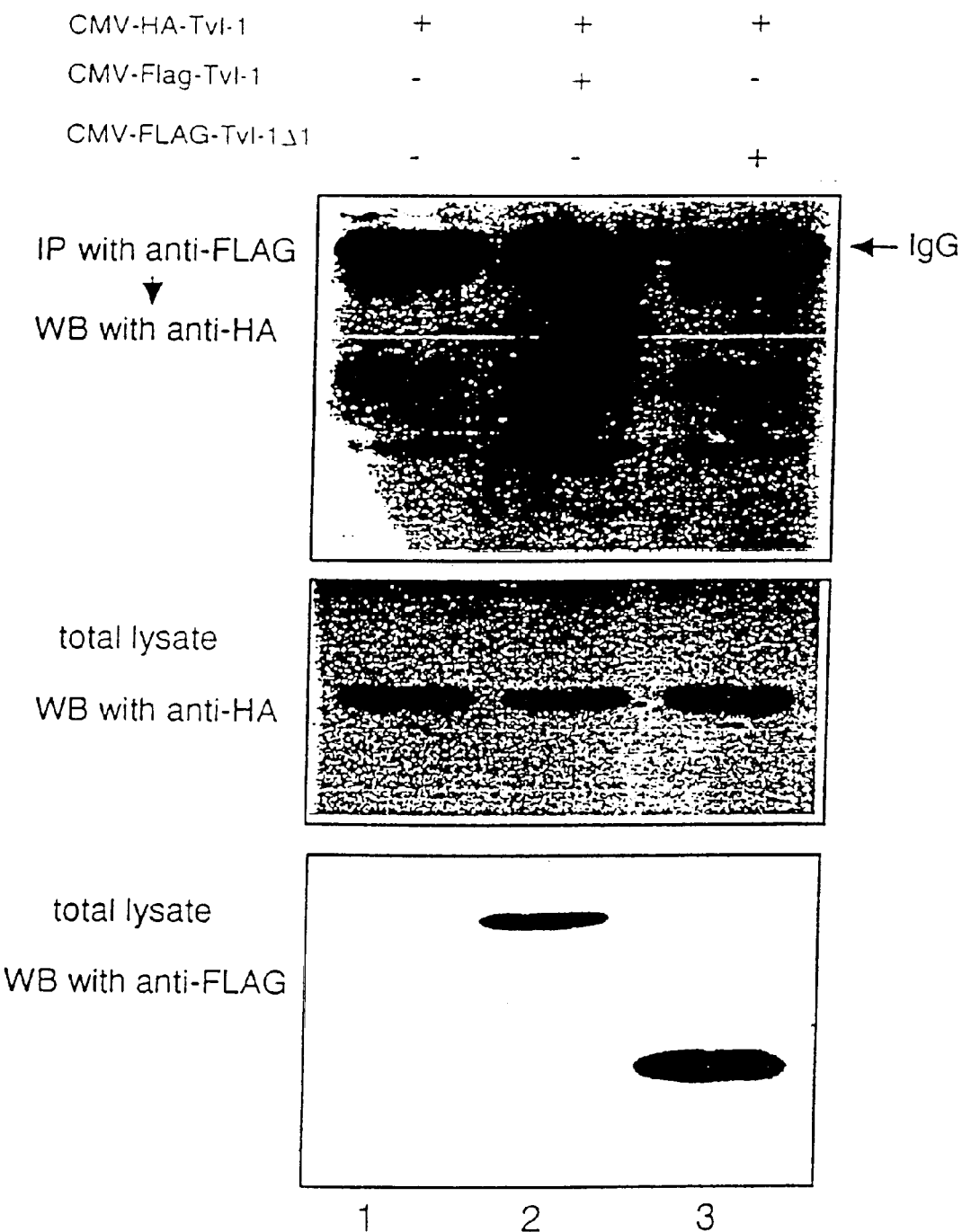
FIG. 5 depicts that Tvl-1 expressed in transiently transfected COS-1 cells homodimerizes itself. COS-1 cells were transfected with HA-tagged wild type Tvl-1 and with FLAG tagged wild type or partially deleted Tvl-1 (FLAG-Tvl-1 D1) constructs at the indicated combinations. Western blots of antixFLAG and antixc-HA immunoprecipitates of transfected cell lysates were probed with the reciprocal antibodies.

FIG. 5 is presented to show that Tvl-1 expressed in transiently transfected COS-1 cells homodimerizes itself. COS-1.cells were transfected with HA-tagged wild type Tvl-1 and with FLAG tagged wild type or partially deleted Tvl-1 (FLAG-Tvl-1 1) constructs at the indicated combinations. Western blots of anti FLAG and anti c-HA immunoprecipitates of transfected cell lysates were probed with the reciprocal antibodies.

The results (FIG. 5A) revealed that Tvl-1 molecules indeed homodimerize. Since HA-Tvl-1 and a FLAG-tagged deletion mutant of Tvl-1 lacking the ankyrin repeat domain do not homodimerize (FIG. 5), we conclude that homodimerization is likely mediated by the ankyrin repeat region.

Subcellular Localization of Tvl-1—To define the subcellular localization of Tvl-1, we transfected NIH 3T3 cells with a FLAG-tagged Tvl-1 construct, either transiently or stably, and we stained the transfected cells with the anti FLAG antibody M2.

Figure 6:
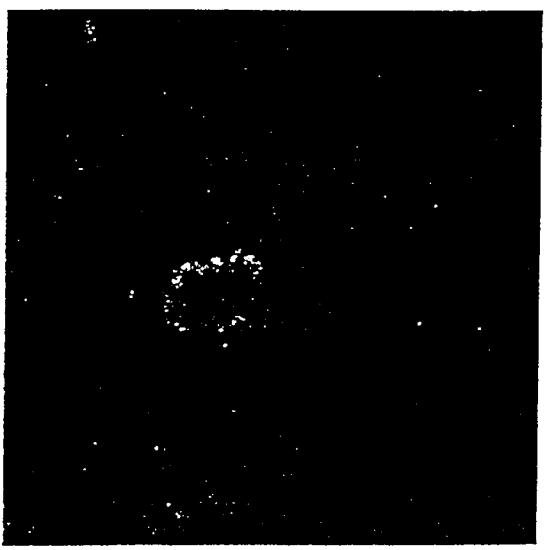
FIG. 6 depicts subcellular localization of Tvl-1. Immunofluorescence of NIH 3T3 cells transfected with a FLAG-tagged Tvl-1 construct and co-stained with the FLAG tag antibody M2 (left pane) and nucleus-staining dye Hoechst 33258 (right panel).
Figure 6:
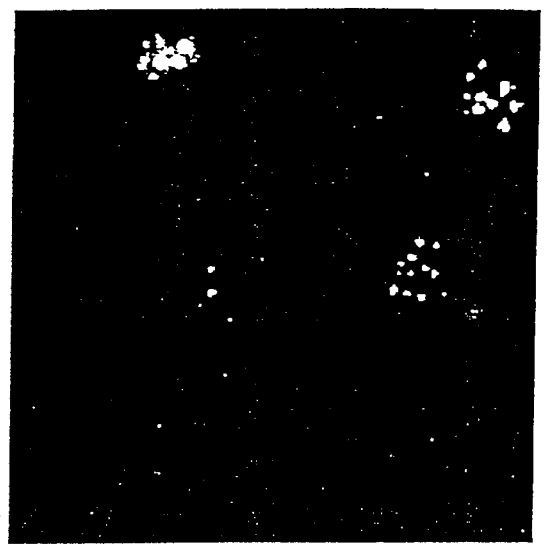

Shown in FIG. 6 is the Subcellular localization of Tvl-1. Immunofluorescence of NIH 3T3 cells transfected with a FLAG-tagged Tvl-1 construct and co-stained with the FLAG tag antibody M2 (left panel) and nucleus-staining dye Hoechst 33258 (right panel).

The results (See FIG. 6) revealed that Tvl-1 is distributed in both the cytoplasm and the nucleus. Similar results were obtained using affinity purified anti-Tvl-1 antibody instead of the FLAG antibody (data not shown). The detection of Tvl-1 in the cytoplasm is compatible with its interaction with Raf-1, a cytoplasmic protein. However, since Tvl-1 is also present in the nucleus, it is likely that it may interact with nuclear proteins and may contribute to the regulation of nuclear functions.

Raf-1 Phosphorylates Tvl-1 in Vitro and in Vivo

To determine whether Tvl-1 serves as a Raf-1 substrate we first carried out in vitro kinase assays using Raf-1 immunoprecipitated from baculovirus-infected Sf9 cells co-expressing Raf-1 and Tvl-1. The kinase inactive mutant Raf-1, K375M, and the activated mutant of Raf-1, Y340D, were used as controls.

Figure 7A:
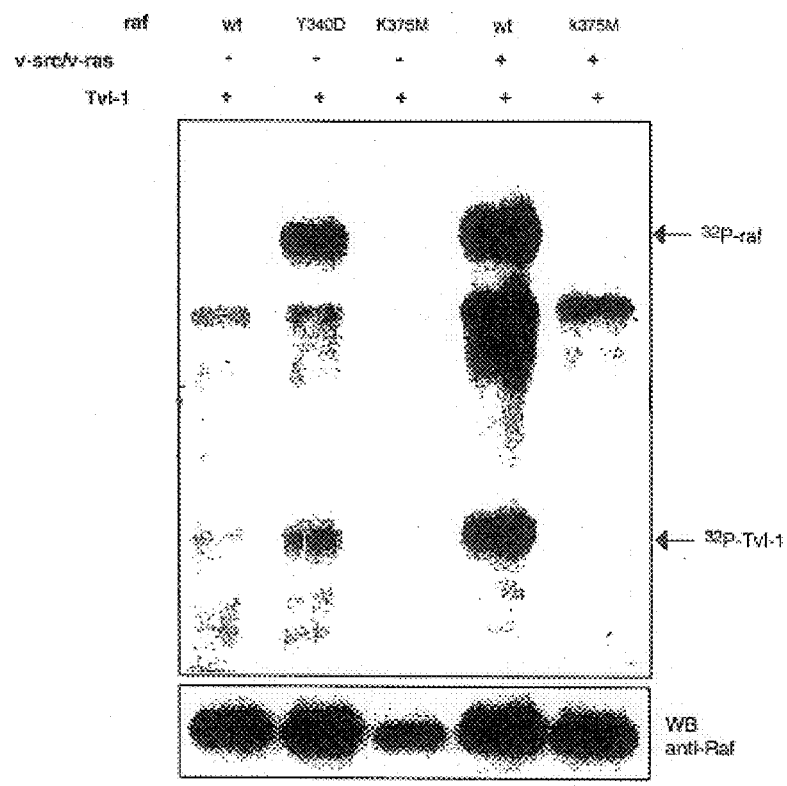
FIG. 7 shows that Tvl-1 is phosphorylated by Raf-1. (A) Upper panel: In vitro kinase assays of Raf-1 also immunoprecipitated from Sf9 cells, infected with baculoviruses directing the expression of wild type and mutant Raf-1, v-src and v-ras as well as Tvl-1 as indicated. The Tvl-1 kinase substrate is not added exogenously in these reactions. Instead it co-immunoprecipitates with Raf-1 from cell lysates expressing both. (A) Lower panel: Raf-1 was expressed approximately equally in all the cultures of Sf9 cells infected with the Raf-1 and Tvl-1 baculoviruses. (B) Upper panel: In vitro kinase assays of Raf-1 immunoprecipitated from lysates of Sf9 cells, infected with baculoviruses directing the expression of Raf-1 (wild type (w.t.), kinase dead (K375M) or constitutively active (Y340D) and v-src and v-ras as indicated. (His)6-Tvl-1 was purified from E. coli transformed with a (His)6-Tvl-1 bacterial expression construct. (B) Lower panel: Western blot of the same Sf9 lysates probed with an anti-Raf-1 antibody.
Figure 7B:
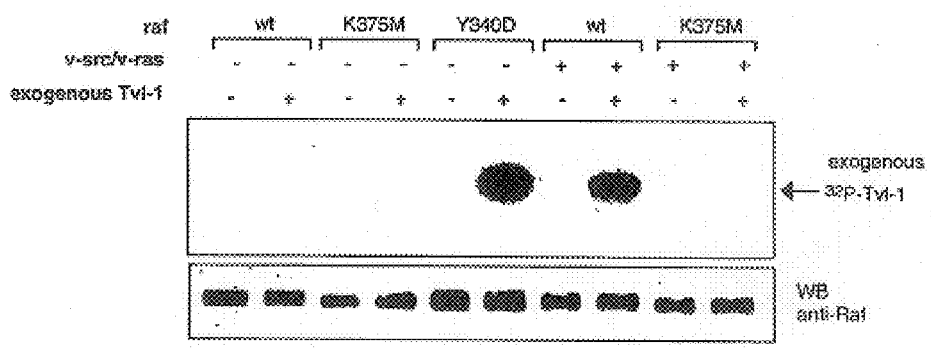

In FIG. 7 it is shown that Tvl-1 is phosphorylated by Raf-1 in vitro. A, upper panel: in vitro kinase assays of Raf-1 immunoprecipitated form Sf9 cells infected with baculoviruses directing the expression of wild type (wt) Raf-1, kinase-dead (K375M) Raf-1 or constitutively active (Y340D) Raf-1, v-Src, and v-Ras as well as Tvl-1 as indicated. Tvl-1 co-immunoprecipitating with Raf-1 was highly phosphorylated only in the lysates derived from cells expressing both active Raf-1 and Tvl-1. Lower panel, Raf-1 was expressed approximately equally in all the baculovirus-infected cultures of Sf9 cells. B, upper panel: in vitro kinase assays of Raf-1 immunoprecipitated from lysates of Sf9 cells, infected with the indicated baculoviruses. Recombinant $(His)_6$-Tvl-1 protein purified from *E. coli* was used as the exogenous kinase substrate. Lower panel, Western blot of the same Sf9 cell lysates probed with the anti-Raf-1 antibody.

Wild type Raf-1 was activated by co-expression of v-Ha-Ras and v-Src (FIG. 7A). In a separate experiment, bacterially expressed $(His)_6$-Tvl-1 was added as the exogenous substrate in Raf-1 in vitro kinase assays. The results in FIG. 7, A and B, revealed that Tvl-1 co-immunoprecipitates with, and is phosphorylated only by catalytically active Raf-1. By comparing the degree of phosphoryltion of Tvl-1 and MEK-1 by Raf-1 in vitro, we found that both proteins served equally well as Raf-1 substrates (data not shown). Inspection of the Tvl-1 sequence revealed a motif S<u>A</u>L<u>S</u>L<u>A</u>SMG<u>G</u> starting at amino acid 168, which is similar to the MEK-1 motif (L/A)-S-(T/S)-G phosphorylated by Raf-1 and represents a candidate phosphorylation site.

To determine whether Raf-1 induces phosphorylation of Tvl-1 in mammalian cells, $^{32}$P-Tvl-1 was immunoprecipitated from ortho [$^{32}$P]phosphate-labeled COS-1 cells expressing Tvl-1 alone or in combination with constitutively active Raf-1 (Y340D). Tvl-1 immunoprecipitated from singly transfected $^{32}$P-labeled cells stimulated with serum for 30 min was used as a control. Immunoprecipitated Tvl-1 was electroblotted onto nitrocellulose membranes, digested with trypsin. The resulting products were separated using a Hunter thin layer peptide mapping electrophoresis apparatus. As shown in FIG. 7C, the tryptic phosphopeptide map of Tvl-1 from COS-1 cells stimulated with serum is very similar, if not identical, to the one from serum-starved COS-1 cells co-expressing Tvl-1 and active Raf-1. These data indicate that Raf-1 indeed phosphorylates Tvl-1 in vivo and is the primary kinase to phosphorylate Tvl-1 in the serum-stimulated cells.

Figure 8:
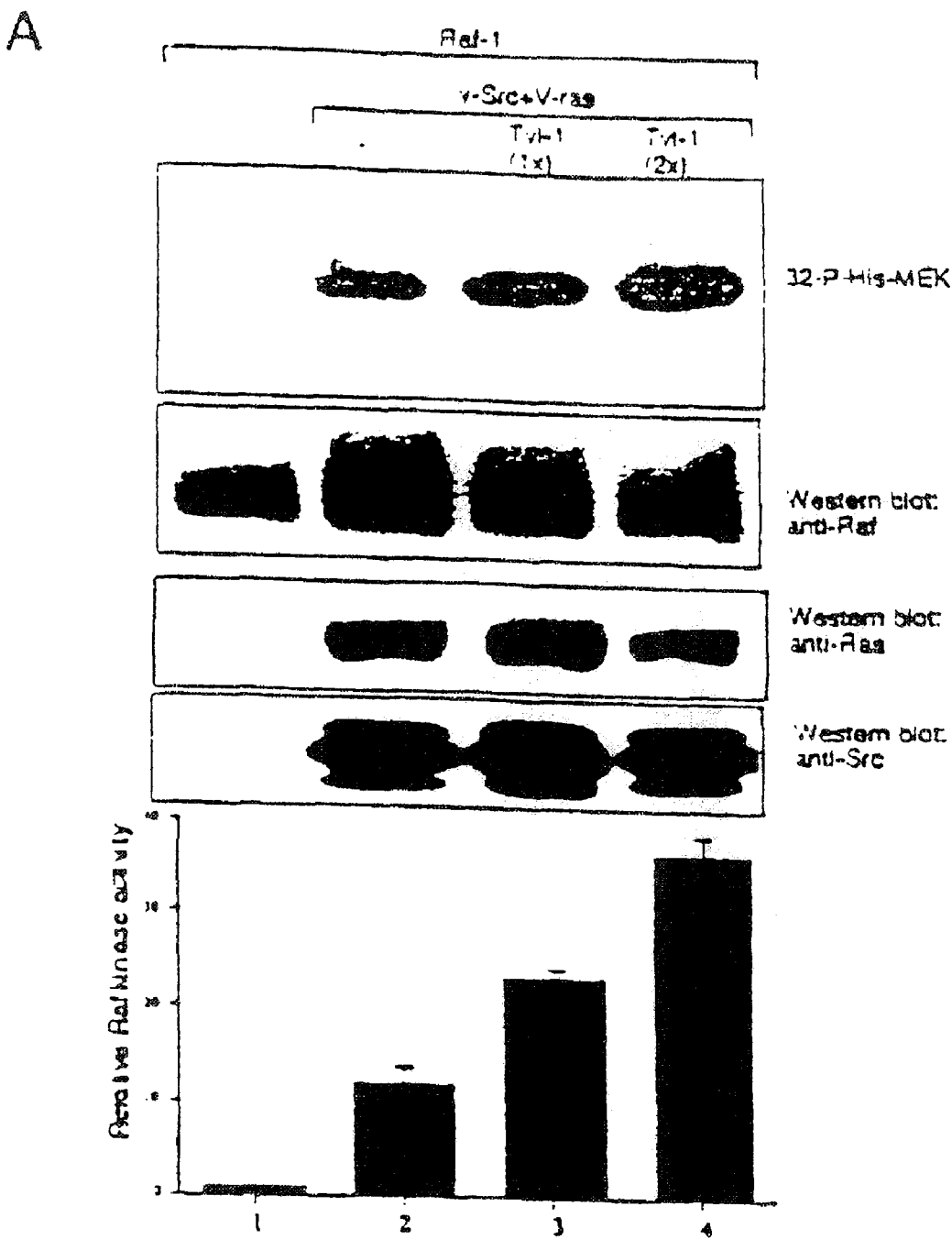
FIG. 8 shows that Tvl-1 enhances the activation of Raf-1 induced by v-Ras/v-Src in Sf9 cells and by EGF in COS-1 cells. (A) Top panel: in vitro kinase reactions were carried out using Raf-1 immunoprecipitated from lysates of Sf9 cells infected with the indicated baculovirus combinations. Bacterially expressed kinase-dead $His_6$-MEK1 was used as the exogenous kinase substrate. (A) Middle panel: Western blot of the total infected cell lysates probed with anti-Raf, anti-Ras, and anti-Src antibodies. (A) Bottom panel: quantitation of the Raf-1 kinase activity from the top panel by PhosphorImager. (B) COS-1 cells were transfected with pEBG (lanes 1 and 2) or pEBG-Raf-1 expression construct (lanes 3–6) alone or in combination with the pMV-FLAG-Tvl-1 expression construct (lanes 4 and 5). Twenty-four hours after transfection, cells were serum-starved overnight, and stimulated with EGF (50 ng/ml) for 20 min. Cells were lysed and GST-Raf-1 was pulled down for kinase assays using recombinant kinase-dead $His_6$-MEK1 as the exogenous substrate (top panel). Total cell lysates were Western blotted and probed with anti-Raf-1 or anti-FLAG antibody (lower two panels). The experiments in both A and B were repeated three times with similar results.
Figure 8:
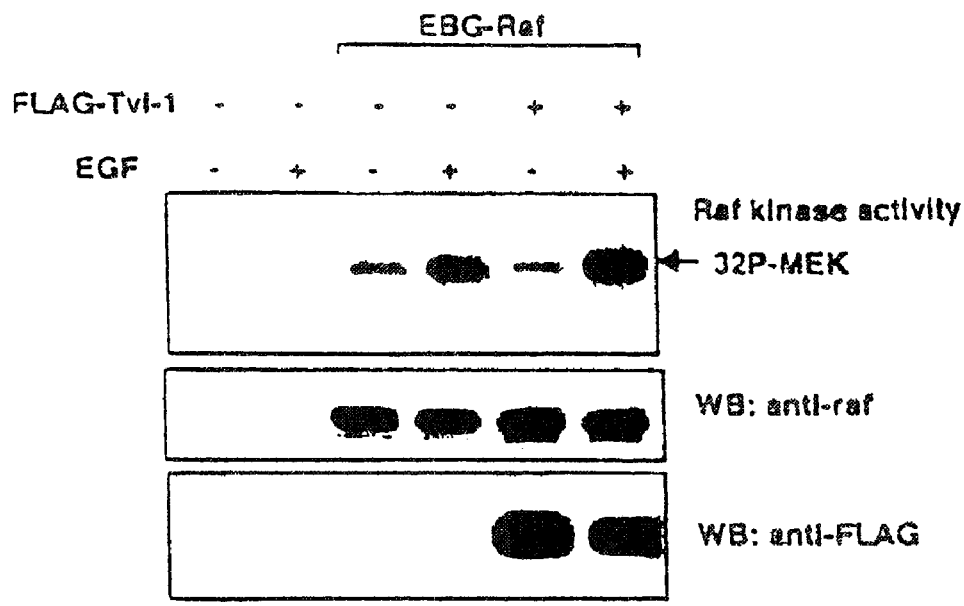

Tvl-1 Potentiates the Activation of Raf-1. In FIG. 8 it is shown that Tvl-1 enhances the activation of Raf-1 induced by v-Ras/v-Src in Sf9 cells and by EGF in COS-1 cells. A, top panel: in vitro kinase reactions were carried out using Raf-1 immunoprecipitated from lysates of Sf9 cells infected with the indicated baculovirus combinations. Bacterially expressed kinase-dead His$_6$-MEK1 was used as the exogenous kinase substrate. Middle panel, Western blot of the total infected cell lysates probed with anti-Raf, anti-Ras, and anti-Src antibodies. Bottom panel, quantitation of the Raf-1 kinase activity from the top panel by PhosphorImager. B, COS-1 cells were transfected with pEBG (lanes 1 and 2) or pEBG-Raf-1 expression construct (lanes 3–6) alone or in combination with the pMV-FLAG-Tvl-1 expression construct (lanes 4 and 5). Twenty-four hours after transfection, cells were serum-starved overnight, and stimulated with EGF (50 ng/ml) for 20 min. Cells were lysed and GST-Raf-1 was pulled down for kinase assays using recombinant kinase-dead His$_6$-MEK1 as the exogenous substrate (top panel). Total cell lysates were Western blotted and probed with anti-Raf-1 or anti-FLAG antibody (lower two panels). The experiments in both A and B were repeated three times with similar results.

Thus, to determine whether Tvl-1 modulates the activity of the Raf-1 kinase we examined the kinase activity of Raf-1 in Sf9 cells co-expressing Tvl-1 and Raf-1 in the presence or absence of v-Src plus v-Ha-Ras. To this end, Sf9 cells were infected with baculoviruses expressing Tvl-1, Raf-1, v-Src, and v-Ha-Ras in the combinations shown in FIG. 8A. Forth-eight hours later the infected cells were lysed in a RIPA lysis buffer. An in vitro kinase reaction carried out using Raf-1 immunoprecipitated from these lysates, and histidine-tagged kinase-dead MEK-1 as the exogenous substrate revealed that Tvl-1 potentiates the activation of Raf-1 by Src and Ras. The potentiation of the activation of Raf-1 by Tvl-1 is highly reproducible, with very similar results obtained in three independent experiments. To determine whether Tvl-1 has a similar effect on the activity of the Raf-1 kinase in mammalian cells, we overexpressed Tvl-1 in COS-1 cells and examined the kinase activity of Raf-1 following overnight serum starvation and EGF stimulation for 20 min. As shown in FIG. 8B, while overexpression of Tvl-1 had no effect on the kinase activity of Raf-1 in unstimulated cells, it significantly enhanced the activation of Raf-1 by EGF. Similar results were obtained in three independent experiments.

Presented in this example is the cloning and initial characterization of a gene (Tvl-1) encoding a novel ankyrin repeat protein that interacts with Raf-1 and is phosphorylated by the Raf-1 kinase. Through its interaction with Raf-1, Tvl-1 also promotes the activation of the Raf-1 kinase by Src and Ras. The phosphorylation of Tvl-1 by Raf-1 appears to be specific. Thus, Tvl-1 is not phosphorylated by Raf-1 expressed in the absence of Src and/or v-Ha-ras, but is phosphorylated by the constitutively active Raf-1 mutant Y340D. Moreover, Tvl-1 is not phosphorylated by a co-immunoprecipitating kinase because the kinase-dead mutant Raf-1K375M failed to phosphorylate Tvl-1 when immunoprecipitated from lysates of Sf9 cells co-expressing this Raf-1 mutant and v-Ha-ras plus v-src. Tvl-1 was detected in both the cytosol and the nucleus of cells transiently transfected with Tvl-1 expression constructs. Moreover, Tvl-1 was shown to interact with Raf-1 not only in cells overexpressing the two proteins, but also in untransfected cells expressing natural protein levels. These findings suggest that the interaction of Tvl-1 with Raf-1 and its consequences are physiologically possible.

Although studied extensively, the molecular mechanism (s) of Raf-1 activation by growth factors remain relatively poorly understood. The process of activation is regulated by the interaction of Raf-1 with a host of cellular proteins, one of which is the Tvl-1 protein described in this report. Tvl-1, similar to other interacting proteins such as 14-3-3, does not activate Raf-1 by itself (29,30). Instead, it potentiates the activation of Raf-1 by signals transduced by other signaling molecules such as Src and Ras (51). Earlier studies had shown that Raf-1 can be activated by both Ras-dependent and independent mechanisms (52, 53). The findings presented in this report, therefore, suggest that Tvl-1, similar to 14-3-3, is involved in the activation of Raf-1 by signals that are Ras-dependent.

Tvl-1 may potentiate the activation of Raf-1 by affecting its conformation and thus influencing the association of Raf-1 with other activating molecules. Alternatively, Tvl-1 may function as a scaffold protein that contributes to the assembly of Raf-1-activating multimolecular complexes, or may contribute to the association of Raf-1 with the plasma membrane. A scaffolding role for Tvl-1 is supported by the fact that it contains multiple ankyrin repeat motifs that function as domains of protein-protein interaction, and oligomerize spontaneously. The potential involvement of Tvl-1 in promoting the association of Raf-1 with the plasma membrane was suggested by findings that other Raf-1-interacting proteins, such as Ras, may enhance Raf-1 activity by this mechanism (23, 24, 54). In the case of Tvl-1 this does not seem to be the case, however, because a myristylated form of Tvl-1, which is membrane-associated, failed to enhance the activation of Raf-1. We conclude that Tvl-1 either forms a bridge between Raf-1 and other Raf-1 activating proteins or directly affects Raf-1 protein conformation facilitating its activation by other interacting proteins.

The only other known Raf-1 substrates to date are MEK-1, Cdc25A and Bad. Phosphorylation of MEK-1 activates the kinase and contributes to the propagation of the signal from Raf-1 to the MAPK (31–33, 55). Phosphorylation of Cdc25A plays a role in the activation of this phosphatase (34). Finally, phosphorylation of Bad may prevent its interaction with the antiapoptotic Bcl-2 family members in the mitochondria, thus inhibiting apoptosis (35). Given that Tvl-1 appears to modulate Raf-1 activity, phosphorylation of Tvl-1 by Raf-1 may alter the binding affinity between the two proteins and it may promote their dissociation. Such an outcome would interrupt the Tvl-1-mediated Raf-1 activation signal. Alternatively, phosphorylated Tvl-1 may contribute to the transduction of downstream Raf-1 signals. To date we know that Tvl-1 does not activate the MAPK pathway in NIH 3T3 cells (unpublished results). It remains to be determined whether Tvl-1 affects the phosphorylation of cdc-25a and Bad by Raf-1, or whether it transduces signals to other growth factor-activated pathways.

Overall, the data presented in this example show that Tvl-1 interacts with Raf-1 in mammalian cells even when it is expressed at natural levels. Furthermore, the data from overexpression studies clearly show that Tvl-1 has the potential to both regulate Raf-1 and to function as a Raf-1 downstream target.

EXAMPLE II

Biochemical Characterization of the Role Played by TVL-1 in Apoptosis

Tvl-1, a 269 amino acid ankyrin repeat protein, was identified by screening a murine T-cell two hybrid cDNA library for proteins that associate with Raf-1. The gene encoding Tvl-1 maps to human chromosome 19p12, 0.7 kb upstream of MEF2B and is expressed in all tested tissues with highest levels in hematopoietic and lymphoid organs and testes. Extending observations based on the screening of an interaction mating library of approximately 500 proteins for interactors of Tvl-1, we showed that Tvl-1 also binds Mcl-1, BcL-$X_L$ and Bad but no other members of the Bcl-2 family of proteins, caspase-9, but not caspase-8 or caspase-3, Akt-1, but not Akt-2 or Akt-3, Tpl-2, and cyclins D1, D2 and D3. Through its interaction with Akt-1 or Tpl-2 and caspase-9 it can form a bridge between these proteins. Similarly, it appears to bridge Akt-1 and Bad and Bcl-$X_L$ and caspase-9. Treatment with TNF-α enhanced the interaction of Tvl-1 with Mcl-1 in NIH3T3 cells. More importantly, stable overexpression of Tvl-1 in NIH3T3 cells potentiated TNF-α induced activation of caspase-3 and apoptosis. During IL-6-induced differentiation of the myelomonocytic cell line M1, expression of Tvl-1 was markedly enhanced. Overexpression of a Tvl-1 deletion mutant containing only the ankyrin repeat region, in the same cells blocked IL-6-induced Gi arrest and differentiation. Moreover, Tvl-1 expression was downregulated in synchronized growth-factor-dependent cell lines as they progressed through G1. The last three observations, combined, suggest that Tvl-1 inhibits the progression from G1 to S and that its down-regulation is required for this transition. Based on this information experiments were designed to address the role of Tvl-1 in apoptosis, cell cycle progression and differentiation. The information obtained by these studies will further elucidate the pathobiology of neoplasia with emphasis on cell cycle progression, differentiation and apoptosis.

The apoptotic program can be triggered by intrinsic cellular signals, such as DNA damage, or external signals delivered by neighboring or distant cells. Little is known to date about the specificity of the apoptotic network at either the cell or the gene level. Gene inactivation experiments have shown, however, that apoptosis can be a highly specific process. Thus, mice with an inactivated caspase-3 gene die perinatally because of a dramatic increase in the number of cells in the central nervous system but not in any other organs. Various externally delivered signals that trigger apoptosis are known. One of the factors that delivers such a signal is the tumor necrosis factor-alpha (TNF-α). TNF-α interacts with, and activates two receptors that are homologous in their extracellular domains, TNF-receptor I (TNF-RI) and TNF-receptor 2 (TNF-R2) (29–32). Although there is significant overlap between the signals transduced by the two receptors, apoptotic signals are transduced primarily by TNF-RI. The transduction of TNF-α signals via TNF-RI depends on the interaction of the receptor with several signaling molecules. These interactions are directed by an approximately 80 amino acid domain that is shared by the receptor and several of these molecules and is known as the death domain. The signals generated through these interactions activate two distinct pathways, one leading to the activation of SAPK and NF B, and another leading to apoptosis. Since the activation of NF B inhibits apoptosis, the two pathways appear to be in direct competition. The multimolecular complex that is assembled on the receptor and regulates apoptosis includes caspase-8 which upon activation triggers the caspase proteolytic cascade (14).

Data presented herein reveal that. Tvl-1 is an adaptor molecule that contributes to the formation of multimolecular complexes involved in the regulation of apoptosis. Briefly, Tvl-1 interacts with Mcl-I, and the interaction between the two molecules is enhanced in response to TNF-α. Tvl-1 also BcX$_L$, Bad and caspase-9 (but not caspase-8 or caspase-3) as well as with the antiapoptotic kinase Akt-1, (but not Akt-2 or Akt-3) and the proapoptotic kinase Tpl-2 (36–39). Through this interaction Akt-1 and Tpl-2 bind caspase-9. Additional findings presented herein show that Tvl-1 potentiates TNF-α-induced activation of the caspase pathway and apoptosis. Tvl-1 therefore appears to bridge several classes of regulators of apoptosis including Bcl-2 family members, caspases and kinases, and to regulate the cellular response to apoptotic signals. In accordance with the present invention, Tvl-1 encoding nucleic acids and proteins are used as probes to explore the assembly of multimolecular apoptotic complexes and the role of individual components of these complexes in regulating apoptosis.

Tvl-1 Promotes TNF-α Induced Activation of Caspase 3

To define the Tvl-1 domain, which is involved in its interaction with Mcl-1 and Bcl-$X_L$ and Bad, we carried out immunoprecipitation experiments using expression constructs of amino-terminal or carboxy-terminal deletions of Tvl-1. The results showed that it the ankyrin domain of Tvl-1 which interacts with Mcl-1, Bcl-$X_L$ and Bad. To determine whether Mcl-1 and Bcl-$X_L$ interact with Tvl-1 via their Bcl-homology domain (BH4) domain, which is involved in the interaction of these proteins with Raf-1, we carried out similar immunoprecipitation experiments using lysates of cells co-transfected with wild-type Tvl-1 and BH4 deletion mutants of Mcl-1 and Bcl-XL. The results showed that the BH4 domain is dispensable for this interaction.

The preceding findings revealed that Tvl-1 interacts with Mcl-1 and Bcl-XL and suggested that it may sequester Mcl-1 and Bcl-XL, thus making them unavailable to exert their anti-apoptotic function.

Figure 9A:
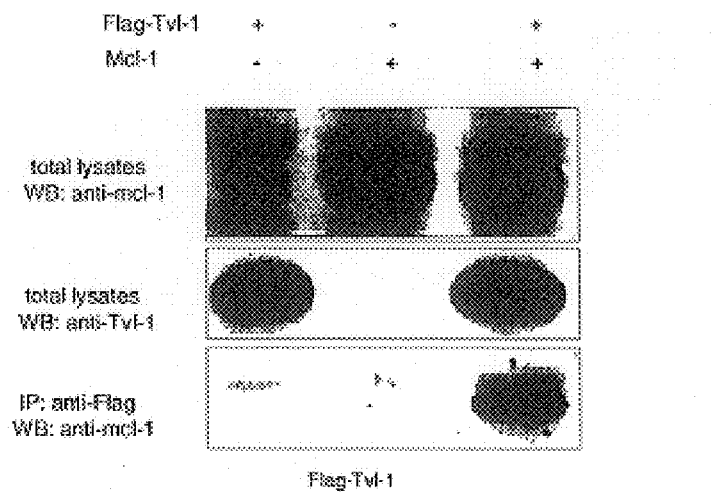
FIG. 9 shows that Tvl-1 interacts with Mcl-1, Bcl-$X_L$ and Bad but not with other members of the Bcl-2 protein family. The interaction between Tvl-1 and Mcl-1 is enhanced by TNF-α. (A) Upper two panels—Western blots of total lysates from 293T cells transiently transfected with FLAG-Tvl-1 and Mcl-1 expression constructs as indicated. Blots were probed with anti-Tvl-1 or anti-Mcl-1 antibodies. (A) Lower panel—Western blot of anti-FLAG immunoprecipitates or ght same lysates probed with an anti-Mcl-1 monoclonal antibodies. (B) Upper two panels—Western blots of total lysates of 293T cells transiently transfected with the indicated expression constructs. Blots were probed with anti-Tvl-1 or anti-HA monoclonal antibodies. (B) Lower two panels—Western blots of anti-HA or anti-FLAG immunoprecipitates of the same lysates probed with anti-Tvl-1 or anti-HA antibodies respectively. (C) Left panels—Western blots of total lysates of 293T cells transiently transfected with FLAG-Tvl-1 and Mcl-1 expression constructs and treated with TNF-α as indicated. Blots were probed with anti-Mcl-1 or anti-Tvl-1 antibodies. (C) Right panels—Western blots of anti-FLAG immunoprecipitates of the same lysates probed with anti-Mcl-1 or anti-Tvl-1 antibodies.
Figure 9B:
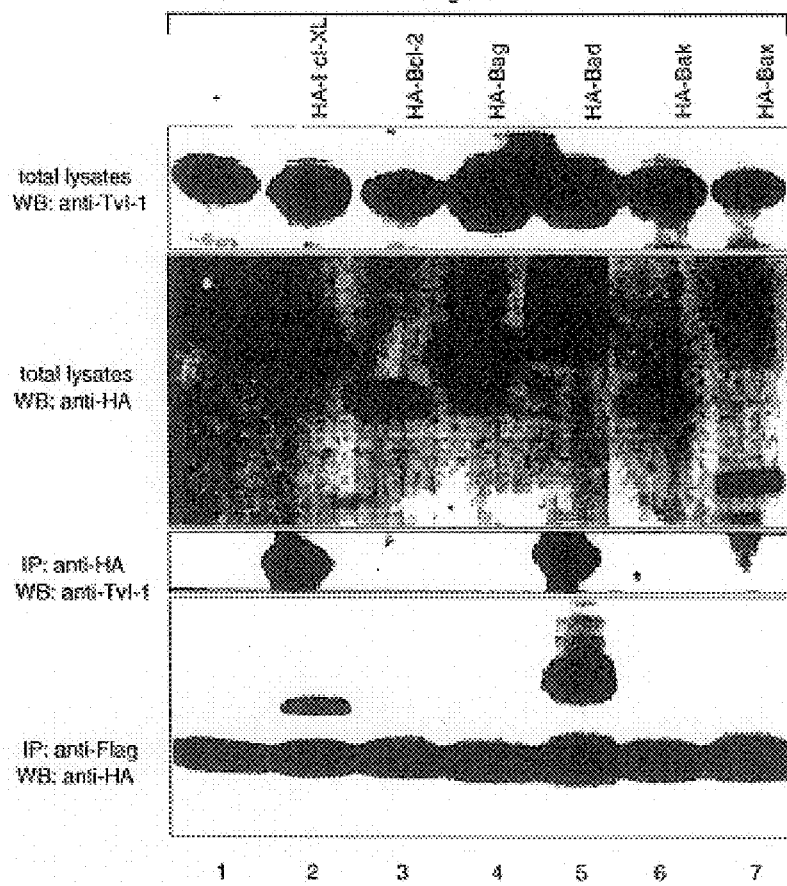
Figure 9C:
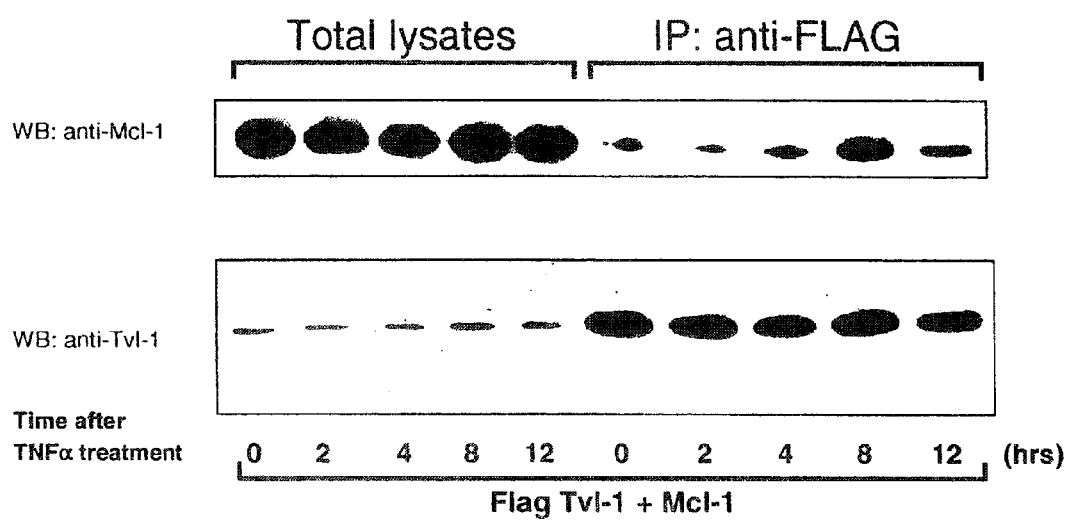

In FIG. 9 it is shown that Tvl-1 interacts with Mcl-1, Bcl-$X_L$ and Bad but not with other members of the Bcl-2 protein family. The interaction between Tvl-1 and Mcl-1 is enhanced by TNF-α. A. Upper two panels—Western blots of total lysates from 293T cells transiently transfected with FLAG-Tvl-1 and Mcl-1 expression constructs as indicated. Blots were probed with anti-Tvl-1 or anti-Mcl-1 antibodies. Lower panel—Western blot of anti-FLAG immunoprecipitates or ght same lysates probed with an anti-Mcl-1 monoclonal antibodies. B. Upper two panels—Western blots of total lysates of 293T cells transiently transfected with the indicated expression constructs. Blots were probed with anti-Tvl-1 or anti-HA monoclonal antibodies. Lower two panels—Western blots of anti-HA or anti-FLAG immuno-precipitates of the same lysates probed with anti-Tvl-1 or anti-HA antibodies respectively. C. Left panels—Western blots of total lysates of 293T cells transiently transfected with FLAG-Tvl-1 and Mcl-1 expression constructs and treated with TNF-α as indicated. Blots were probed with anti-Mcl-1 or anti-Tvl-1 antibodies. Right panels—Western blots of anti-FLAG immunoprecipitates of the same lysates probed with anti-Mcl-1 or anti-Tvl-1 antibodies.

To determine whether the interaction of Tvl-1 with these inhibitors of apoptosis contributes to the transduction of apoptotic signals such as those induced by TNF-α, we examined the co-immunoprecipitation of Tvl-1 with Mcl-1 from co-transfected cells before and after treatment with TNF-α. To this end, NIH3T3 cells transfected with FLAG-Tvl-1 and Mcl-1 expression constructs either separately or together, were stimulated 48 hours after the transfection. Immunoprecipitation of Tvl-1 or Mcl-1 from NP40 lysates of the tranfected cells followed by Western blotting with the reciprocal antibody revealed that TNF-potentiates co-immunoprecipitation and therefore the interaction between the two proteins. See FIG. 9. Since Mcl-1 is a mitochondrial protein, these results suggest that TNF-α promote the translocation of Tvl-1 to the mitochondria.

Tvl-1 Promotes TNF-α-induced Apoptosis.

Mcl-1 and BcL-$X_L$ interact with proapoptotic members of the Bcl-2 family of proteins. Since Tvl-1 interacts primarily with the antiapoptotic members of the Bcl-2 family, it will effectively increase the levels of free proapoptotic family members in the mitochondria, following its translocation to these organelles in response to TNF-α. Such an outcome will reduce the mitochondrial membrane potential, will permit the release of cytochrome c to the cytoplasm and will promote apoptosis.

Figure 10A:
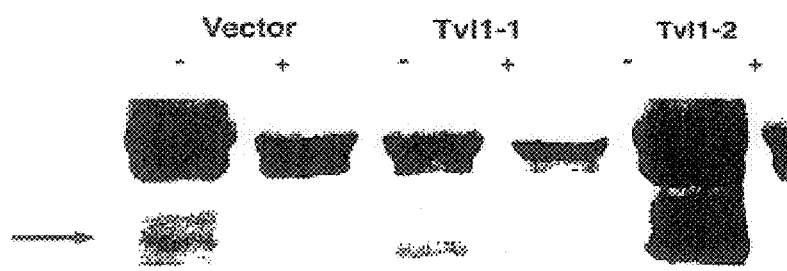
FIG. 10 shows that Tvl-1 promotes TNF-α-induced apoptosis in NIH3T3 cells. (A) SDS-PAGE of anti-Tvl-1 immunoprecipitates of $^{35}$S-methionine-labeled NIH3T3 cells stably transfected with Tvl-1 expression constructs (Tvl-1.1 and Tvl-1.2) or vector only. − and + indicate immunoprecipitations with immune serum in the absence or presence of the peptide against which the antiserum was raised. (B) Percentage of the dead cells in the vector and Tvl-1-transfected N1H3T3 cells before, and 48 hours after TNF-α treatment. (C) Photomicrographs of the vector and Tvl-1-transfected NIH3T3 cells before, and 48 hours after treatment with TNF-α. Representative data from two out of six vector and Tvl-1-transfected cell lines.

In FIG. 10 it is shown that Tvl-1 promotes TNF-α-induced apoptosis in NIH3T3 cells. A. SDS-PAGE of anti-Tvl-1 immunoprecipitates of $^{35}$S-methionine-labeled NlH3T3 cells stably transfected with Tvl-1 expression constructs (Tvl-1.1 and Tvl-1.2) or vector only. − and + indicate immunoprecipitations with immune serum in the absence or presence of the peptide against which the antiserum was raised. B. Percentage of the dead cells in the vector and Tvl-1-transfected N1H3T3 cells before, and 48 hours after TNF-α treatment. C. Photomicrographs of the vector and Tvl-1-transfected N1H3T3 cells before, and 48 hours after treatment with TNF-α. Representative data from two out of six vector and Tvl-1-transfected cell lines.

Figure 10B:
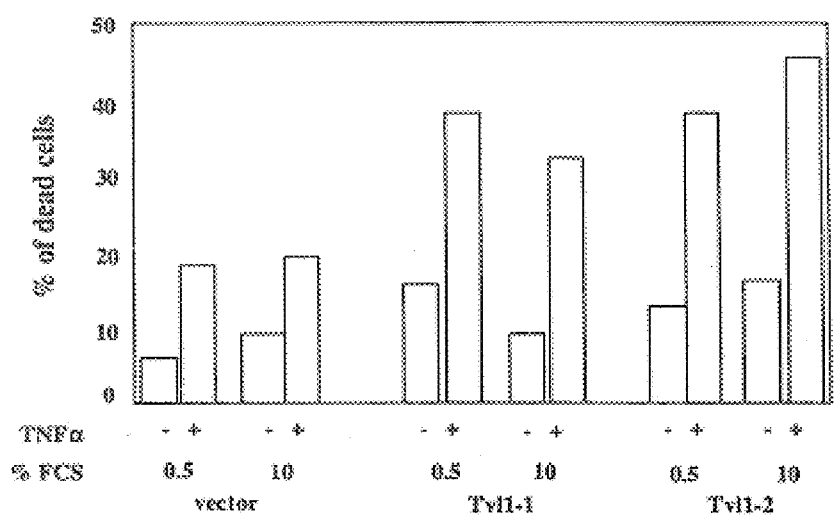
Figure 10C:
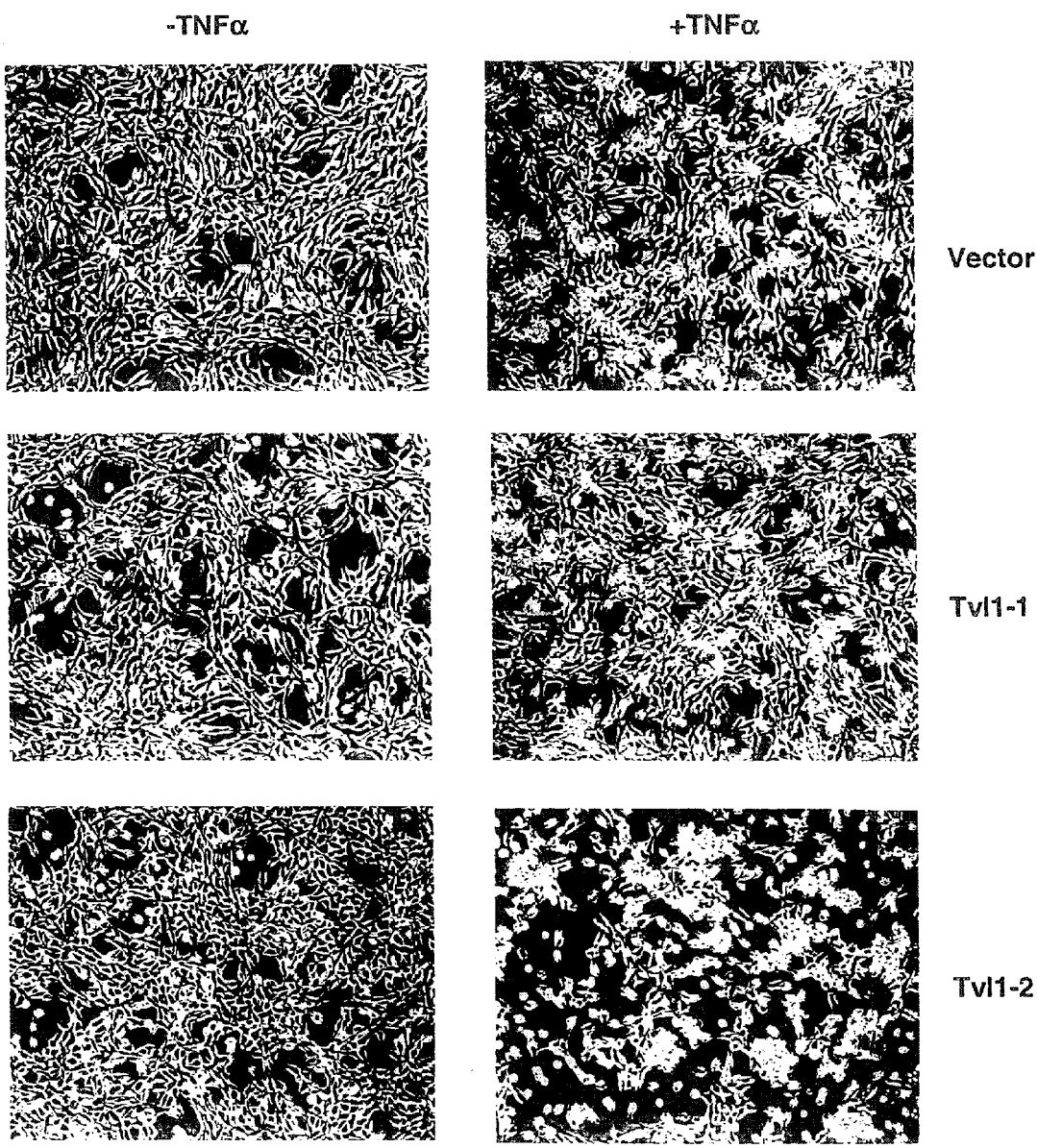

Six independent mass cultures of NIH 3T3 cells were engineered to stably express Tvl-1 from an SR expression construct. These cells express Tvl-1 at only slightly higher levels than normal NIH 3T3 cells (FIG. 10A), and they do not undergo spontaneous apoptosis. However, when stimulated with TNF-α, their apoptotic response is significantly more pronounced by comparison with the apoptotic response of NIH 3T3 cells carrying the empty vector (FIGS. 10B and 10C).

Tvl-1 Promotes TNFα-induced Activation of Caspase 3

TNF-α-induced apoptosis is due to the activation of several members of the caspase family of cysteine proteases one of which is caspase-3, also known as CPP-32. To explore the mechanism by which Tvl-1 potentiates the apoptotic response to TNF-α, we examined whether Tvl-1 modulates the TNF-α induced activation of caspase 3, as determined by the cleavage of a DEVD-AFC fluorogenic substrate.

Figure 11:
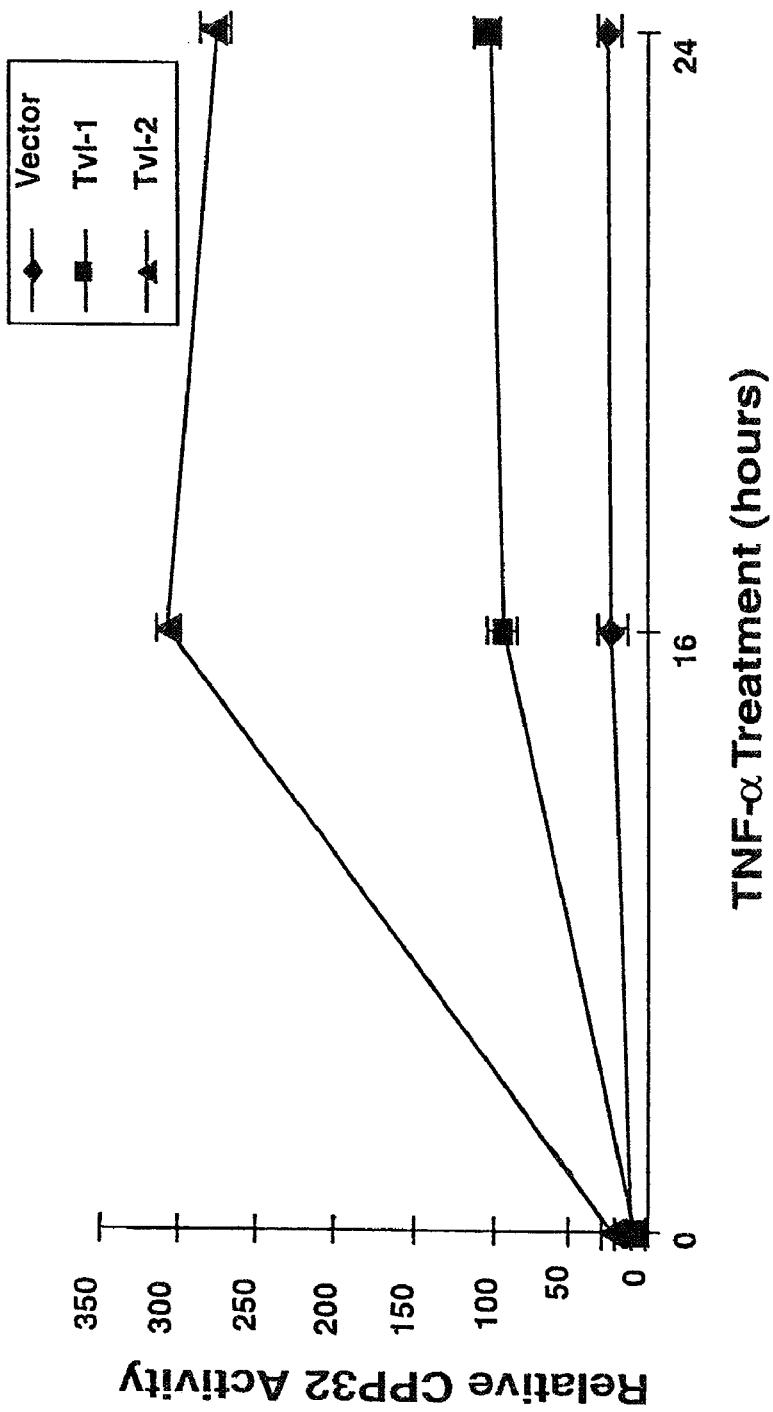
FIG. 11 shows that Tvl-1 promotes TNF-α-induced activation of caspase-3 in NIH3T3 cells.

In FIG. 11 it is shown that Tvl-1 promotes TNF-α-induced activation of caspase-3 in NIH3T3 cells. Caspase-3 activity in lysates of vector and Tvl-1-transfected N1H3T3 cells harvested before, and 16 or 24 hours after treatment with TNF-α was determined by the cleavage of a DEVD-AFC fluorigenic substrate. Tvl1.1 cells, which express higher levels of Tvl-1 than Tvl1.2 cells (FIG. 9A), also exhibit higher levels of caspase-3 activity in response to TNF-treatment.

The results confirmed that indeed the activation of caspase-3 by TNF-α is significantly enhanced in Tvl-1 expressing NIH3T3 cells. See FIG. 11. This agrees with, and supports the preceding data suggesting that TNF-α may promote translocation of Tvl-1 to the mitochondria. Such as event would indeed increase the net levels of proapoptotic Bcl-2 family members in the mitochondria and would enhance the TNF-α-induced release of mitochondrial cytochrome c and activation of the caspase pathway.

The proposed mechanism for the potentiation TNF-α-induced apoptosis by Tvl-1 does not take into account the association of Tvl-1 with Bad. In cells expressing Bad, two forms of the protein can be detected. One form is phosphorylated, the other is not. The unphosphorylated form is localized primarily in the mitochondria and promotes apoptosis, while the phosphorylated form is sequestered by 14-3-3 in the cytoplasm. Phosphorylation of Bad by serine-threonine kineses such as Akt promotes its sequestration in the cytoplasm and inhibits apoptosis. Tvl-1 is a cytoplasmic/nuclear protein that binds equally well to the nonphosphorylated and the phosphorylated forms of Bad (data not shown). This suggests that Tvl-1 contributes to the sequestration of both forms of Bad in the cytoplasm thus inhibiting apoptosis. Alternatively, Tvl-1 may translocate to the mitochondria in response to apoptotic signals, thereby mediating the mitochondrial translocation and proapoptotic activity of Bad which is triggered by apoptosis-inducing signals. Tvl-1 may also interfere with the phosphorylation of Bad by antiapoptotic kinases such as Akt, an event that also promotes the Bad proapoptotic function.

Tvl-1 Overexpression Induces the Release of Cytochrome c From the Mitochondria Even in the Absence of TNF-α.

Figure 12:
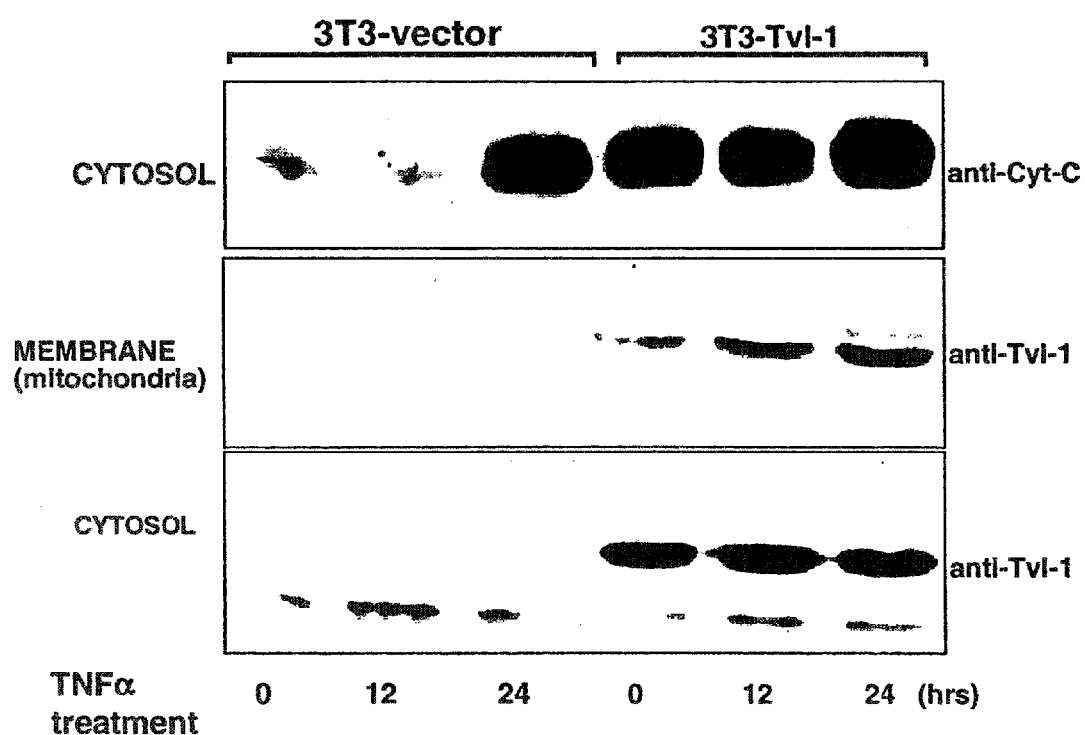
FIG. 12 is the Western blots showing that Tvl-1 overexpression induces the release of cytochrome c from the mitochondria in the absence of TNF-α.

Presented in FIG. 12 are Western blots showing that Tvl-1 overexpression induces the release of cytochrome c from the mitochondria in the absence of TNF-α. NIH3T3 cells were stably transfected with a Tvl-1 expression construct or vector only. The transfected cells were fractionated into cytosolic and mitochondrial fractions at 0, 12 and 24 hours following treatment with TNF-α. The samples were subjected to SDS page and Western blotting using anti-cytochrome c and anti-Tvl-1 antibodies. The data show that overexpression of Tvl-1 induced cytochome c release even at the 0 time point prior to treatment with TNF-α. See FIG. 12.

Tvl-1 Binds Caspase-9 but Does Not Bind Caspase-8 or Caspase-3.

The data in FIGS. 9 and 10 show that Tvl-1 promotes the activation of caspase-3 and apoptosis in response to TNF-α. Since Tvl-1 might increase the net levels of proapoptotic Bcl-2 family members in the mitochondria of TNF-α-treated cells, the activation of caspase-3 could be the result of cytochrome c release from these organelles. Cytochrome c released from the mitochondria and DATP bind Apaf-1), a protein that complexes with caspase-9 in the cytoplasm. Caspase-9, activated via this process, activates caspase-3. However, Tvl-1 may also interact directly with the Apaf-1 multimolecular complex. A precedent for that comes from the antiapoptotic members of the Bcl-2 protein family, which not only inhibit cytochrome c release from the mitochondria, but also inhibit caspase activation following the release of cytochrome c.

To address this question, expression constructs of Flag-Tvl-1 and caspase-cleavage-site mutants of caspase-8, caspase-9 or caspase-3 tagged at their amino-terminus with a T7 epitope tag were co-transfected into 293T cells.

Forty-eight hours later, the cells were lysed in an NP-40 lysis buffer. Flag-Tvl-1 was immunoprecipitated from the lysates, and Western blots of the immunoprecipitates were probed with an anti-T7 tag monoclonal antibody.

Figure 13:
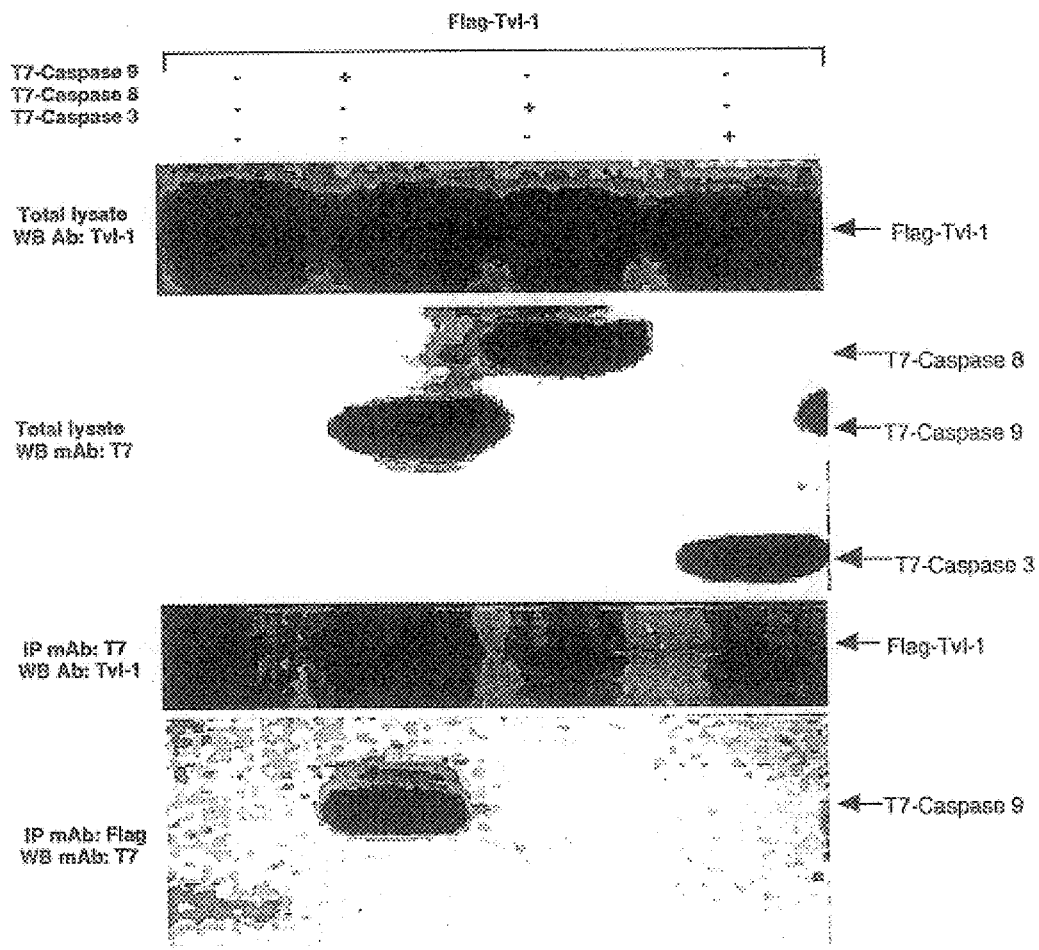
FIG. 13 shows that Tvl-1 interacts with caspase-9 but not with caspase-8 or caspase-3. (A) Upper two panels: Western blots of total lysates of 293T cells transiently transfected with expression constructs of T7-tagged caspase-3, caspase-8 and caspase-9 (carrying mutations in the caspase cleavage sites) and Flag-Tvl-1. Blots were probed with anti-Tvl-1 or anti-T7 antibodies as indicated. (A) Lower two Panels: Western blots of the caspase (anti-T7) or Tvl-1 (anti-Flag) immunoprecipitates probed with the anti-Tvl-1 or the anti-T7 antibodies respectively show that Tvl-1 co-immunoprecipitates only with caspase-9 but not caspase-3 or caspase-8.

In FIG. 13 it is shown that Tvl-1 interacts with caspase-9 but not with caspase-8 or caspase-3. (Upper two panels) Western blots of total lysates of 293T cells transiently transfected with expression constructs of T7-tagged caspase-3, caspase-8 and caspase-9 (carrying mutations in the caspase cleavage sites) and Flag-Tvl-1. Blots were probed with anti-Tvl-1 or anti-T7 antibodies as indicated. (Lower two Panels) Western blots of the caspase (anti-T7) or Tvl-1 (anti-Flag) immunoprecipitates probed with the anti-Tvl-1 or the anti-T7 antibodies respectively show that Tvl-1 co-immunoprecipitates only with caspase-9 but not caspase-3 or caspase-8. This and additional experiments in which the immunoprecipitations and Western blots were carried out in the reverse order revealed that Tvl-1 interacts with caspase-9 but not with caspase-8 or caspase-3. See FIG. 13.

Tvl-1 Interacts with the Antiapoptotic Serine-threonine Protein Kinase Akt-1 (but not with Akt-2 or Akt-3) and the Proapoptotic Serine-threonine Protein Kinase Tpl-2.

The preceding data revealed that Tvl-1 interacts with Mcl-1, Bcl-$X_L$, Bad and caspase-9 as well as with the serine-threonine protein kinase Raf-1. This suggests that Tvl-1 may form a bridge between kinases and several regulators of apoptosis. Before addressing this question we've proceeded to determine whether Tvl-1 interacts with additional kinases that are known to play an important role in the regulation of apoptosis. The kinases we chose were Akt-1 (or c-akt) which represents a major inhibitor of apoptosis, and Tpl-2 which promotes apoptosis. To this end, expression constructs of Tvl-1 were co-transfected into 293T cells with expression constructs of Akt-1, Akt-2, Akt-3 or Tpl-2. Forty-eight hours later, the transfected cells were lysed in an NP-40 lysis buffer.

Figure 14A:
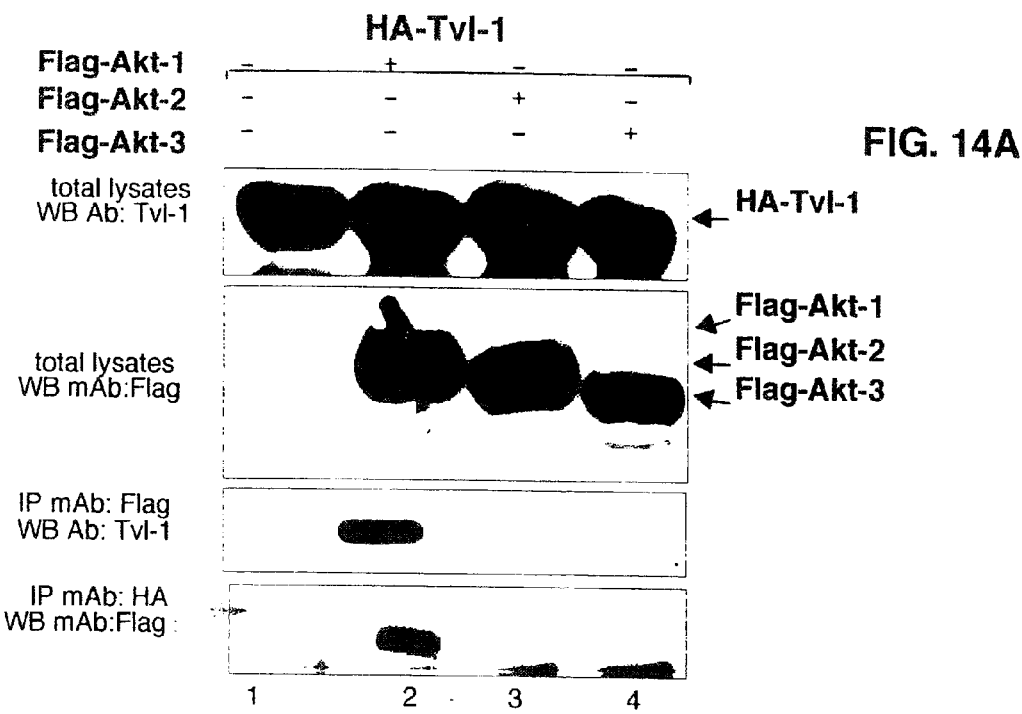
FIG. 14 shows that Tvl-1 interacts with Akt-1 (but not Akt-2 or Akt-3) and Tpl-2. (A) Upper two Panels: Western blots of total lysates of 293T cells transiently transfected with HA-Tvl-1 and Flag-tagged Akt-1, Akt-2 or Akt-3 expression constructs as indicated. Blots were probed with anti-Tvl-1 or anti-Flag antibodies. (A) Lower two Panels: Western blots of anti-Flag (Akt-1, Akt-2 or Akt-3) or anti-HA (Tvl-1) immunoprecipitates probed with anti-Tvl-1 or anti-Flag antibodies respectively show that Tvl-1 interacts specifically with Akt-1. (B) immunoprecipitation of Tvl-1 or Tpl-2 from and $^{35}$S-labeled COS-1 cells transfected with Tvl-1 and Tpl-2 expression constructs as indicated. Tpl-2 and Tvl-1 co-immuno-precipitate from lysates of cells co-transfected with the two constructs.
Figure 14B:
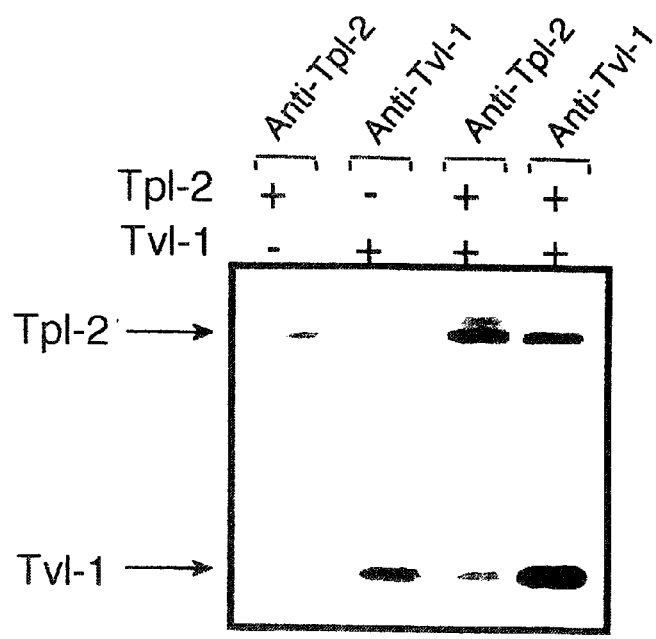
Figure 15A:
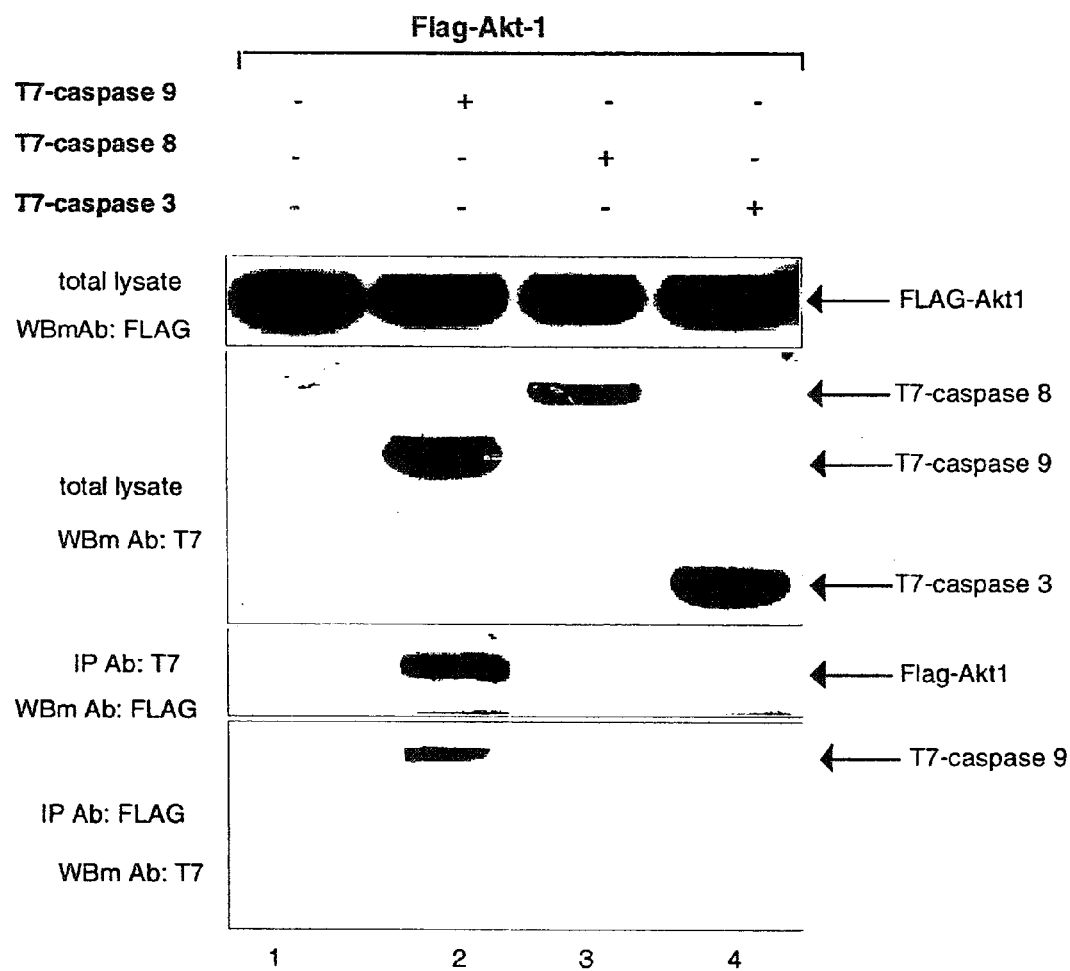
FIG. 15 shows that Caspase-9 (but not caspase-8 or caspase-3) interacts with Akt-1 and Tpl-2 perhaps via Tvl-1. Akt-1 and Tpl-2 are activated by different signals. (A) Upper two Panels: Western blots of total lysates of 293T cells transiently transfected with Flag-Akt-1 and T7-caspase (caspase-3, caspase-8 and caspase-9) expression constructs as indicated. Blots were probed with anti-Flag or anti-T7 antibodies. (A) Lower two panels: Western blots of the caspase (anti-T7) and the Akt-1 (anti-Flag) immunoprecipitates, probed with anti-Flag (Akt-1) or anti-T7 (caspases) antibodies respectively, revealed that Akt-1 interacts with caspase-9 but not caspase-8 or caspase-3. (B) Upper three Panels: Western blots of total lysates of 293T cells transfected with myc-tagged Tpl-2 (Tpl-2 wt. MT), Flag-tagged Tvl-1 (Flag-Tvl-1) and T7-caspase constructs as indicated. Blots were probed with the anti-myc tag monoclonal antibody 9E10, the anti-Flag antibody or the anti-T7 monoclonal antibody. (B) Lower Panel: Western bolt of Tpl-2 immunoprecipitates (anti-myc tag), probed with the anti-T7 antibody, revealed that caspase-9 co-immunoprecipitates with Tpl-2 and that co-expression of Arp-1 potentiates the interaction. (C) In vitro kinase assays of HA-Akt-1, immunoprecipitated from EL4.IL-2 cells, stimulated with IL-2 or Jurkat cells stimulated with TNFα as indicated. The exogenous kinase substrate was histone H2B. (D) In vitro kinase assays of Tpl-2, immunoprecipitated from NIH3T3 cells, stably transfected with a wild type Tpl-2 expression construct and stimulated with a variety of growth factors, revealed that Tpl-2 is activated by TNF-α but not by other growth factors. The phosphorylated band is autophosphorylated Tpl-2.
Figure 15B:
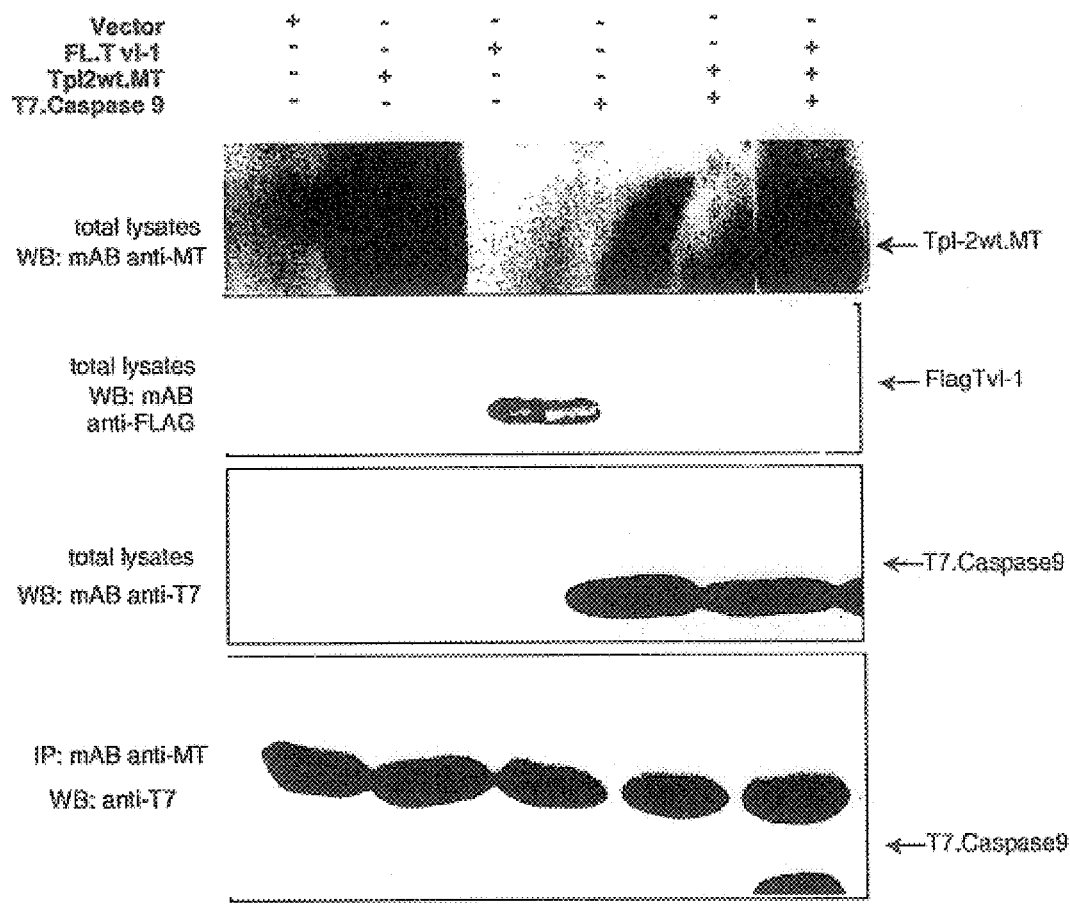
Figure 15C:
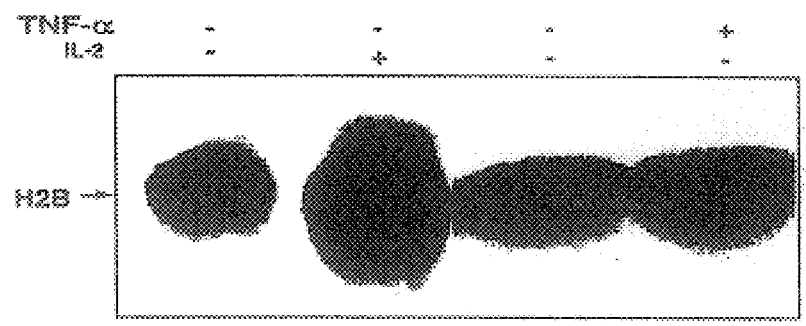
Figure 15D:
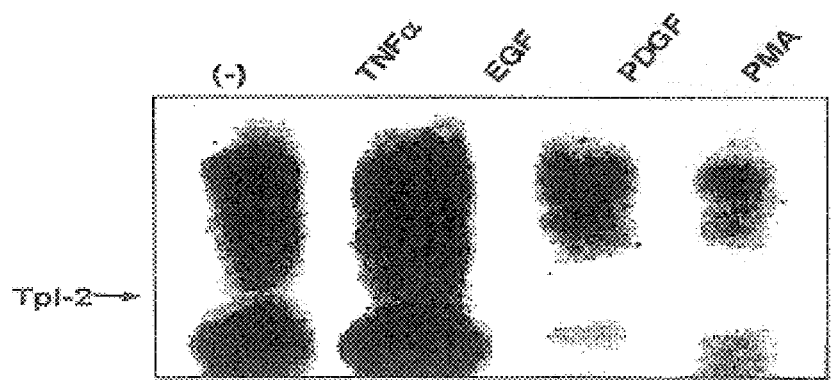

In FIG. 14 it is shown that Tvl-1 interacts with Akt-1 (but not Akt-2 or Akt-3) and Tpl-2. A. (Upper two Panels) Western blots of total lysates of 293T cells transiently transfected with HA-Tvl-1 and Flag-tagged Akt-1, Akt-2 or Akt-3 expression constructs as indicated. Blots were probed with anti-Tvl-1 or anti-Flag antibodies. (Lower two Panels) Western blots of anti-Flag (Akt-1, Akt-2 or Akt-3) or anti-HA (Tvl-1) immunoprecipitates probed with anti-Tvl-1 or anti-Flag antibodies respectively show that Tvl-1 interacts specifically with Akt-1. B. Immunoprecipitation of Tvl-1 or Tpl-2 from and $^{35}$S-labeled COS-1 cells transfected with Tvl-1 and Tpl-2 expression constructs as indicated. Tpl-2 and Tvl-1 co-immuno-precipitate from lysates of cells co-transfected with the two constructs.

Co-immunoprecipitation experiments, carried out as shown in FIG. 14, revealed that Tvl-1 interacts with both Akt-1 (but not Akt-2 or Akt-3) and Tpl-2.

Akt-1 and Tpl-2 Interact with Caspase-9

The preceding data support the hypothesis that Tvl-1 may indeed form a bridge between several kineses and other regulators of apoptosis. To address this question, we first examined whether Akt-1 (or Akt-2 or Akt-3) and Tpl-2 interact with caspase-9 in the presence or absence of Tvl-1. To this end, 293T cells were co-transfected with expression constructs of Akt-1, Akt -2, Akt-3 or Tpl-2 and caspase cleavage site mutants of caspase-9, with or without Tvl-1.

In FIG. 15 it is shown that Caspase-9 (but not caspase-8 or caspase-3) interacts with Akt-1 and Tpl-2 perhaps via Tvl-1. Akt-1 and Tpl-2 are activated by different signals. A. (Upper two Panels) Western blots of total lysates of 293T cells transiently transfected with Flag-Akt-1 and T7-caspase (caspase-3, caspase-8 and caspase-9) expression constructs as indicated. Blots were probed with anti-Flag or anti-T7 antibodies. (Lower two panels) Western blots of the caspase (anti-T7) and the Akt-1 (anti-Flag) immunoprecipitates, probed with anti-Flag (Akt-1) or anti-T7 (caspases) antibodies respectively, revealed that Akt-1 interacts with caspase-9 but not caspase-8 or caspase-3. B. (Upper three Panels) Western blots of total lysates of 293T cells transfected with myc-tagged Tpl-2 (Tpl-2 wt. MT), Flag-tagged Tvl-1 (Flag-Tvl-1) and T7-caspase constructs as indicated. Blots were probed with the anti-myc tag monoclonal antibody 9E10, the anti-Flag antibody or the anti-T7 monoclonal antibody. (Lower Panel) Western bolt of Tpl-2 immunoprecipitates (anti-myc tag), probed with the anti-T7 antibody, revealed that caspase-9 co-immunoprecipitates with Tpl-2 and that co-expression of Arp-1 potentiates the interaction. C. In vitro kinase assays of HA-Akt-1, immunoprecipitated from EL4.IL-2 cells, stimulated with IL-2 or Jurkat cells stimulated with TNF-α as indicated. The exogenous kinase substrate was histone H2B. D. In vitro kinase assays of Tpl-2, immunoprecipitated from NIH3T3 cells, stably transfected with a wild type Tpl-2 expression construct and stimulated with a variety of growth factors, revealed that Tpl-2 is activated by TNF-α but not by other growth factors. The phosphorylated band is autophosphorylated Tpl-2.

Immunoprecipitation and Western blot experiments carried out as shown in FIG. 15, revealed that Akt-1 and Tpl-2 interact, like Tvl-1, with caspase-9 (FIG. 15). The pattern of interaction of these kinases with caspase-9 suggests that Tvl-1 may indeed form a bridge between these molecules. This is further supported by the finding that co-transfection of Tvl-1 promotes the co-immunoprecipitation of Tpl-2 with caspase-9 (FIG. 15B).

The preceding data suggest that Tvl-1 forms a bridge between several regulators of apoptosis including caspase-9, and perhaps Mcl-1, BCl-XL and Bad, and several kinases that either inhibit or promote apoptosis. These kinases may phosphorylate Tvl-1 and interfere with its role as an assembly molecule. Alternatively, they may phosphorylate the regulators of apoptosis they associate with, and they may regulate their function. Thus, we already know that Akt phosphorylates and inhibits the proapoptotic regulator Bad. Moreover, inspection of the caspase-9 sequence revealed two potential Akt-1 phosphorylation motifs (183RTRTGS188, 196RRRFSS201).

The final outcome of the association of kinases with opposing function like Akt-1 and Tpl-2 with regulators of apoptosis may depend on the nature of the incoming signals. It is, for example, known that signals generated by growth factors that inhibit apoptosis activate Akt-1 but do not affect the activity of Tpl-2 (FIG. 13B). On the other hand, TNF-α signals activate Tpl-2 but not Akt-1 (FIG. 13B).

Recent findings show that antiapoptotic members of the Bcl-2 family of proteins inhibit apoptosis by interacting with the apoptotic machinery at multiple levels. Earlier studies had suggested that Bcl-2 inhibits the release of cytochrome c from the mitochondria. However, more recent studies showed that Bcl-2 and perhaps other members of this family inhibit the activation of caspase-9 and caspase-3 even after the release of cytochrome c from the mitochondria, and suggested that these proteins may exert a direct inhibitory effect on caspase activation. This direct effect may be similar to that of ced-9, a C. elegans Bcl-2 homolog which interacts with ced-4 and inhibits activation of the caspase ced-3. Recently, it was shown that Bcl-$X_L$ (but not Bcl-2) indeed interacts with the Apaf-1/caspase-9 complex indirectly via an unidentified molecule (E. Alnemri, personal communication). Based on the preceding data, we suggest that this unidentified molecule is Tvl-1. If this is true, Tvl-1 may, under certain conditions, inhibit apoptosis by bridging Bcl-$X_L$ with the Apaf-1/caspase-9 complex.

The Interaction of Caspase-9 with Tpl-2 is Enhanced by Tvl-1. The Interaction of Caspase-9 with Tvl-1 is Enhanced by Tpl-2.

Figure 16A:
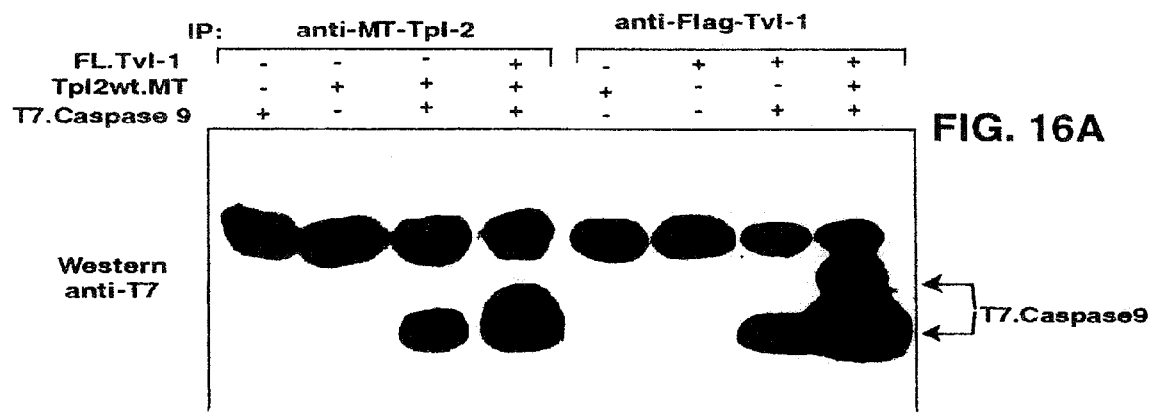
FIG. 16A shows Western blots of the immunoprecipitates were probed with the anti-T7 antibody with detects coprecipitating T7-caspase 9.

Shown in FIG. 16are Western blots showing that the interaction of caspase-9 with Tpl-2 is enhanced by Tvl-1. The data also show the Tpl-1 mediated enhancement of the interaction of caspase-9 with Tvl-1.

Figure 16B:
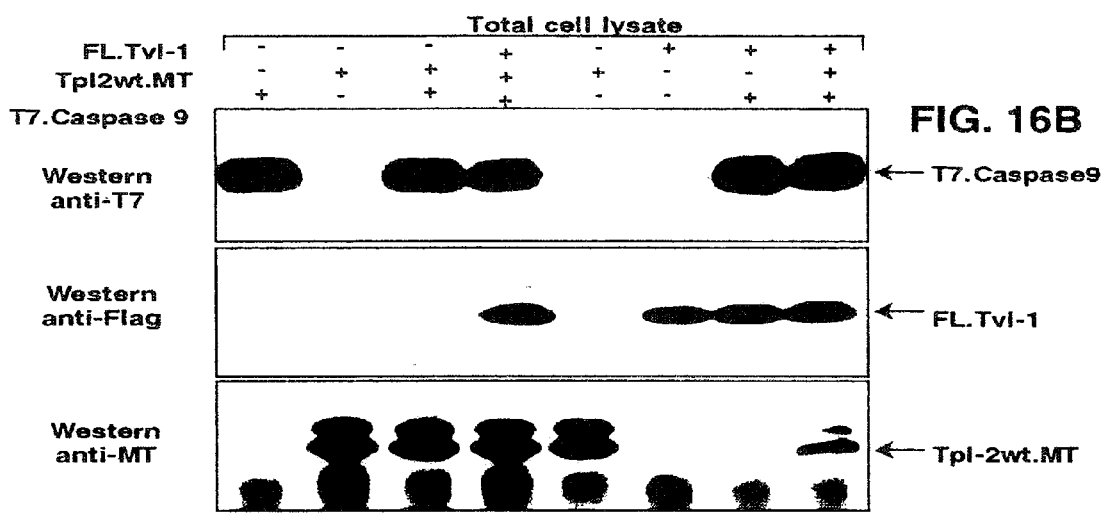
FIG. 16B shows Western blots of total cell lysates derived from the same cells in FIG. 16A and probed with the indicated antibodies.

293T cells were transiently transfected with FLAG-tagged Tvl-1 (FL::Tvl-1), myc-tagged Tpl-2 (Tpl2::MT) and T7-tagged caspase 9 as indicated in FIG. 16. NP-40 lysates of the transfected cells were immunoprecipitated with the anti-myc tag antibody (anti-MT/Tpl-2) or the anti-FLAG antibody (FLAG/Tvl-1) as indicated. Western blots of the immunoprecipitates were probed with the anti-T7 antibody with detects coprecipitating T7-caspase 9. FIG. 16B shows Western blots of total cell lysates derived from the same cells in FIG. 16A and probed with the indicated antibodies.

Caspase-3 Interacts with Tvl-1 Only in Tpl-2 Transfected Cells, but Does Not Interact with Tpl-2.

Figure 17A:
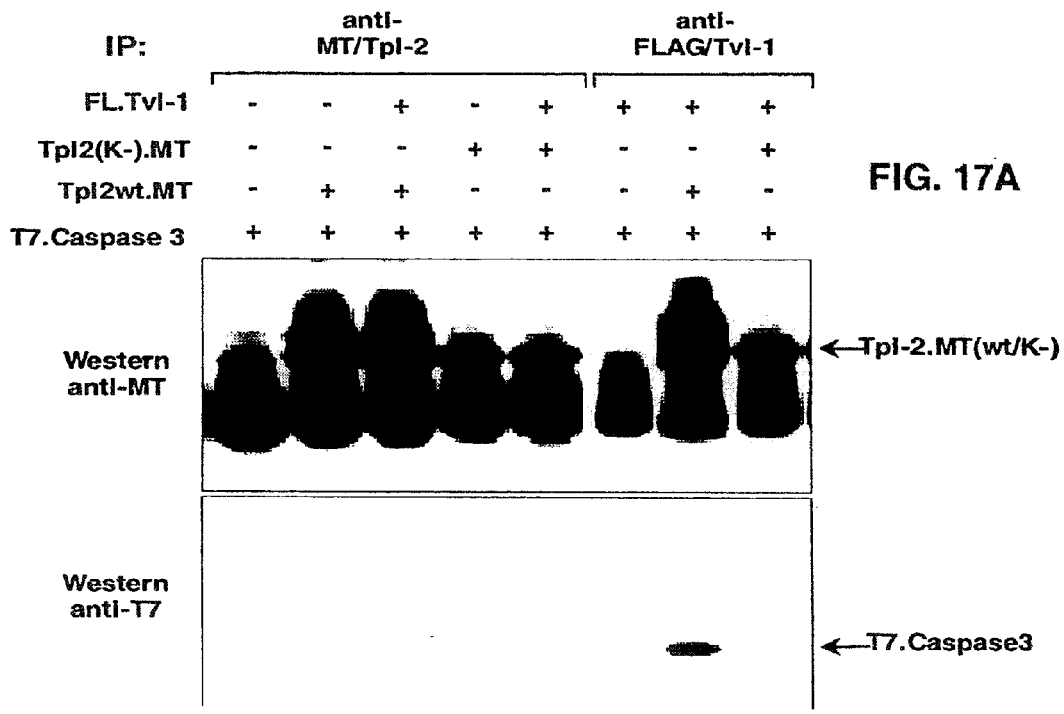
FIG. 17A shows Western blots of the immunoprecipitates were probed with the anti-myc tag (anti-MT) or anti-T7 antibodies as indicated.

Shown in FIG. 17 are Western blots showing that caspase-3 interacts with Tvl-1 only in Tpl-2 transfected cells, but does not interact with Tpl-2.

Figure 17B:
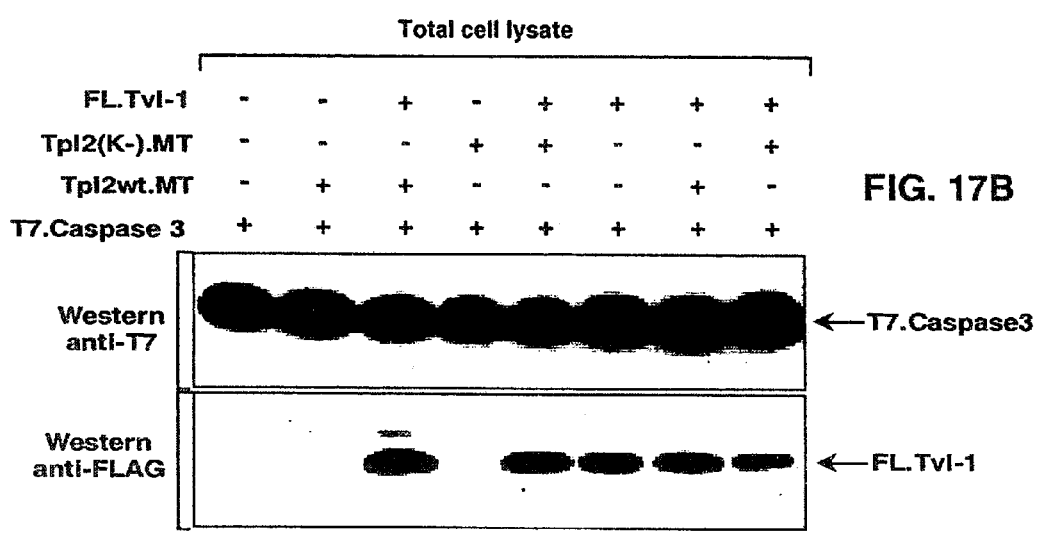
FIG. 17B shows Western blots of total cell lysates derived from the same cells in FIG. 17A and probed with the indicated antibodies.

293T cells were transiently transfected with FLAG-tagged Tvl-1 (FL-Tvl-1, Myc-tagged kinase dead Tpl-2 (Tpl-2(K-)MT), Myc-tagged wild type Tpl-2 (Tbl-2 wt::MT) and T7 tagged caspase-3 (T7::caspase 3) as indicated. See FIG. 17. NP-40 lysates of the transfected cells were immunoprecipitated with the anti-myc tag antibody (anti-MT/Tpl-2) or with the anti-FLAG antibody (anti-FLAG/Tvl-1). Western blots of the immunoprecipitates were probed with the anti-myc tag (anti-MT) or anti-T7 antibodies as indicated. FIG. 17B shows Western blots of total cell lysates derived from the same cells in FIG. 17A and probed with the indicated antibodies.

The Interaction of Tpl-2 and Caspase-3 with Tvl-1 is Inhibited by Myr-Akt

Figure 18A:
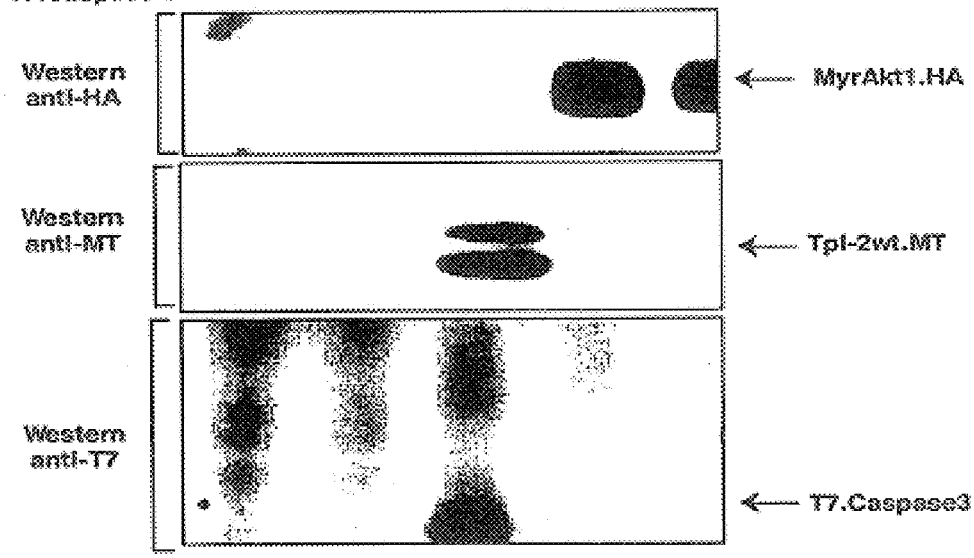
FIG. 18 is the Western blots showing that the interaction of Tpl-2 and caspase-3 with Tvl-1 is inhibited by Myr-Akt.
FIG. 18B shows Western blots of the immunoprecipitates were then probed with the anti-HA, anti-MT, and anti-T7 antibodies as indicated.
Figure 18B:
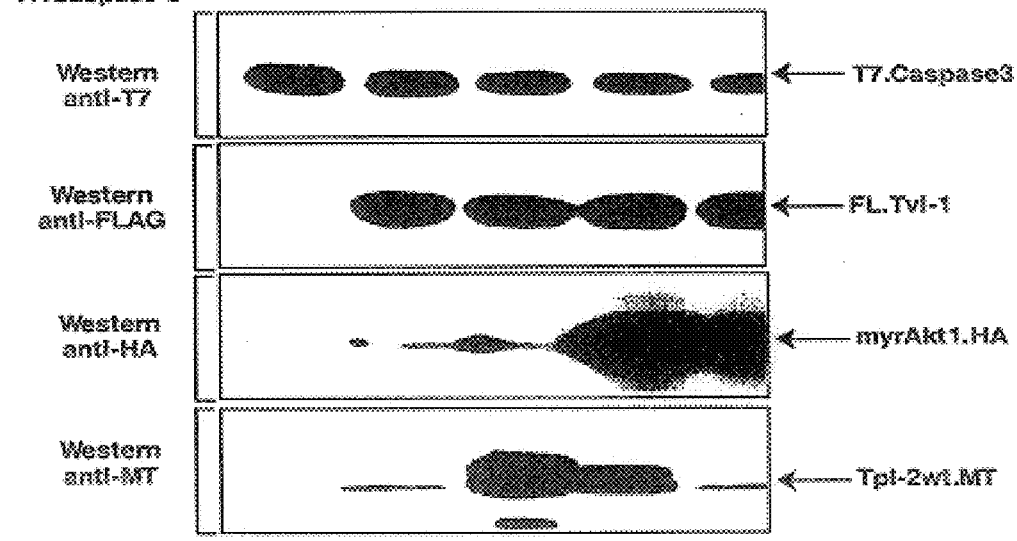

Shown in FIG. 18 are Western blots showing that the interaction of Tpl-2 and caspase-3 with Tvl-1 is inhibited by Myr-Akt. 293T cells were transiently transfected with hemagglutinin-tagged myristylated Akt (Myr:Akt:HA), myc-tagged wild type Tpl-2 (Tpl-2 wt:MT), FLAG-tagged Tvl-1 (FL:Tvl-1) and T7 tagged caspase 3 (T7:caspase 3) as indicated. NP40 lysates of the tranfected cells were immunoprecipitated with the anti-FLAG antibody (anti-FLAG/Tvl-1). Western blots of the immunoprecipitates were then probed with the anti-HA, anti-MT, and anti-T7 antibodies as indicated. See FIG. 18A. FIG. 18B shows Western blots of total cell lysates derived from the same cells in FIG. 17A and probed with the indicated antibodies.

A Model on the Role of Tvl-1 in the Regulation of Apoptosis.

Figure 19:
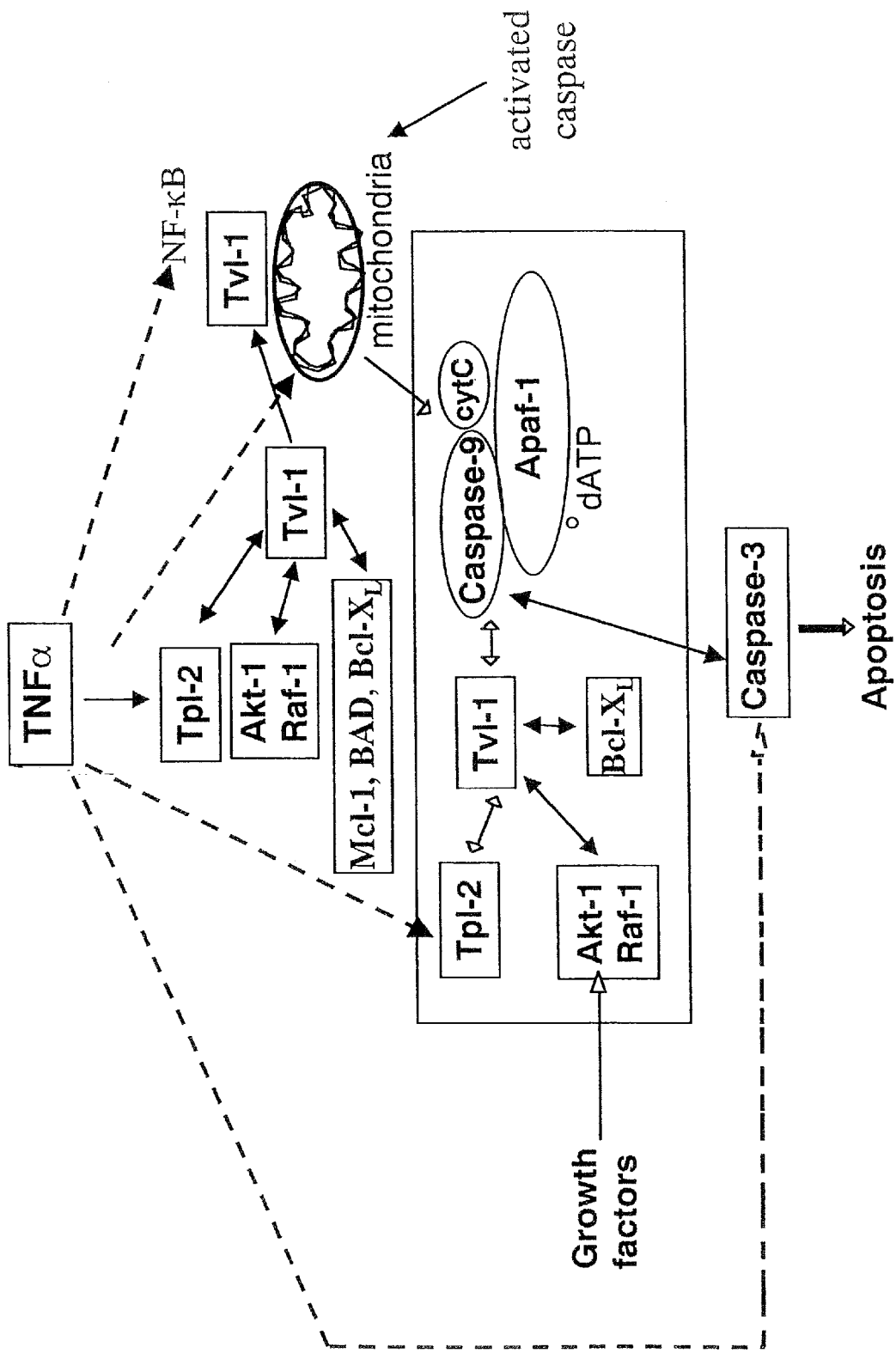
FIG. 19 shows the Model for the role of Tvl-1 in TNF-α-induced apoptosis.

Shown in FIG. 19 is a Model of the Tvl-1 role in TNF-α-induced apoptosis. Information presented here suggests that Tvl-1 may interact with the apoptotic machinery at multiple levels and that it may contribute to the integration of kinase-transduced proapoptotic or antiapoptotic signals into the pathways regulating apoptosis. Based on the data presented herein, we propose that Tvl-1 contributes to the regulation of apoptosis at multiple levels as shown in the model in FIG. 19. In its proposed ability to function at multiple levels, Tvl-1 may be similar to the members of the Bcl-2 family of proteins.

In the proposed model we suggest that Tvl-1 may also inhibit the activation of NF B. This is based on the following considerations. The ankyrin repeat region of Tvl-1 forms a domain of protein-protein interaction that interacts with itself. This suggests that Tvl-1 may also interact with other ankyrin repeat proteins. Such proteins include the NF B inhibitor I B , and the precursors of the p50 and p65 NF B molecules p105 and p100. Binding of Tvl-1 to these proteins may affect their proteolytic cleavage in response to signals that activate NF B and may therefore inhibit NF B activation. Signals originating in TNF-RI activate both the apoptotic pathway and NF B, which, in turn exerts an inhibitory effect on the apoptotic pathway. Inhibition of NF B activation, therefore, will enhance the apoptotic effects of TNF-α, which is exactly the phenotype observed in NIH3T3 cells engineered to overexpress Tvl-1.

EXAMPLE III

TVL-1 and Differentiation, Expression of Genes Linked to the Differentiation Phenotype and Differentation Induced Apoptosis Tvl-1 is Induced During Differentiation and may Regulate the Expression of Genes Linked to the Differentiation Phenotype.

Figure 20:
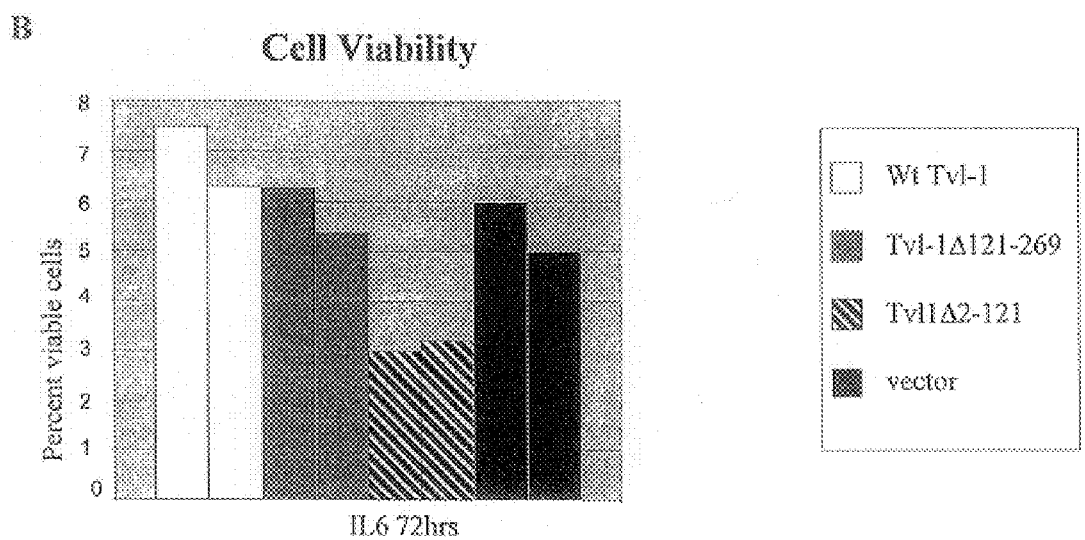
FIG. 20 depicts that Tvl-1 is induced during differentiation and is probably involved in regulating the expression of genes linked to the differentiation phenotype and differentiation-induced apoptosis. (A) Induction of Tvl-1 in M1 cells in response to IL-6 treatment. (B) M1 cells stably transfected with expression constructs of wild type Tvl-1, Tvl-1Δ2-121, Tvl-1x-269 or vector only (three clones of each) were treated with IL-6. To measure cell death cells were stained with propidium iodide at the same time points before and after treatment with IL-6, and they were analyzed by flow cytometry.

The expression of Tvl-1 in two cell lines that can be induced to differentiate (the myelomonocytic cell line M1 and the myogenic cell line $C_2C_{12}$ was examined by Western blotting following induction of differentiation. FIG. 20 is presented to show that FIG. 20 depicts that Tvl-1 is induced during differentiation and is probably involved in regulating the expression of genes linked to the differentiation phenotype and differentiation-induced apoptosis A. Induction of Tvl-1 in M1 cells in response to IL-6 treatment. B. M1 cells stably transfected with expression constructs of wild type Tvl-1, Tvl-1Δ2-121, Tvl-1Δx-269 or vector only (three clones of each) were treated with IL-6. To measure cell death cells were stained with propidium iodide at the same time points before and after treatment with IL-6, and they were analyzed by flow cytometry. The results showed that Tvl-1 was induced during differentiation in both cell lines. FIG. 20 shows that in both the C2C12 and the M1 cells, the induction of Tvl-1 occurs at circa 48 hours from the start of the exposure to the differentiation signal.

Since the induction of Tvl-1 during differentiation coincides with the induction of $G_1$ arrest we propose that this process which is critical for the induction of differentiation may be regulated by Tvl-1. In addition, the induction of Tv-1 coincides with the induction of a series of differentiation markers suggesting that at least some of these markers may be regulted by Tvl-1.

Differentiation of M1 cells is associated with the induction of apoptosis. To determine whether ectopic expression of Tvl-1, Tvl-1Δ2-121 or Tvl-1Δ121-269 influences the induction of apoptosis, we employed propidium iodide staining and flow cytometry to measure the percentage of apoptotic cells in differentiating M1 cultures stably-transfected with these constructs. The results showed that Tvl-1Δ2-121-transfected cells exhibit the lowed survival during differentiation (FIG. 20). These data suggest that Tvl-1 may play a causative role in differentiation-induced apoptosis and that the amino-terminal domain of the protein may be a negative regulator of its proapoptotic function. The proapoptotic function of the ankyrin domain may be due to the fact that it binds and inactivates the antiapoptotic regulator Mcl-1, which is induced during myeloid cell differentiation. Alternatively, it may be due to its ability to induce the expression of proapoptotic genes.

EXAMPLE IV

TVL-1 Regulates Cell Cycle Progression

During Il-6-induced Differentiation of M1 cells the Expression of Tvl-1 is Enhanced. Expression of an Tvl-1Mutant Containing Only the Ankyrin Repeat Region (Tvl-1(2-121)) in These Cells Promotes Growth and Inhibits Il-6-induced G1 Arrest and Differentiation.

Figure 20A:
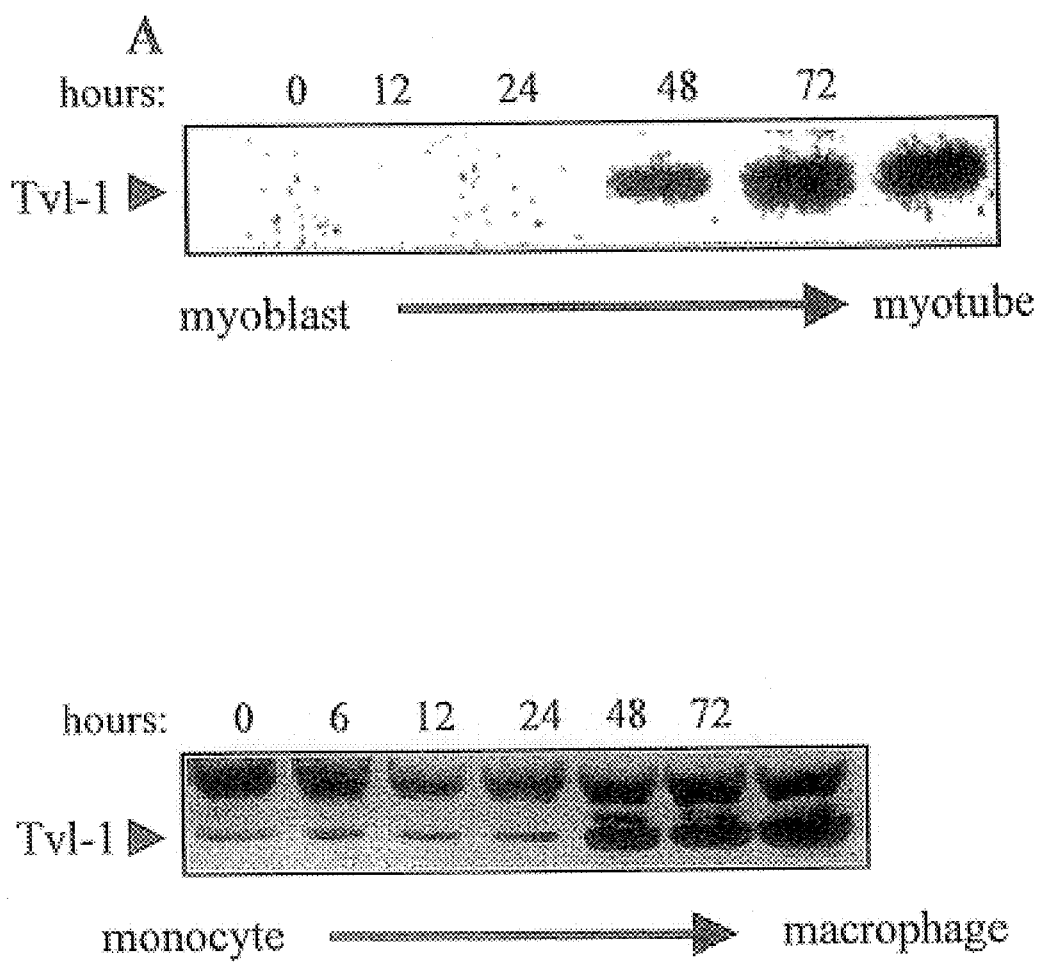

The expression of Tvl-1 in two cell lines that can be induced to differentiate (the myelomonocytic cell line M1 and the myogenic cell line $C_2C_{12}$ was examined by Western blotting following induction of differentiation. The results showed that in both cell lines, Tvl-1 was induced during differentiation. FIG. 20A shows that the induction of Tvl-1 in M1 cells occurs within 48 hours from the start of the exposure to the differentiation signal. This coincides with the induction of G1 arrest.

The upregulation of Tvl-1 during differentiation could either be an expression of the differentiation phenotype or a regulatory event. To address this question we stably transfected M1 cells with expression constructs of the wild type Tvl-1, Tvl-1(2-121) or vector only. Six clones of cells transfected with each construct were isolated by G418 selection. The results showed that the Tvl-1(2-121)-expressing cells proliferate more rapidly than vector transfected or wildtype Tvl-1 transfected cells, and fail to undergo G1 arrest and differentiation in response to Il-6. See FIG. 20. These results suggest that the overexpression of Tvl-1 during differentiation may play an important role in the induction of G1 arrest and differentiation. The Tvl-1 (2–121) mutant may function as a dominant inhibitory molecule that competes with endogenous Tvl-1 and blocks cell cycle arrest and differentiation. The effect of Tvl-1(2-121) on the expression of the endogenous Tvl-1 is currently under investigation.

The following observations provide evidence for the role of Tvl-1 in regulation of the cell cycle:

i) Tvl-1 is expressed in both the nucleus and the cytoplasm.

Figure 21:
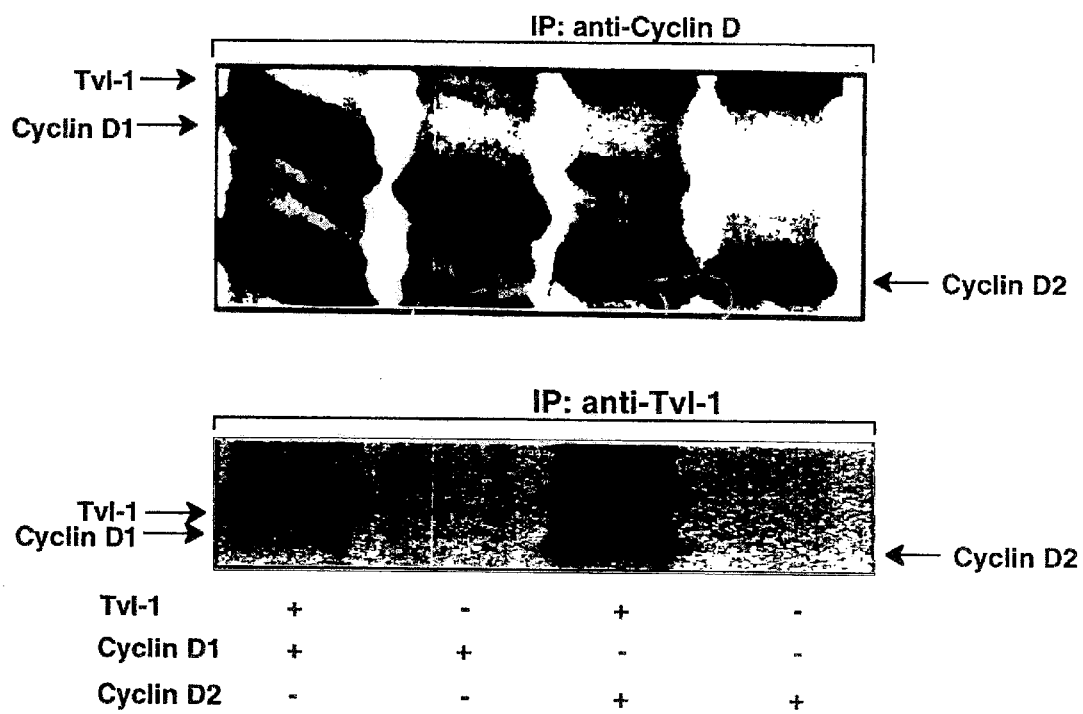
FIG. 21 shows that Tvl-1 interacts with cyclin D1 and cyclin D2.
Figure 22:
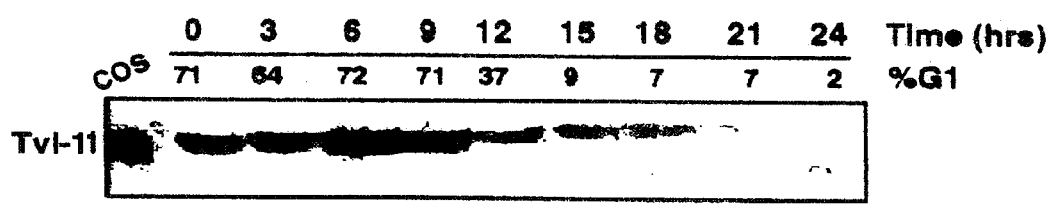
FIG. 22 shows that Tvl-1 expression is down-regulated as the cells progress through G1.

This suggests that Tvl-1 may play a role in the regulation of both cytoplasmic and nuclear events.

ii) Tvl-1 interacts with all D-type cyclins (cyclin D1, D2 and D3). FIG. 21 is presented Tvl-1 interacts with cyclin D1 and cyclin D2. Immunoprecipitation of cyclin-D1/cyclin D2 or Tvl-1 from $^{35}$S-methionine-labeled COS-1 cells, transfected with cyclin D1, cyclin D2 and Tvl-1 expression constructs as indicated. Both D type cyclins and Tvl-1 interact. More recently we showed that Tvl-1 also interacts with cyclin D3 (data not shown). The interaction of Tvl-1 with D-type cyclins was originally demonstrated during the screening of an interaction mating library of approximately 500 molecules for proteins that interact with Tvl-1. The results were confirmed by co-immunoprecipitation of D-type cyclins with Tvl-1 from $^{35}$S methionine-labeled lysates of cells co-transfected with expression constructs of both. See FIG. 21.

iii) Tvl-1 is expressed at the beginning of the G1 phase of the cell cycle and its expression decreases before the cells enter S phase. FIG. 22 is presented to show that Tvl-1 expression is down-regulated as the cells progress through G1. Western blot of total lysates of 4437 cells re-exposed to IL-2 for the indicated times (in hours) after they were synchronized in G1 by IL-2 starvation. The blot was probed with the anti-Tvl-1 antibody. In the upper part of the figure we present the percentage of cells in G1 at the corresponding time points.

Figure 23:
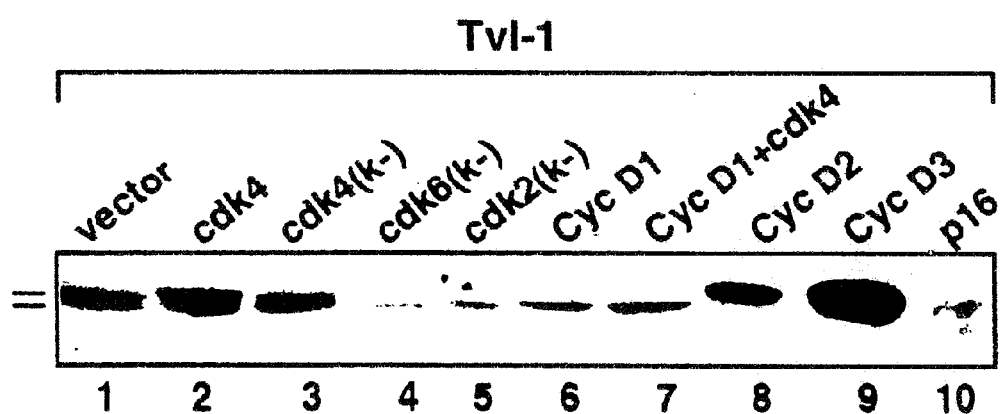
FIG. 23 shows that Tvl-1 migrates as two distinct electrophoretic forms in NIH3T3 cells.

This observation is based on data obtained using two growth factor dependent hematopoietic cell lines. The first line (4437) is an Il-2 dependent rat T cell lymphoma line and the second (32D) is an IL-3-dependent murine myeloid cell line. Cells were synchronized in G1 by IL-2 or IL-3 starvation. Subsequently, the cells were stimulated with the appropriate cytokine and they were harvested at sequential time points as they progressed through G1. FIG. 22 shows a Western blot of these lysates from 4437 cells probed with anti-Tvl-1 antibody as they progress through G1 synchronously.

iv) Tvl-1 Appears to be Phosphorylated when Co-transfected into NIH3T3 Cells with cdk2, cdk6, Cyclin D2 or Cyclin D3 expression constructs. FIG. 23 is presented to show that Tvl-1 migrates as two distinct electrophoretic forms in NIH3T3 cells. The relative abundance of the slower migrating, (phosphorylated?) form is modulated by wild type and mutant cyclin-dependent kinases as well as p16. The relative and absolute abundance of the slower migrating form is enhanced by cyclin D2 and cyclin D3. Cells were transfected with the indicated expression constructs. Western blots of cell lysates, harvested at 48 hours after the transfection, were probed with the anti-Tvl-1 antibody.

Co-transfection with cyclin D2 or cyclin D3 constructs also enhances the levels of Tvl-1 expression. Tvl-1 transiently transfected into NIH3T3 cells gives rise to two differentially migrating bands (FIG. 23). The slower migrating band most likely represents a phosphorylated form of the protein. Co-transfection of a kinase-dead cdk4 mutant does not affect the pattern of Tvl-1 migration. However, co-transfection with active cdk4 shifts the balance toward the slower migrating band, suggesting that cdk4 may phosphorylate Tvl-1 either directly or indirectly. Interestingly, cotransfection of kinase-dead cdk2 or cdk6 mutants totally eliminates the slower migrating band, suggesting that both of these cdk mutants (but not the cdk4 kinase-dead mutant) block the physiological phosphorylation of Tvl-1. Therefore we conclude that although cdk4 may be able to phosphorylate Tvl-1, only cdk2 and cdk6 may be involved in the physiological phosphorylation of the protein.

If cdk2 and cdk6 phosphorylate Tvl-1 (directly or indirectly) then D-type cyclins should contribute to the Tvl-1 phosphorylation. Co-transfection of Tvl-1 with cyclins D1, D2 or D3, with or without cdk4, revealed several interesting facts. Cyclin D2 and cyclin D3 (but not cyclin D1), with or without cdk4, shift the balance toward the putative phosphorylated form of Tvl-1 as expected. In addition, cyclins D2 and D3 increase dramatically the levels of Tvl-1 protein expression. Therefore cyclin D2 and D3 not only promote phosphorylation of Tvl-1 but also increase the overall levels of the protein. This interaction between Tvl-1 and the D-type cyclins suggests that binding may play a role perhaps by stabilizing Tvl-1.

v) The adenoviral protein E1A which interacts with and modulates the activation of several cell cycle-associated proteins enhances expression of Tvl-1.

Figure 24:
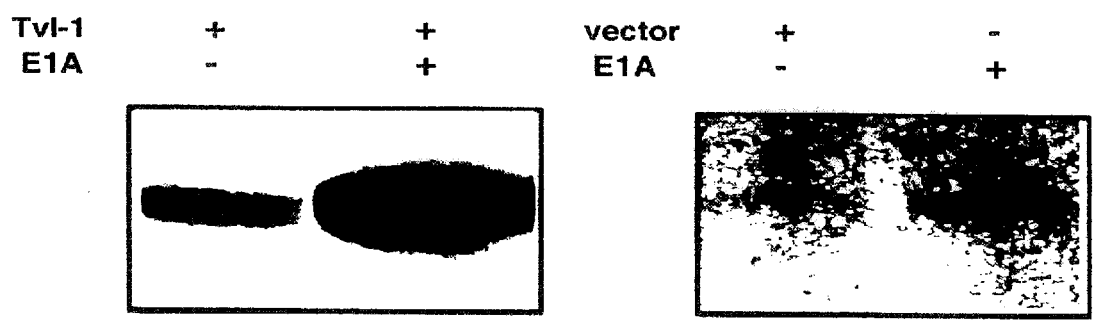
FIG. 24 shows that E1A induces Tvl-1 expression in NIH3T3 cells. Left panel Expression of Tvl-1 from transfected Tvl-1 constructs in response to E1A. Western blot of lysates of NIH3T3 cells, transfected with expression constructs of Tvl-1 and E1A as indicated, was probed with the anti-Tvl-1 antibody. Right panel: Expression of endogenous Tvl-1 in response to E1A. Western blot of lysates of NIH3T3 cells transfected with an E1A expression construct or with the vector only as indicated. The blot was probed with the anti-Tvl-1 antibody.

It is shown in FIG. 24 that E1A induces Tvl-1 expression in NIH3T3 cells. A. Expression of Tvl-1 from transfected Tvl-1 constructs in response to E1A. Western blot of lysates of NIH3T3 cells, transfected with expression constructs of Tvl-1 and E1A as indicated, was probed with the anti-Tvl-1 antibody. B. Expression of endogenous Tvl-1 in response to E1A. Western blot of lysates of NIH3T3 cells transfected with an E1A expression construct or with the vector only as indicated. The blot was probed with the anti-Tvl-1 antibody.

Transient co-transfection of wild type E1A and Tvl-1 expression constructs into NIH3T3 cells revealed that E1A dramatically enhances the expression of Tvl-1 (FIG. 24A). Since E1A could potentially activate the CMV promoter that directs the expression of Tvl-1 from the transfected constructs, we examined whether transiently transfected E1A constructs also enhance the expression of the endogenous Tvl-1 gene. The results showed that high efficiency transient transfection of an E1A expression construct indeed induces endogenous Tvl-1 expression (FIG. 24B).

vi) Additional observations supporting the role of Tvl-1 in the cell cycle.

1) Tvl-1 interacts with Bcl-$X_L$ which is known to inhibit cell cycle progression.
2) Tvl-1 binds Raf-1 which also binds and activates cdc25A, a dual specificity phosphatase. Cdc-25A promotes G1 progression by dephosphorylating several cyclin-dependent kinases, thus contributing to their activation.

The cDNA sequence of Tvl-1 is shown in FIG. 25. The start codon is indicated by the underline and arrow and stop codon is indicated by the underline only.

REFERENCES

1. Rapp, U. R. (1991) *Oncogene* 6, 495–500
2. Morrison, D. K., and Cutler, R. E. (1997) *Curr. Opin. in Cell Biol.* 9, 174–179
3. Avruch, J., Zhang, X. F., and Kyriakis, J. M. (1994) *Trends in Biochem.* 19, 279–283
4. Ghosh, S., Strum, J. C., Sciorra, V. A., Daniel, L., and Bell, R. M. (1996) *J. Biol. Chem.* 271, 8472–8480
5. Kyriakis, J. M., Force, T. L., Rapp, U. R., Bonventre, J. V., and Avruch, J. (1993) *J. Biol. Chem.* 268, 16009–16019
6. Morrison, D. K., Heidecker, G., Rapp, U. R., and Copeland, T. D. (1993) *J. Biol. Chem.* 268, 17309–17316
7. Fabian, J. R., Daar, I. O., and Morrison, D. K. (1993) *Mol. Cell Biol.* 13, 7170–7179
8. Marais, R., Light, Y., Paterson, H. F., and Marshall, C. J. (1995) *EMBO J.* 14, 3136–3145
9. Kolch, W., Heidecker, G., Kochs, G., Hummel, R., Vahidi, H., Mischak, H., Finkenzeller, G., Marme, D., and Rapp, U. R. (1993) *Nature* 364, 249–252
10. Hafner, S., Adler, H. S., Mischak, H., Janosch, P., Heidecker, G., Wolfman, A., Pippig, S., Lohse, M., Ueffing, M., and Kolch, W. (1994) *Mol. Cell. Biol.* 14, 6696–6703
11. Dent, P., Reardon, D. B., Wood, S. L., Lindorfer, M. A., Graber, S. G., Garrison, J. C., Brautigan, D. L., and Sturgill, T. W. (1996) *J. Biol. Chem.* 271, 3119–3123
12. Popik, W., and Pitha, P. M. (1996) *Mol. Cell Biol.* 16, 6532–6541
13. Park, R. K., Liu, Y., and Durden, D. L. (1996) *J. Biol. Chem.* 271, 13342–13348
14. Freed, E., Symons, M., Macdonald, S. G., McCormick, F., and Ruggieri, R. (1994) *Science* 265, 1713–1716
15. Fantl, W. J., Muslin, A. J., Kikuchi, A., Martin, J. A., MacNicol, A. M., Gross, R. W., and Williams, L. T. (1994) *Nature* 371, 612–614
16. Irie, K., Gotoh, Y., Yashar, B. M., Errede, B., Nishida, E., and Matsumoto, K. (1994) *Science* 265, 1716–1719
17. Wartmann, M., and Davis, R. J. (1994) *J. Biol. Chem.* 269, 6695–6701
18. Stepanova, L., Leng, X., Parker, S. B., and Harper, J. W. (1996) *Genes Dev.* 10, 1491–1502
19. Schulte, T. W., Blagosklonny, M. V., Ingui, C., and Neckers, L. (1995) *J. Biol. Chem.* 270, 24585–24588
20. Zhang, X. F., Settleman, J., Kyriakis, J. M., Takeuchi-Suzuki, E., Elledge, S. J., Marshall, M. S., Bruder, J. T., Rapp, U. R., and Avruch, J. (1993) *Nature* 364, 308–313
21. Vojtek, A. B., Hollenberg, S. M., and Cooper, J. A. (1993) *Cell* 74, 205–214
22. Warne, P. H., Viciana, P. R., and Downward, J. (1993) *Nature* 364, 352–355
23. Leevers, S. J., Paterson, H. F., and Marshall, C. J. (1994) *Nature* 369, 411–414
24. Stokoe, D., Macdonald, S. G., Cadwallader, K., Symons, M., and Hancock, J. F. (1994) *Science* 264, 1463–1467
25. Luo, Z., Tzivion, G., Belshaw, P. J., Vavvas, D., Marshall, M., and Avruch, J. (1996) *Nature* 383, 181–185
26. Farrar, M. A., Alberol, I., and Perlmutter, R. M. (1996) *Nature* 383, 178–181
27. Chuang, E., Barnard, D., Hettich, L., Zhang, X. F., Avruch, J., and Marshall, M. S. (1994) *Mol. Cell. Biol.* 14, 5318–5325
28. Ghosh, S., and Bell, R. M. (1994) *J. Biol. Chem.* 269, 30785–30788
29. Nassar, N., Horn, G., C., H., Scherer, A., McCormick, F., and Wittinghofer, A. (1995) *Nature* 375, 554–560
30. Luo, Z. J., Zhang, X. F., Rapp, U., and Avruch, J. (1995) *J. Biol. Chem.* 270, 23681–23687
31. Dent, P., Haser, W., Haystead, T. A., Vincent, L. A., Roberts, T. M., and Sturgill, T. W. (1992) *Science* 257, 1404–1407
32. Howe, L. R., Leevers, S. J., Gomez, N., Nakielny, S., Cohen, P., and Marshall, C. J. (1992) *Cell* 71, 335–342
33. Kyriakis, J. M., App, H., Zhang, X. F., Banerjee, P., Brautigan, D. L., Rapp, U. R., and Avruch, J. (1992) *Nature* 358, 417–421
34. Galaktionov, K., Jessus, C., and Beach, D. (1995) *Genes Dev.* 9, 1046–1058
35. Wang, H. G., Rapp, U. R., and Reed, J. C. (1996) *Cell* 87, 629–638
36. Brent, R., and Ptashne, M. (1985) *Cell* 43, 729–736 37. Gyuris, J., Golemis, E., Chertkov, H., and Brent, R. (1993) *Cell* 75, 791–803
38. Golemis, E. A., and Khazak, V. (1997) *Methods Mol Biol.* 63, 197–218
39. Finley, R. L., Jr., and Brent, R. (1994) *Proc. Natl. Acad. Sci. USA* 91, 12980–12984
40. Chomczynski, P., and Sacchi, N. (1987) *Anal. Biochem.* 162, 156–159
41. Patriotis, C., Makris, A., Chernoff, J., and Tsichlis, P. N. (1994) *Proc. Natl. Acad. Sci. USA* 91, 9755–9759
42. Andersson, S., Davis, D. L., Dahlback, H., Jornvall, H., and Russell, D. W. (1989) *J. Biol. Chem.* 264, 8222–8229
43. Morrison, D. K. (1995) *Methods in Enzymology* 255, 301–310
44. Gardner, A. M., Vaillancourt, R. R., and Johnson, G., L. (1993) *J. Biol. Chem.* 268, 17896–17901
45. Michaely, P., and Bennett, V. (1992) *Trends Cell Biol.* 2, 127–129
46. Chan, W., Kordeli, E., and Bennett, V. (1994) *J. Cell Biol.* 123, 1463–1473
47. Yu, Y. T., Breitbart, R. E., Soot, L. B., Lee, Y., Mahdavi, V., and Nadal-Ginard, B. (1992) *Genes Dev.* 6, 1783–1798
48. Hobson, G. M., Krahe, R., Garcia, E., Siciliano, M. J., and Funanage, V. L. (1995) *Genomics* 29, 704–711
49. Matsuno, K., Go, M. J., Sun, X., Eastman, D. S., and Artavanis-Tsakonas, S. (1997) *Development* 124, 4265–4373.
50. Zheng, C. F., and Guan, K. L. (1994) *EMBO J.* 13, 1123–1131

51. Williams, N. G., Roberts, T. M., and Li, P. (1992) *Proc. Natl. Acad. Sci. USA* 89, 2922–2926
52. Buscher, D., Hipskind, R. A., Krautwald, S., Reimann, T., and Baccarini, M. (1995) *Mol. Cell Biol.* 15, 466–475
53. Dent, P., Reardon, D. B., Morrison, D. K., and Sturgill, T. W. (1995) *Mol. Cell Biol.* 15, 4125–4135
54. Stokoe, D., and McCormick, F. (1997) *EMBO J.* 16, 2384–2396
55. Macdonald, S. G., Crews, C. M., Wu, L., Driller, J., Clark, R., Erikson, R. L., and McCormick, F. (1993) *Mol. Cell Biol.* 13, 6615–6620

While certain preferred embodiments of the present invention have been described and specifically exemplified above, it is not intended that the invention be limited to such embodiments. Various modifications may be made to the invention without departing from the scope and spirit thereof as set forth in the following claims.

---

What is claimed is:

1. An isolated protein between about 250 and 270 amino acids in length, the protein comprising a plurality of ankyrin repeat domains and capable of promoting TNFα-induced apoptosis, wherein said protein is a product of expression of part or all of the nucleic acid of SEQ ID NO:1.

2. An isolated polypeptide having a part of amino acids set forth in SEQ ID NO:2 or all of amino acids set forth in SEQ ID NO:2 or encoded by a nucleic acid molecule having a sequence selected from the group consisting of:

(a) a sequence set forth in SEQ ID NO:1 or a fragment thereof;

(b) a sequence hybridizing under stringent conditions with part or all of the complementary strand of SEQ ID NO:1, and wherein said conditions include incubation at 37–42° C. for at least six hours in a hybrization solution comprising: 5×SSC, 5×Denhardt's reagent, 1.0% SDS, 100 mg/ml denatured, fragmented salmon sperm DNA, 0.05% sodium pyrophosphate and up to 50% formamide and wherein the isolated polypeptide is capable of interacting with Raf-1 and capable of promoting TNFα-induced apoptosis.

3. An isolated polypeptide encoded by a nucleic acid molecule having a sequence set forth in SEQ ID NO:1.

4. The isolated polypeptide of claim 2, wherein the polypeptide is encoded by the nucleic acid molecule having a sequence hybridizing under stringent hybridization conditions with part or all of the complementary strand of SEQ ID NO:1.

5. The isolated polypeptide of claim 2, wherein the polypeptide has all of the amino acids set forth in SEQ ID NO:2.

6. An isolated protein having an amino acid sequence the same as that set forth in SEQ ID NO:2.

7. The isolated protein of claim 6, wherein said protein is encoded by a nucleic acid set forth in SEQ ID NO:1.

8. The isolated polypeptide of claim 5, wherein the part is selected from the group consisting of:

(a) a sequence comprising amino acids 1–138 set forth in SEQ ID NO:2;

(b) a sequence comprising amino acids 1–259 set forth in SEQ ID NO:2;

(c) a sequence comprising amino acids 61–269 set forth in SEQ ID NO:2;

(d) a sequence comprising amino acids 86–269 set forth in SEQ ID NO:2; and (e) a sequence comprising amino acids 132–269 set forth in SEQ ID NO:2.

* * * * *

SEQUENCE LISTING

<160> NUMBER OF SEQ ID NOS: 10

<210> SEQ ID NO 1
<211> LENGTH: 1160
<212> TYPE: DNA
<213> ORGANISM: Artificial Sequence
<220> FEATURE:
<223> OTHER INFORMATION: Murine Tvl-1 cDNA

<400> SEQUENCE: 1

| | | | | | |
|---|---|---|---|---|---|
| gtcgcgtatt | aagttgctgc | tctatgtccc | aggagaggaa | gctagagaac | tgagcgtctg | 60 |
| gtcaccaact | tgctctttac | gagatctact | gaaccagaaa | agtttgttga | acagagtctt | 120 |
| cctgagtttt | ggaagaccaa | ggctggcagc | gtagggacaa | agaggaggct | ggagggagct | 180 |
| tcctccatgg | agcccactca | ggttgcagag | aaccttgtcc | caaaccagca | acctcctgtt | 240 |
| cctgacctag | aggatcctga | ggacaccaga | gatgagtccc | cagagaactc | agacactgtc | 300 |
| gtcctcagcc | tgttcccctg | cacccagat | gctgtgaatc | ctgaagcaga | tgccagtgca | 360 |
| tcctcactgc | agggaagttt | cttgaagcac | tccacaaccc | tcacaaaccg | gcaacgtggg | 420 |
| aatgaggtct | cagctctgcc | agccaccctg | gactcccttt | ctatccacca | gcttgcagcc | 480 |
| caaggggagc | tgagccaact | gaaggatcat | ctgcggaagg | gtgcgtgtcc | tgcctgcaca | 540 |
| tgcctgtctg | gaaacaacct | gatcaacaaa | ccggatgagc | gtggcttcac | cccctcatc | 600 |
| tgggcctcag | cctttggaga | aattgagaca | gttcgcttcc | tgctagactg | gggtgctgac | 660 |
| ccccacatcc | tggccaagga | gcgggagagc | gcactgtcac | ttgccagtat | gggtggctac | 720 |
| acggacatcg | tgaggttgct | gcttgaccgt | gacgtggata | tcaacatcta | tgactggaat | 780 |
| ggaggaacac | cactgctcta | tgctgtgcgt | gggaaccacg | tgaagtgtgt | ggaggcctta | 840 |
| ctggcccggg | gtgctgacct | caccacagag | gctgactctg | gctacacccc | aatggatctc | 900 |
| gcagtggccc | tgggataccg | caaagtgcaa | caggtgatgg | agagccacat | cctcagattg | 960 |
| ttccagagca | ccctggggcc | tgtggacccc | gagtgaagac | agcctgctgg | gaacccaggc | 1020 |
| actcagggac | agtcagccca | caactggctt | gaaaggcagc | tcctggacag | tggtgggaaa | 1080 |
| agccctccgc | aacaggaacc | aataaatctg | tgcagaactt | aaaaaaaaaa | aaaaaaaact | 1140 |
| cgagaagctt | tggacttctt | | | | | 1160 |

<210> SEQ ID NO 2
<211> LENGTH: 269
<212> TYPE: PRT
<213> ORGANISM: Artificial Sequence
<220> FEATURE:
<223> OTHER INFORMATION: Amino acid sequence of the murine Tvl-1 protein

<400> SEQUENCE: 2

-continued

```
Met Glu Pro Thr Gln Val Ala Glu Asn Leu Val Pro Asn Gln Gln Pro
1               5                   10                  15

Pro Val Pro Asp Leu Glu Asp Pro Glu Asp Thr Arg Asp Glu Ser Pro
                20                  25                  30

Glu Asn Ser Asp Thr Val Val Leu Ser Leu Phe Pro Cys Thr Pro Asp
            35                  40                  45

Ala Val Asn Pro Glu Ala Asp Ala Ser Ala Ser Leu Gln Gly Ser
    50                  55                  60

Phe Leu Lys His Ser Thr Thr Leu Thr Asn Arg Gln Arg Gly Asn Glu
65                  70                  75                  80

Val Ser Ala Leu Pro Ala Thr Leu Asp Ser Leu Ser Ile His Gln Leu
                85                  90                  95

Ala Ala Gln Gly Glu Leu Ser Gln Leu Lys Asp His Leu Arg Lys Gly
                100                 105                 110

Ala Cys Pro Ala Cys Thr Cys Leu Ser Gly Asn Asn Leu Ile Asn Lys
            115                 120                 125

Pro Asp Glu Arg Gly Phe Thr Pro Leu Ile Trp Ala Ser Ala Phe Gly
        130                 135                 140

Glu Ile Glu Thr Val Arg Phe Leu Leu Asp Trp Gly Ala Asp Pro His
145                 150                 155                 160

Ile Leu Ala Lys Glu Arg Glu Ser Ala Leu Ser Leu Ala Ser Met Gly
                165                 170                 175

Gly Tyr Thr Asp Ile Val Arg Leu Leu Leu Asp Arg Asp Val Asp Ile
            180                 185                 190

Asn Ile Tyr Asp Trp Asn Gly Gly Thr Pro Leu Leu Tyr Ala Val Arg
        195                 200                 205

Gly Asn His Val Lys Cys Val Glu Ala Leu Leu Ala Arg Gly Ala Asp
    210                 215                 220

Leu Thr Thr Glu Ala Asp Ser Gly Tyr Thr Pro Met Asp Leu Ala Val
225                 230                 235                 240

Ala Leu Gly Tyr Arg Lys Val Gln Gln Val Met Glu Ser His Ile Leu
                245                 250                 255

Arg Leu Phe Gln Ser Thr Leu Gly Pro Val Asp Pro Glu
        260                 265
```

<210> SEQ ID NO 3
<211> LENGTH: 33
<212> TYPE: PRT
<213> ORGANISM: Artificial Sequence
<220> FEATURE:
<223> OTHER INFORMATION: Amino acid sequence of the 1st ankyrin repeat
      in the Tvl-1 protein

<400> SEQUENCE: 3

```
Arg Gly Phe Thr Pro Leu Ile Trp Ala Ser Ala Phe Gly Glu Ile Glu
1               5                   10                  15

Thr Val Arg Phe Leu Leu Asp Trp Gly Ala Asp Pro His Ile Leu Ala
                20                  25                  30

Lys
```

<210> SEQ ID NO 4
<211> LENGTH: 33
<212> TYPE: PRT
<213> ORGANISM: Artificial Sequence
<220> FEATURE:
<223> OTHER INFORMATION: Amino acid seuence of the 2nd ankyrin repeat
      in the Tvl-1 protein

```
<400> SEQUENCE: 4

Glu Arg Glu Ser Ala Leu Ser Leu Ala Ser Met Gly Gly Tyr Thr Asp
1               5                   10                  15

Ile Val Arg Leu Leu Leu Asp Arg Asp Val Asp Ile Asn Ile Tyr Asp
            20                  25                  30

Trp

<210> SEQ ID NO 5
<211> LENGTH: 33
<212> TYPE: PRT
<213> ORGANISM: Artificial Sequence
<220> FEATURE:
<223> OTHER INFORMATION: Amino acid sequence of the 3rd ankyrin repeat
      in the Tvl-1 protein

<400> SEQUENCE: 5

Glu Arg Glu Ser Ala Leu Ser Leu Ala Ser Met Gly Gly Tyr Thr Asp
1               5                   10                  15

Ile Val Arg Leu Leu Leu Asp Arg Asp Val Asp Ile Asn Ile Tyr Asp
            20                  25                  30

Trp

<210> SEQ ID NO 6
<211> LENGTH: 33
<212> TYPE: PRT
<213> ORGANISM: Artificial Sequence
<220> FEATURE:
<223> OTHER INFORMATION: Amino acid sequence of the 4th ankyrin repeat
      in the Tvl-1 protein

<400> SEQUENCE: 6

Ser Gly Tyr Thr Pro Met Asp Leu Ala Val Ala Leu Gly Tyr Arg Lys
1               5                   10                  15

Val Gln Gln Val Met Glu Ser His Ile Leu Arg Leu Phe Gln Ser Thr
            20                  25                  30

Leu

<210> SEQ ID NO 7
<211> LENGTH: 28
<212> TYPE: PRT
<213> ORGANISM: Artificial Sequence
<220> FEATURE:
<223> OTHER INFORMATION: Amino acid sequence of the consensus ankyrin
      repeat sequence

<400> SEQUENCE: 7

Gly Thr Pro Leu His Leu Ala Ala Arg Gly His Val Glu Val Val Lys
1               5                   10                  15

Leu Leu Leu Asp Gly Ala Asp Val Asn Ala Thr Lys
            20                  25

<210> SEQ ID NO 8
<211> LENGTH: 18
<212> TYPE: PRT
<213> ORGANISM: Artificial Sequence
<220> FEATURE:
<223> OTHER INFORMATION: Amino acid sequence of the consensus ankyrin
      repeat sequence

<400> SEQUENCE: 8

Ser Ala Ile Ser Gln Asn Asn Leu Asp Ile Ala Glu Val Lys Asn Pro
1               5                   10                  15
```

```
Asp Asp

<210> SEQ ID NO 9
<211> LENGTH: 9
<212> TYPE: PRT
<213> ORGANISM: Artificial Sequence
<220> FEATURE:
<223> OTHER INFORMATION: Amino acid sequence of the consensus ankyrin
      repeat sequence

<400> SEQUENCE: 9

Val Lys Thr Met Arg Gln Ser Ile Ala
1               5

<210> SEQ ID NO 10
<211> LENGTH: 33
<212> TYPE: PRT
<213> ORGANISM: Artificial Sequence
<220> FEATURE:
<223> OTHER INFORMATION: Amino acid sequence of the 5th ankyrin repeat
      (conditional ANK)

<400> SEQUENCE: 10

Asp Ser Leu Ser Ile His Gln Leu Ala Ala Gln Gly Glu Leu Ser Gln
1               5                   10                  15

Leu Lys Asp His Leu Arg Lys Gly Asn Asn Leu Ile Asn Lys Pro Asp
            20                  25                  30

Glu
```